US005641480A

United States Patent [19]
Vermeer

[11] Patent Number: 5,641,480
[45] Date of Patent: Jun. 24, 1997

[54] HAIR CARE COMPOSITIONS COMPRISING HETEROATOM CONTAINING ALKYL ALDONAMIDE COMPOUNDS

[75] Inventor: Robert Vermeer, Nutley, N.J.

[73] Assignee: Lever Brothers Company, Division of Conopco, Inc., New York, N.Y.

[21] Appl. No.: 352,309

[22] Filed: Dec. 8, 1994

[51] Int. Cl.$^6$ .............................. A61K 7/07; A61K 7/075
[52] U.S. Cl. ...................................... 424/70.24; 424/70.1
[58] Field of Search ............................ 424/70.1, 70.13, 424/70.17, 70.24

[56] References Cited

U.S. PATENT DOCUMENTS

| | | | |
|---|---|---|---|
| 2,662,073 | 12/1953 | Mehltretter et al. | 536/17.2 |
| 2,721,211 | 10/1955 | Buc | 260/562 |
| 2,752,334 | 6/1956 | Walton | 260/211 |
| 2,776,951 | 1/1957 | Melamed | 536/17.2 |
| 2,785,152 | 3/1957 | Jones | 260/112 |
| 3,766,267 | 10/1973 | Zak | 260/561 B |
| 3,855,290 | 12/1974 | Zak et al. | 260/561 B |
| 3,990,991 | 11/1976 | Gerstein | 252/542 |
| 4,038,294 | 7/1977 | Conner et al. | 260/501.15 |
| 4,190,429 | 2/1980 | Rutter et al. | 71/67 |
| 4,342,706 | 8/1982 | Conner et al. | 260/404.5 |
| 4,529,588 | 7/1985 | Smith et al. | 260/561 B |
| 4,534,964 | 8/1985 | Herstein et al. | 424/70 |
| 4,618,675 | 10/1986 | Lichtenthaler | 536/17.2 |
| 4,973,473 | 11/1990 | Schneider et al. | 424/6 |
| 5,037,973 | 8/1991 | Meinetsberger | 260/102 |
| 5,084,270 | 1/1992 | Ciaudelli | 424/59 |

FOREIGN PATENT DOCUMENTS

| | | |
|---|---|---|
| 2523962 | 9/1983 | France . |
| 2321752 | 11/1974 | Germany . |
| 2338087 | 1/1975 | Germany . |
| 62-327860 | 7/1989 | Japan . |
| 94/12511 | 6/1994 | WIPO . |

OTHER PUBLICATIONS

Synthetic Emulsifying Agents, Fieser et al., Jun. 20, 1956, vol. 78, pp. 2825–2832.

Linking Sugars with Amino Acid Esters of Lipophilic Alcohols to Form Surface–Active Sugar Derivatives, Geyer, vol. 330 9 (1963), pp.182–188 (English Translation).

Reaction of Aliphatic Diamines with D–Gluconic Acid δ–Lactone, Geyer, vol. 97 (1964), pp. 2271–2275 (English Translation).

Amphiphilic Properties of Synthetic Glycolipids Based on Amide Linkages, I. Electron Microscopic Studies on Aqueous Gels, Chem. & Physics of Lipids 37 (1985) 227–240.

The Chiral Bilayer Effect Stabilizes Micellar Fibers, Fuhrhop et al., J.Am. Chem. Soc., vol. 109, No. 11; pp. 3386–3390 & Supplemental Material.

Lipid Bilayer Fibers from Diastereomeric and Enantiomeric N–Octylaldonamides, Fuhrhop et al., J. Am. Chem. Soc., 1988, 110, pp. 2861–2867.

Stereochemistry and Curvature Effects in Supramolecular Organization and Separation Process of Micellar N–Alkylaldonamide Mixtures, Fuhrhop et al., J. Am. Chem. Soc., 1990, 112, pp. 1768–1775.

A New Family of Liquid Crystals: N–Substituted Aldonamides, Mol. Cryst. Liq. Cryst. 1986, vol. 135, pp. 93–110.

Molecular Packing and Hydrogen Bonding in the Crystal Structures of the N–(n–Alkyl)–D–gluconamide and the 1–Deoxy–(N–methyl–alkanamido)–D–glucitol Mesogens, Mol. Cryst. Liq. Cryst. 1990, vol. 185, pp . 209–213.

Molecular Crystals and Liquid Crystals, vol. 198 (1991).

Amphiphilic Properties of Synthetic Glycolipids Based on Amide Linkages, Zabel et al., Chemistry and Physics of Lipids, 39 (1986) 313–327.

Liquid–crystalline Behaviour in the N–alkyl Gluconamides and Other Related Carbohydrates, Pfanhemuller, Liquid Crystals, 1986, vol. 1, vol. 1, No. 4, 357–370.

Amphiphilic Properties of Synthetic Glycolipids Based in Amide Linkages, Makromol, Chem. 189, 2433–2442 (1988).

Molecular and Crystal Structures of N–(n–Heptyl)–and N–(n–Decyl)–D–Glyconamide, Fahrnow et al., Carbohydrate Research 176 (1988) 165–174).

Supramolecular Assemblies of Diacetylenic Aldonamids, Frankel et al., J. Am. Chem. Soc., 1991, 113, 7436–7437.

A New Class of Model Glycolipids; Synthesis, Characterization, and Interaction with Lectins, Williams et al., Archives of Biochemistry and Biophysics, vol. 195, No. 1, Jun., pp. 145–151, 1979.

Synthesis of a New Class of Model Glycolipids, Williams et al. —Carbohydrate Research, 67 (1978) C1–C3.

Technical Notes, Scholnick et al, pp. 471–473.

Compositions Comprising Nonionic Glycolipid Surfactants, Filed as U.S. Ser. No. 816,419.

Light Scattering from Nonionic Surfactants of the Sugar–Lipid Hybrid Type in Aqueous Solution, Denkinger et al., J. Phys. Chem., 1989, 93, pp. 1428–1434.

Investigations of a Series of Nonionic Surfactants of Sugar–Lipid Hybrids by Light Scattering and Electron Microscopy, Denkinger et al., Colloid & Polymer Science 268:513 527 (1990).

Monolayers from Synthetic Glycolipids, Emmerling, Polymer Bulletin 6, 305–308 (1982).

Synthesis of New Fluorinated Nonionic Surfactants Derived from Lactose, Ghoul, Journal of Fluoride Chemistry, 59 (1992) 107–112.

Conformational Effects of 1,3–syn–Diaxial Repulsion and 1,2–gauche Attraction Between Hydroxy Groups in Monomolecular N–Octyl–D–Hexonamide Solutions, Svenson et al., J. Chem. Soc., Perkin Trans 2, 1994,pp. 1023–1028.

Primary Examiner—Salle M. Gardner
Attorney, Agent, or Firm—Ronald A. Koatz

[57] ABSTRACT

The invention relates to hair care compositions containing heteroatom containing alkyl aldonamide compounds and hair conditioning agents. Unexpectedly, applicants have found that when these heteroatom containing alkyl aldonamides are used, benefits such as enhanced stability and/or enhanced viscosity are obtained relative to the use of other known thickeners or non-heteroatom containing aldonamides.

1 Claim, No Drawings

HAIR CARE COMPOSITIONS COMPRISING HETEROATOM CONTAINING ALKYL ALDONAMIDE COMPOUNDS

TECHNICAL FIELD

The present invention is related to new hair care compositions that have improved foam, viscosity, clarity and conditioning characteristics due to the inclusion of a new type of alkyl aldonamide compound, specifically heteroatom containing alkyl aldonamide compounds.

BACKGROUND OF THE INVENTION

The hair of the head has been associated with beauty and social distinction. For this reason, a special importance is attached in the cosmetic area to hair care products such as rinses, conditioners, shampoos, conditioning shampoos and the like.

The primary function of a hair care composition is to cleanse the hair and scalp from soil without stinging or irritating the eyes and scalp. Hair soil includes natural skin secretions (such as sebum), skin debris, dirt from the environment and residue from hair-grooming products applied by the consumer. After accomplishing the cleansing action, the shampoo should not excessively remove the natural oil from the scalp and should leave the hair soft, lustrous and manageable while simultaneously providing a rich copious foam or lather. This has become a difficult challenge to meet and it is not surprising to find that considerable resource and effort have been directed towards the discovery and development of new ingredients that provide improved foam, viscosity, clarity and conditioning characteristics. The patent literature, cosmetic journals and formularies describe many such ingredients, however, they still do not provide all the answers to the problems encountered in making a totally satisfactory product.

It has now been found that the inclusion of a heteroatom containing alkyl aldonamide compound in a hair care composition of the invention, surprisingly provides improved foam, viscosity, clarity and conditioning characteristics. These findings are quite unexpected and have not been recognized or appreciated in the art.

The hair care compositions of the present invention may be in aerosol, liquid, gel, creme (cream), lotion, paste, granular, powdered, tablet or bar form. Included among the hair care compositions are rinses, conditioners, shampoos, conditioning shampoos, antidandruff shampoos and the like. However, the conditioners, shampoos, conditioning shampoos and antidandruff shampoos are the preferred compositions.

Foam

The ability of a hair care composition to create a desirable rich lather is a significant driving force in the selection of that product. This important psychological stimulus derived from tactile and visual perceptions by the consumer, make it necessary to formulate compositions with ingredients that generate a high level of stable foam or lather. Furthermore, the generation of a thick, persistent lather also serves as a vehicle to suspend dirt and prevent redeposition during the rinse cycle. Surprisingly the hair care compositions of the invention that comprise a heteroatom containing alkyl aldonamide compound produce an enhanced, thick, copious, persistent foam and lather.

By contrast, compositions that lack a heteroatom containing alkyl aldonamide compound exhibit low viscosity and poor foam.

Viscosity/Clarity

The viscosity or thickness of a hair care composition also plays an important role in the selection of that product, since consumers are accustomed to, and expect hair care compositions to be thick and viscous. If a hair care composition is thin and nonviscous, a consumer may conclude that the product is inferior. Furthermore, successful hair care compositions must have good shelf life and should not become turbid or produce sedimentation upon standing. Ideal hair care compositions should cleanse the hair gently and should not overdry the scalp. Surprising the hair care compositions of the present invention that comprise a heteroatom containing alkyl aldonamide compound produce clear, stable, thick liquid compositions with good conditioning properties. This is unusual and unexpected, since alkyl aldonamides that lack heteroatoms generally form opaque, nontransparent liquid compositions which are instead useful as opacifying or pearlescent agents.

Background Art Alkyl Aldonamides

An aldonamide is defined as the amide of an aldonic acid (or aldonolactone) and an aldonic acid, in turn is defined as a sugar substance in which the pseudoaldehyde or pseudoketose group, generally found at the $C_1$ or $C_2$ position on the sugar, has been oxidized to a carboxylic acid group which upon drying cyclizes to an aldonolactone.

Aldonamides may be based on compounds comprising one saccharide unit (e.g., ribonamides, gluconamides or glucoheptonamides), two saccharide units (e.g., lactobionamides, maltobionamides, melibionarnides, cellobionamides, gentiobionamides or D-glucopyranosyl-(1–5)-D-arabinonamides) or they may be based on compounds comprising more than two saccharide units. Any carbohydrate can be used as long as the sugar has a pseudoaldehyde or pseudoketose group available for oxidation to a carboxylic acid group.

While alkyl aldonamides are known in the art, there is no teaching or suggestion of using heteroatom containing alkyl aldonamide compounds of the invention as foam stabilizers, viscosity modifiers or conditioning agents in hair care compositions.

In particular, there is no teaching that using heteroatom containing alkyl aldonamide compounds in hair care compositions alone or with, for example, anionic surfactants (e.g., sodium or ammonium salts of alkyl sulfates, alkyl ether sulfates), nonionic surfactants (e.g., alkyl polyoxyalkylene sorbitan esters or alkyl polyglycosides), amphoteric surfactants (e.g., alkyl carboxybetaines) and mixtures thereof, could result in a clear thickened hair care composition that foams copiously and leaves the hair soft, lustrous and manageable.

U.S. Pat. No. 2,662,073 to Mehltretter, et al. for example, teaches gluconamide compounds of the formula:

wherein R is an aliphatic hydrocarbon radical having 8 to 18 carbon atoms, a cycloaliphatic radical having 8 to 18 carbon atoms or a rosin radical. The compounds are said to be valuable wetting agents for use in the mercerization of cotton and in the manufacture of viscose yarn. There is clearly no teaching on suggestion of using heteroatom containing alkyl aldonamide compounds of the invention in liquid hair care compositions for improved foam, viscosity, clarity and conditioning benefits.

U.S. Pat. No 2,776,951 to Melamed teaches the preparation of vinyloxyethyl gluconamides as polymer precursors. The polymers are said to be useful as wetting agents and as paper, leather or textile finishing agents. There is clearly no teaching or suggestion of using heteroatom containing alkyl aldonamide compounds of the invention in liquid hair care compositions for improved foam, viscosity, clarity and conditioning benefits.

U.S. Pat. No. 2,721,211 to Buc teaches alkyl formyl phenylene gluconamides as solubilizing agents for vat dye stuffs. The alkyl formyl phenylene radical (R) of these compounds are structurally unrelated to the compounds of the invention which contain a hydrocarbon radical interrupted by a heteroatom. Also, U.S. Pat. No. 4,190,429 to Rutter, et al. teaches adamantyl gluconamides as antimicrobial agents. In both of these patents, there is clearly no teaching or suggestion of using heteroatom containing alkyl aldonamide compounds of the invention in liquid hair care compositions for improved foam, viscosity, clarity and conditioning benefits.

Fieser, et al. in J. Am. Chem. Soc. 78:2825 (1956) teaches the preparation of a series of N-alkyl arabinonamides and N-alkyl gluconamides for use as an emulsifying agents, where the attached aliphatic radical (R) is from $C_{10}$ to $C_{18}$. The reference teaches that such compounds are poor emulsifying agents and are therefore expected to be poor surfactants. Also, there is clearly no teaching or suggestion that the addition of oxygen or other heteroatoms in the alkyl radical can enhance the foam, viscosity, clarity and conditioning benefits in liquid hair care compositions.

Furthermore, the fact that the monosaccharide alkyl aldonamides, where the alkyl group is $C_{10}$ or greater, are poor emulsifiers is also recognized in German Pat. Nos. 2,321,752 and 2,338,087, both to Reiser, et al. (1975).

Specifically, DE 2,321,752 is directed to the preparation of N,N-dialkyl polyhydroxyamide compounds having the formula:

wherein n is 3 to 5; $R_1$ is hydrogen or a linear alkyl group containing 1 to 3 carbon atoms; and $R_2$ is an aliphatic hydrocarbon radical having 4 to 7 carbons in normal or branched arrangement (optionally interrupted by oxygen, sulfur or hydroxyl group). The principal patent DE 2,321,752, teaches that alkyl aldonamides having long chained radical (R) groups such as lauryl (12 carbons), cetyl (16 carbons) or stearyl (18 carbons), do not form stable water emulsions. Therefore, it was surprising to find that the liquid hair care compositions of the invention, which comprise heteroatom containing alkyl aldonamide compounds, provide clear compositions with improved foam, viscosity and conditioning benefits.

Japanese Patent 1-168653 again recognizes that the monosaccharide aldonamides of the art (e.g., N-alkyl gluconamides) do not show sufficient emulsifying properties (poor surface-activity). Again, there is a recognition that such compounds are poor emulsifiers and are therefore not expected to be useful as ingredients in liquid hair care compositions.

The Japanese patent seeks to address this problem by using N,N-dialkyl polyhydroxyamide compounds where one alkyl group (R) is $C_8$–$C_{18}$ and the other is $C_1$–$C_4$. There is clearly no teaching or suggestion of using heteroatom containing alkyl aldonamide compounds of the invention in liquid hair care compositions for improved foam, viscosity, clarity and conditioning benefits.

French Patent No. 2,523,962 to Monsigny teaches the compounds:

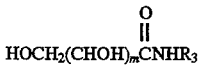

wherein m is 2 to 6 and $R_3$ is a linear or branched alkyl group containing 6 to 18 carbons. The patent further teaches polyoxyethylene, polyoxypropylene or polyglycerol derivatives of the formula. Again, however, there is no teaching of a hydrocarbon radical (R) when interrupted by a heteroatom, would provide liquid hair care compositions with improved foam, viscosity, clarity and conditioning benefits.

U.S. Pat. No. 4,973,473 to Schneider, et al. teaches skin treatment compositions in which the primary moisturizing agent may be a gluconamide compound. Methyloxypropyl gluconamide is the only example of this ingredient which has the formula:

Since this compound is clearly hydrophilic (not surface-active), it cannot be used as a foam stabilizer, viscosity modifier or conditioning agent. There is no suggestion to utilize alkyl chains greater than methyl and there is clearly no teaching or suggestion that aldonamides with interrupted long alkyl chains can provide improved foam, viscosity, clarity and conditioning benefits in liquid hair care compositions.

Schneider et al. in Hoppe-Seyler's Z. Physiol. Chem. 330:182 (1963) teaches alkyl gluconyl glycinate compounds having the formula:

wherein $R_4 = C_8$ to $C_{10}$

While this paper does teach monosaccharide aldonamides containing an alkyl group interrupted with an ester functionality, there is no teaching or suggestion that such alkyl groups may be interrupted with, for example, an ether, sulfide or amine or that the use of such groups will provide improved foam, viscosity, clarity and conditioning benefits in liquid hair care compositions.

Geyer in Chemische Berichte 97:2271 (1964) describes the preparation of N-alkanoyl-N-gluconoyl ethylene diamide compounds having the structure:

wherein $R_5 = C_{15}$, $C_6$; and Pfannemueller, et al. in Chemistry and Physics of Lipids 37:227 (1985) describes the preparation of N-alkanoyl-N-methyl-N'-gluconyl ethylene diamide compounds of the formula:

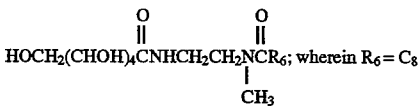

These references teach monosaccharide aldonamides containing an alkyl group that is interrupted with an amide group, not an amine group. Again, there is no teaching or suggestion of alkyl aldonamides with alkyl groups interrupted with an ether, sulfide or amine linkage or that such interrupting groups provide greater foam, viscosity, clarity and conditioning benefits than others. Furthermore, there is clearly no teaching or suggestion of using sugar compounds having two saccharide units or greater (e.g., lactobionamides) together within an interrupted alkyl group for providing improved foam, viscosity, clarity and conditioning benefits in liquid hair care compositions.

U.S. Pat. No. 5,037,973 to Meinetsbeger teaches a series of bis-alkyl aldonamide compounds as intermediates for pharmacological applications. While this paper does teach bis-alkyl aldonamide compounds containing heteroatoms, there is no teaching or suggestion that the use of such radicals will provide improved foam, viscosity, clarity and conditioning benefits in liquid hair care compositions. In addition, the heteroatom containing alkyl aldonamides of this invention are monomeric in nature (structurally very different) whereas the bis-alkyl aldonamide compounds of U.S. Pat. No. 5,037,973 are dimeric in nature and would not be considered as useful ingredients in liquid hair care compositions.

U.S. Pat. Nos. 3,766,367 and 3,855,290 to Zak, et al. as well as U.S. Pat. Nos. 4,038,294 and 4,342,706 to Conner, et al. teach quaternary halide gluconamide compounds of the formulas:

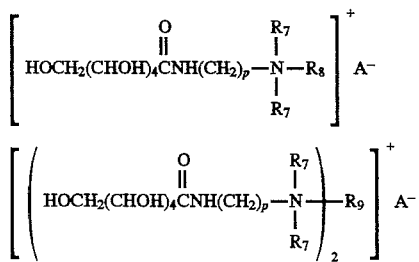

wherein;

$R_7 = C_1-C_2$, $CH_2CH_2OH$;

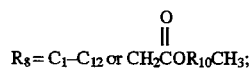

$R_9 = C_2-C_6$;
$p = 2-4$;
$A-=Cl-$, $Br-$ or $R_{11}C_6H_4SO_3-$
$q = 1-3$;
$R_{10} = C_7-C_{21}$; and
$R_{11} = H$, $CH_3$;

These compounds are said to be useful as emollients which are substantive to skin or hair and are further taught in U.S. Pat. Nos. 3,990,991 to Gerstein, 4,534,964 to Herstein et al. and 4,529,588 to Smith et al. which all describe conditioning shampoo compositions comprising quaternary halide gluconamide compounds. There is clearly no teaching or suggestion in any of these references, of using heteroatom containing alkyl aldonamide compounds of the invention in liquid hair care compositions for improved foam, viscosity, clarity and conditioning benefits. Also the heteroatom containing alkyl aldonamide compounds of the present invention are structurally very different and do not contain a quaternary ammonium functional group which is responsible for the emolliency and conditioning effect.

Finally, there are several references teaching the molecular and liquid crystal structure of alkyl aldonamides, see for example, J. Am. Chem. Soc. 109(11):3387 (1987), 110:2861 (1988) and 112:1768 (1990) to Fuhrhop, et al.; Mol. Cryst. Liq. Cryst. 135:93 (1986) to Baeyens-Volant, et al., 185:209 (1990) to Jeffery and 198:381 (1991) to Van Doren, et al.; Chemistry and Physics of Lipids 39:313 (1986) to Zabel, et al.; Liquid Crystals 1(4):357 (1986) and Makrolmol. Chem. 189:2433 (1988) to Pfannemueller, et al.; Carbohydrate Research 176:165 (1988) to Farnow, et al. and J. Am Chem. Soc. 113:7436 (1991) to Frankel, et al. There is clearly no teaching or suggestion in any of these references, of using heteroatom containing alkyl aldonamide compounds of the invention in liquid hair care compositions for improved foam, viscosity, clarity and conditioning benefits.

Alkyl Aldobionamides

U.S. Pat. Nos. 2,752,334 to Walton and 2,785,152 to Jones teach aldobionamide compounds prepared by the reaction of aldobionic acids or aldobionolactones with fatty amines or fatty amino acid esters. The compounds are said to be useful as an emulsifier in food compositions and as antimycotic agents. There is no teaching or suggestion that the use of a heteroatom (e.g., oxygen, nitrogen or sulfur) in the aliphatic hydrocarbon radical of an alkyl aldobionamide compound can improve foam, viscosity, clarity and conditioning benefits in liquid hair care compositions.

Williams, et al. in Archives of Biochem. and Biophysics, 195(1): 145 (1979) and Carbohydrate Research 67:C1–C3 (1978) teach aldobionamide compounds prepared by the reaction of aldobionic acids with alkyl amines. Again, there is no teaching or suggestion that the alkyl group of the alkyl amine may contain a heteroatom, nor is there any teaching or suggestion of using heteroatom containing alkyl aldobionamide compounds for enhanced foam, viscosity, clarity and conditioning benefits in liquid hair care compositions.

Scholnick, et al. in J. Dairy Sci. 63(3):471 (1980) teach aldobionamide compounds as effective chelating agents of ferric ion. There is clearly no teaching or suggestion of using heteroatom containing alkyl aldobionamide compounds of the invention in liquid hair care compositions for improved foam, viscosity, clarity and conditioning benefits.

In copending application, U.S. Ser. No. 816,419, the assignee of the subject application has filed an application directed to the use of the broad class of aldonamide surfactants in personal products or detergent compositions. The application, U.S. Ser. No. 981,644, has been filed as a separate application on the same date as U.S. Ser. No. 816,419. These applications have a few examples of using a heteroatom (i.e., ether and ester in the aliphatic hydrocarbon), however there is no teaching or suggestion that this heteroatom is responsible for improved foam, viscosity, clarity and conditioning benefits in hair care compositions. Also, U.S. Ser. No. 981,644 has been filed as world application WO 94/12511. On page 17 of WO 94/12511 it is mentioned, along with a broad recital of multiple product types, that aldonamide compounds may be used as surfactants in hair care compositions. There is absolutely no exemplification or teaching of the heteroatom containing alkyl aldonamide compounds of the invention in compositions with for example, certain essential ingredients such as cosurfactants, antidandruff agents, hair conditioning agents, suspending agents, auxiliary thickening agents, water and other auxilary agents (see claim 4). There is also clearly no teaching of improved foam, viscosity, clarity and conditioning benefits that are provided when heteroatom containing alkyl aldonamide compounds of the invention are formulated in hair care compositions. The individual ingredients have to fulfill, in part, wholly different functions while at the same time each ingredient must complement and increase the effect of other substances. This has always been a difficult challenge to meet and finding the right combination of ingredients for improved foam, viscosity, clarity and conditioning is a significant achievement.

Finally, there are several references teaching the molecular and micellar structure of alkyl aldobionamides generally, but are otherwise unrelated to the compounds of the invention, see for example, J. Phys. Chem. 93(4):1482 (1989) and Colloid Poylm. Sci. 268(6):513 (1990) to Denkinger, et al. and Polym. Bull. (Berlin) 6(5–6):305 (1982) to Emmerling.

Since most hair care compositions are based on petrochemical ingredients, it would be most desirable to use materials which are instead naturally derived, such as carbohydrates. These renewable raw materials have the distinct advantage of being readily available, inexpensive, biodegradable, aquatically favorable and optically pure.

Thus the ability to find a naturally derived, environmentally friendly compound, that simultaneously provides an enhanced copious persistent lather, thick viscosity, clarity and conditioning effect in clear liquid hair care compositions is a significant achievement.

Accordingly, it is an object of the present invention to provide hair care compositions that have excellent lathering and foaming characteristics.

It is another object of the present invention to provide hair care compositions that have stiff consistencies which allow effective bottle and tube packaging.

It is another object of the present invention to provide viscous hair care compositions which are resist to spillage and effectively cling to the hand before shampooing.

It is another object of the present invention to provide stable clear hair care compositions comprising of a heteroatom containing alkyl aidonamide compound which do not become turbid or produce sedimentation upon standing.

It is still another object of the present invention to provide mild hair care compositions that efficiently remove surface grease, dirt and skin debris from the hair shaft and scalp.

It is still another object of the present invention to provide new and improved hair care compositions that leave the hair fragrant, lustrous, soft, conditioned and in a manageable state.

It is a final object of the present invention to provide an improved method of shampooing and conditioning the hair. These and other objects will become readily apparent from the detailed description which follows.

SUMMARY OF THE INVENTION

The present invention provides new hair care compositions for use in home shampooing and conditioning operations. The present invention is based on the discovery that heteroatom containing alkyl aldonamide compounds pounds are useful as foam stabilizers, viscosity modifiers and conditioning agents in a variety of hair care compositions.

Included among the hair care compositions of the present invention are rinses, conditioners, shampoos, conditioning shampoos, antidandruff shampoos and the like. However, the conditioners, shampoos, conditioning shampoos and antidandruff shampoos are the preferred compositions and the components found in such compositions are described in the detailed description that follows.

DETAILED DESCRIPTION OF THE INVENTION

The present invention provides new hair care compositions that have improved foam, viscosity, clarity and conditioning characteristics due to the inclusion of a new type of alkyl aldonamide compound, specifically hereroatom containing alkyl aldonamide compounds of the formula:

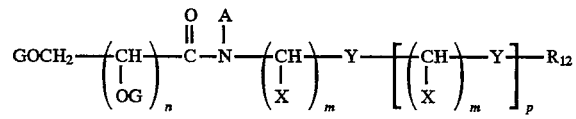

wherein:

$n = 1-6$;

$m = 1-5$;

$X = H$, a $C_1-C_4$ alkyl group or mixtures thereof;

$Y = NA$, $^+NH_2$, $^+NHA$, O, S, SO, $SO_2$,

or mixtures thereof;

$p = 0-25$ $G = H$, a mono-, di-, oligo-, polysaccharide group, a $(CH_2CH_2O)_q$—H, $(CH_2CHCH_3O)_r$—H group or mixtures thereof;

$q = 1-50$ $r = 1-50$ $A = H$, a hydroxy $C_1-C_{18}$ is alkyl group, $C_1-C_{18}$ straight or branched chain, saturated or unsaturated hydrocarbon which may be unsubstituted or substituted with an aromatic, cycloaliphatic, mixed aromatic aliphatic radical or a

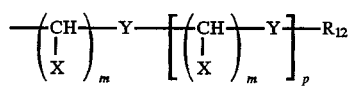

group or mixtures thereof; wherein X, m, Y and p are defined as above; and $R_{12}$ is a straight or branched chain, saturated or unsaturated hydrocarbon which may be unsubstituted or substituted with an aromatic, cycloaliphatic, or mixed aromatic aliphatic radical comprising one or more carbon atoms, preferably from about 1 to about 28 carbon atoms.

Preferably, $n = 2-5$;

$m = 1-4$;

$X = H$, a $C_1$ alkyl group or mixtures thereof;

$Y = NA$, $^+NH_2$, $^+NHA$, O,

or mixtures thereof;

$p = 0-8$ $G = H$, a monosaccharide group, a $(CH_2CH_2O)_q$—H, $(CH_2CHCH_3O)_r$—H group or mixtures thereof;

$q = 1-25$ $r = 1-25$ $A = H$, a hydroxy $C_1-C_8$ alkyl group, a $C_1-C_8$ straight or branched chain, saturated or unsaturated hydrocarbon group or mixtures thereof: and $R_{12}$ is a straight or branched chain, saturated or unsaturated hydrocarbon which may be unsubstituted or substituted with an aromatic, cycloaliphatic, or mixed aromatic aliphatic radical comprising from about 7 to about 24 carbon atoms.

Most preferably, n=3–5;

m=1–3;

X=H, a $C_1$ alkyl group or mixtures thereof;

Y=NA, $^+$NH$_2$, $^+$NHA, O,

or mixtures thereof;

p=0–6

G=H, a monosaccharide group, a $(CH_2CH_2O)_q$—H, $(CH_2CHCH_3O)_r$—H group or mixtures thereof;

q=1–15 r=1–15

A=H, a hydroxy $C_1$–$C_6$ alkyl group, a $C_1$–$C_6$ straight or branched chain, saturated or unsaturated hydrocarbon group or mixtures thereof; and $R_{12}$ is a straight or branched chain, saturated or unsaturated hydro carbon radical comprising from about 8 to about 22 carbon atoms.

A specific example of a monosaccharide hetero,atom containing alkyl aldonamide compound of the invention is $C_8/C_{10}$ oxypropyl D-gluconamide having the formula:

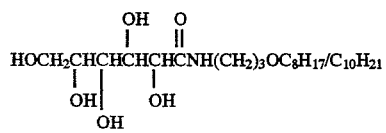

wherein:

n=4;

m=3;

X=hydrogen;

Y=oxygen (O);

p=0;

G=hydrogen;

A=hydrogen; and $R_{12}$=$C_6H_{13}$ (1%), $C_8H_{17}$ (59%), $C_{10}H_{21}$ (39%), $C_{12}H_{25}$ (1%).

Another specific example of a monosaccharide heteroatom containing alkyl aldonamide compound of the invention is $C_{12}$–$C_{15}$ oxypropylaminopropyl D-glucoheptonamide having the formula:

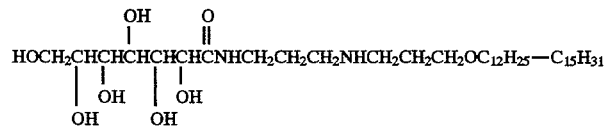

wherein:

n=5;

m=3;

X=hydrogen;

Y=oxygen (O) or nitrogen (NH);

p=1;

G=hydrogen;

A=hydrogen; and $R_{12}$=$C_{12}H_{25}$ (25%), $C_{13}H_{27}$ (39%), $C_{14}H_{29}$ (21%), $C_{15}H_{31}$ (15).

Yet another specific example of a monosaccharide heteroatom containing alkyl aldonamide compound of the invention is N-gluconyl dodecyldi(oxyethyl) glycinate, also known as N-gluconyl dodecyl(diethylene glycol) ether glycinate, N-gluconyl (diethylene glycol) monododecyl ether glycinate and as N-gluconyl dodecyl(dioxyethylene) glycinate having the formula:

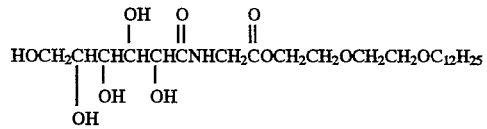

wherein:

n=4;

m=1 or 2;

X =hydrogen;

Y =ester (COO) or oxygen (O);

p=2;

G=hydrogen;

A=hydrogen; and $R_{12}$=$C_{12}H_{25}$.

A specific example of a disaccharide heteroatom containing alkyl aldonamide compound of the invention is dodecyloxypropyl D-lactobionamide having the formula:

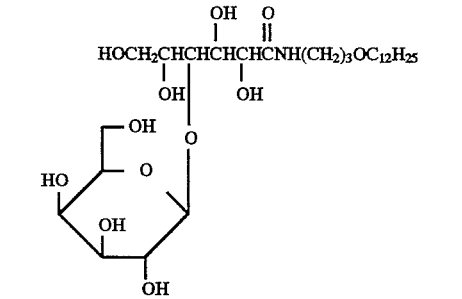

wherein:

n=4;

m=3;

X=hydrogen;

Y=oxygen (O);

p=0;

G=hydrogen or galactose;

A=hydrogen: and $R_{12}$=$C_{12}H_{25}$.

Another specific example of a disaccharide heteroatom containing alkyl aldonamide compound of the invention is dodecyltri(oxyethyl) oxypropyl D-glucopyranosyl-(1–5)-D-arabinonamide, also known as dodecyl (triethylene glycol) propylene glycol ether D-glucopyranosyl-(1–5)-D-arabinonamide, (triethylene glycol)propylene glycol monododecyl ether D-glucopyranosyl-(1–5)-D- arabinonamide and as dodecyl(trioxyethylene)oxypropylene D-glucopyranosyl-(1–5)-D-arabinonamide having the formula:

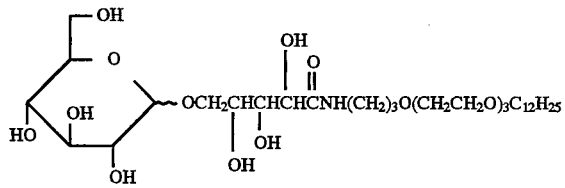

wherein:
n=3;
m=3 or 2;
X=hydrogen;
Y=oxygen (O);
p=3;
G=hydrogen or glucose;
A=hydrogen; and
$R_{12}=C_{12}H_{25}$.

D-Glucopyranosyl-(1–5)-D-arabinonic acid and its lactone are readily prepared from isomaltulose (also known as palatinose) by aqueous alkaline oxidation with oxygen or air [see DE-OS 3,248,404 (1982), EP 114,954 (1983), U.S. Pat. No. 4,618,715 (1986) and Chem. Abstr. 102, 7034x (1985) to Lichtenthaler et al.], and isomaltulose is obtained commercially by biochemical dehydrogenation of sucrose with Agrobacterium Tumefaciens [see Zuckerind. 115:20 (1990) to Buchholz et al.].

Other examples of compounds of the invention are set forth below:

alkyloxymethyl D-gluconamide
alkyloxyethyl D-gluconamide
alkyloxybutyl D-gluconamide
alkyloxypentyl D-gluconamide
alkyloxyethyloxymethyl D-gluconamide
alkyldi(oxyethyl)oxymethyl D-gluconamide
alkyldi(oxyethyl) D-gluconamide
alkyltri(oxyethyl) D-gluconamide
alkyltetra(oxyethyl) D-gluconamide
alkylpenta(oxyethyl) D-gluconamide
alkylhexa(oxyethyl) D-gluconamide
alkylhepta(oxyethyl) D-gluconamide
alkylocta(oxyethyl) D-gluconamide
alkyldi(oxypropyl) oxyethyl D-gluconamide
alkyltri(oxypropyl) oxyethyl D-gluconamide
alkylocta(oxypropyl)oxyethyl D-gluconamide
alkyldi(oxyethyl)oxypropyl D-gluconamide
alkyltri(oxyethyl)oxypropyl D-gluconamide
alkyltetra(oxyethyl)oxypropyl D-gluconamide
alkylpenta(oxyethyl)oxypropyl D-gluconamide
alkylhexa(oxyethyl)oxypropyl D-gluconamide
alkylhepta(oxyethyl)oxypropyl D-gluconamide
alkylocta(oxyethyl) oxypropyl D -gluconamide
alkyloxymethyl D-lactobionamide
alkyloxyethyl D-lactobionamide
alkyloxybutyl D-lactobionamide
alkyloxypentyl D-lactobionamide
alkyl(oxyethyl)oxymethyl D-lactobionamide
alkyldi(oxyethyl)oxymethyl D-lactobionamide
alkyldi(oxyethyl) D-lactobionamide
alkyltri(oxyethyl) D-lactobionamide
alkyltetra(oxyethyl) D-lactobionamide
alkylpenta(oxyethyl) D-lactobionamide
alkylhexa(oxyethyl) D-lactobionamide
alkylhepta(oxyethyl) D-lactobionamide
alkylocta(oxyethyl) D-lactobionamide
alkyldi(oxypropyl)oxyethyl D-lactobionamide
alkyltri(oxypropyl)oxyethyl D-lactobionamide
alkylocta(oxypropyl)oxyethyl D-lactobionamide
alkyldi(oxyethyl)oxypropyl D-lactobionamide
alkyltri(oxyethyl)oxypropyl D-lactobionamide
alkyltetra(oxyethyl)oxypropyl D-lactobionamide
alkylpenta(oxyethyl)oxypropyl D-lactobionamide
alkylhexa(oxyethyl)oxypropyl D-lactobionamide
alkylhepta(oxyethyl)oxypropyl D-lactobionamide
alkylocta(oxyethyl)oxypropyl D-lactobionamide
alkyloxyethyl D-maltobionamide
alkyloxyethyloxymethyl D-maltobionamide
alkylhexa(oxyethyl) D-maltobionamide
alkyloxyethyl D-glucoheptonamide
alkyloxyethyl D-melibionamide
alkyloxyethyl D-cellobionamide
alkyloxyethyl D-gentiobionamide
alkyloxyethyl D-glucopyranosyl-(1–5)-D-arabinonamide
N-gluconyl alkyl(oxyethyl) glycinate
N-gluconyl alkyltri(oxyethyl) glycinate
N-gluconyl alkyltetra(oxyethyl) glycinate
N-gluconyl alkyltri(oxyethyl) N-methylglycinate
N-gluconyl dialkyldi(oxyethyl) aspartate
N-gluconyl alkyldi(oxyethyl) alaninate
N-gluconyl alkyltetra(oxyethyl) β-alaninate
N-gluconyl alkyldi(oxypropyl) N-methylalaninate
N-gluconyl alkyltri(oxyethyl) α-aminobutyrate
N-gluconyl alkyl(oxyethyl) sarcosinate
N-gluconyl alkyldi(oxyethyl) sarcosinate
N-gluconyl alkyltri(oxyethyl) sarcosinate
N-gluconyl alkyltri(oxyethyl) leucinate
N-lactobionyl alkyldi(oxyethyl) glycinate
N-lactobionyl alkyltri(oxyethyl) alaninate
N-lactobionyl alkyltetra(oxyethyl) β-alaninate
N-lactobionyl alkyldi(oxyethyl) N-methylalaninate
N-lactobionyl alkyltri(oxyethyl) α-aminobutyrate
N-lactobionyl alkyltri(oxyethyl) α-aminoisobutyrate
N-lactobionyl alkyltri(oxyethyl) ε-aminocarproate
N-lactobionyl alkyldi(oxyethyl) sarcosinate
N-lactobionyl alkyltri(oxyethyl) leucinate
N-glucoheptonyl alkyl(oxyethyl) glycinate
N-maltobionyl alkyl(oxyethyl) glycinate
N-cellobionyl alkyl(oxyethyl) glycinate
alkyloxypropyl D-gluconamide monooxyethylene ether
alkyloxypropyl D-gluconamide dioxyethylene ether
alkyloxypropyl D-gluconamide trioxyethylene ether
alkyloxypropyl D-gluconamide tetraoxyethylene ether
alkyloxypropyl D-gluconamide pentaoxyethylene ether
alkyloxypropyl D-gluconamide hexaoxyethylene ether alkyloxypropyl D-gluconamide heptaoxyethylene ether
alkyloxypropyl D-gluconamide octaoxyethylene ether
alkyloxypropyl D-gluconamide nonaoxyethylene ether
alkyloxypropyl D-gluconamide decaoxyethylene ether
alkyloxypropyl D-gluconamide trioxypropylene ether
alkyloxypropyl D-gluconamide oxyethylenedioxypropylene ether
alkyloxyethyl D-gluconamide dioxyethylenetrioxypropylene ether
alkyloxyethyl D-gluconamide trioxypropylenedioxyethylene ether
alkyloxypropyl D-lactobionamide monooxyethylene ether
alkyloxypropyl D-lactobionamide dioxyethylene ether
alkyloxypropyl D-lactobionamide trioxyethylene ether
alkyloxypropyl D-lactobionamide tetraoxyethylene ether
alkyloxypropyl D-maltobionamide dioxyethylene ether
alkyloxypropyl D-maltobionamide pentaoxypropylene ether
alkyloxypropyl D-maltobionamide decaoxypropylene ether Wherein the alkyl group contains from about 1 to about 28 carbon atoms, preferably from about 7 to about 24 carbon atoms and even more preferably from about 8 to about 22 carbon atoms.

The A group is preferably hydrogen, although it may be a hydroxy $C_1$–$C_4$ alkyl group or a $C_1$ to $C_{18}$ straight or branched chain, saturated or unsaturated hydrocarbon radical. The A group may also be interrupted by a hetero-atom and may have the same structure as the group attached to the nitrogen atom.

If the A or $R_{12}$ group is an aliphatic radical, suitable examples include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, coco, soya, tallow, tall oil, castor, corn, cottonseed, palm, rapeseed, safflower, sesame, sunflower, fish oil, allyl, octenyl, nonenyl, decenyl, undecenyl, dodecenyl, tridecenyl, tetradecenyl, pentadecenyl, hexadecenyl, heptadecenyl, octadecenyl (oleyl), linoleyl and linolenyl.

If the A or $R_{12}$ group is interrupted by an aromatic radical, the aromatic group may be for example, benzyl or aniline. Cycloaliphatic radicals are exemplified but are not limited to cyclopentyl and cyclohexyl. Suitable mixed aromatic aliphatic radicals are exemplified by benzylpropyl, phenylethyl, phenoxyethyl and vinylbenzyl.

The G group may be hydrogen or an attached mono-, di-, oligo-, or polysaccharide. Examples of suitable saccharides that can be oxidized to sugar acids [GOCH$_2$(CHOG)$_n$COOH] include but are not limited to, erythrose, threose, ribose, arabinose, xylose, lyxose, allose, altrose, idose, talose, glucose, galactose, mannose, gulose, fructose, sorbose, sucrose, isomaltose, isomalt, isomaltulose (palatinose), trehalulose, 3-ketosucrose, leucrose, lactulose, gentiobiose, maltose, lactose, melibose, cellobiose, triglucose, tetraglucose, starch and cellulose.

When an amino group is present it may be converted to the corresponding salt by reaction with, for example an organic or inorganic acid such as hydrochloric acid, sulfuric acid, phosphoric acid, boric acid, oxalic acid, malonic acid, glutaric acid, adipic acid, sebacic acid, tricarballylic acid, butanetetracarboxylic acid, itaconic acid, maleic acid, malic acid, fumaric acid, citraconic acid, glutaconic acid, bis (hydroxymethyl)propionic acid, tartaric acid, citric acid, formic acid, lactic acid, acetic acid, benzoic acid, methanesulfonic acid, ethanesulfonic acid, toluenesulfonic acid and mixtures thereof or by reaction with, for example an alkylating agent such as chloromethane, dimethyl sulfate, diethyl sulfate and benzyl chloride.

The presence of an amino group, or a salt of an amino group in the alkyl chain of a heteroatom containing alkyl aldonamide compound of the present invention, provides a functionality that is substantive to the hair. The final result is a conditioning effect which provides desirable qualities such as ease of combing, detangling, body, shine, texture, split-end mending, manageability and static buildup prevention.

The heteroatom containing alkyl aldonamide compounds of the present invention can also be ethoxylated, propoxylated or butoxylated with ethylene oxide, propylene oxide, butylene oxide or mixtures thereof to give a series of polyoxyalkylene ether sugar surfactants.

Typical levels of heteroatom containing alkyl aldonamide compound are from about 0.1% to about 40%, preferably from about 0.2% to about 35%, even more preferably from about 0.3% to about 30% by weight of the composition.

There are a wide variety of essential ingredients that can be used in hair care compositions depending on the characteristics and end purpose sought. Such ingredients are well known to those skilled in the art and include, but are not limited to cosurfactants, antidandruff agents, hair conditioning agents, suspending agents, auxiliary thickening agents, water and other optional ingredients (auxilary agents).

The individual ingredients have to fulfill, in part, wholly different functions while at the same time each ingredient must complement and increase the effect of other substances. This has always been a difficult challenge to meet and finding the right combination of ingredients for improved foam, viscosity, clarity and conditioning is a significant achievement.

COMPOSITIONS

The essential and optional ingredients of the present invention are given in the following paragraphs.

Cosurfactants (Cleansing Agents)

An essential component of the present invention is a cosurfactant. The term "cosurfactant" is used to denote both soap and nonsoap surface-active agents. The nonsoap surface-active agents include anionic, nonionic, amphoteric, zwitterionic and cationic surfactants.

Soaps

Suitable soaps are exemplified as alkali metal, ammonium or alkanolammonium salts of aliphatic alkane or alkene monocarboxylic acids having about 8 to about 18 carbon atoms. Sodium, potassium, ammonium, mono-, di-, and triethanolammonium cations or combinations thereof, are preferred. Soaps may be prepared by either direct saponification of fats and oils or by neutralization of free fatty acids. Particularly useful are the sodium, potassium, ammonium and alkanolammonium salts of lauric acid, myristic acid, palmitic acid, stearic acid, oleic acid, linoleic acid, ricinoleic acid, coconut fatty acid and tallow fatty acid.

Anionic Surfactants

Suitable anionic surfactants are broadly exemplified as alkali metal, ammonium or alkanolammonium salts of organic reaction products having an aliphatic alkyl, alkene or alkyl aromatic group with about 8 to about 18 carbon atoms and at least one water solubilizing radical selected from the group consisting of phosphate, phosphonate, sulfonate, sulfate or carboxylate. Examples of suitable anionic surfactants useful in the present invention include the sodium, potassium, ammonium, mono-, di- and triethanolammonium salts of; $C_8$–$C_{18}$ alkyl phosphates, $C_8$–$C_{18}$ alkyl ether phosphates with about 1 to about 25 moles of alkylene oxide, $C_8$–$C_{18}$ acyl isethionates, $C_8$–$C_{18}$ acyl ether isethionates with about 1 to about 25 moles of alkylene oxide, $C_8$–$C_{18}$ acyl taurinates, $C_8$–$C_{18}$ acyl ether taurinates with about 1 to about 25 moles of alkylene oxide, $C_8$–$C_{18}$ alkyl benzene sulfonates, $C_8$–$C_{18}$ alkyl ether benzene sulfates with about 1 to about 25 moles of alkylene oxide, $C_8$–$C_{18}$ alkyl paraffin sulfonates (primary and secondary), $C_8$–$C_{18}$ alkanolamide sulfates, $C_8$–$C_{18}$ alkanolamide ether sulfates with about 1 to about 25 moles of alkylene oxide, $C_8$–$C_{18}$ alkyl $\alpha$-sulfomonocarboxylates, $C_8$–$C_{18}$ alkyl glyceryl sulfates, $C_8$–$C_{18}$ alkyl glyceryl ether sulfates with about 1 to about 25 moles of alkylene oxide, $C_8$–$C_{18}$ alkyl glyceryl sulfonates, $C_8$–$C_{18}$ alkyl glyceryl ether sulfonates with about 1 to about 25 moles of alkylene oxide, $C_8$–$C_{18}$ alkyl ether methylcarboxylates with about 1 to about 25 moles of alkylene oxide, $C_8$–$C_{18}$ alkyl sarcosinates/glycinates/hydrolysates, $C_8$–$C_{18}$ monoalkyl sulfosuccinates, $C_8$–$C_{18}$ monoalkyl sulfosuccinamates, $C_5$–$C_{10}$ dialkyl sulfosuccinates, $C_5$–$C_{10}$ dialkyl sulfosuccinamates, $C_8$–$C_{18}$ $\alpha$-olefin sulfonates, $C_8$–$C_{18}$ alkyl sulfates and $C_8$–$C_{18}$ alkyl ether sulfates with about 1 to about 25 moles of alkylene oxide.

Description of Anionic Surfactants

The sodium, potassium and ammonium salts of alkyl phosphates and alkyl ether phosphates having about 8 to about 18 carbon atoms and about 1 to about 25 moles of alkylene oxide represent a suitable class of anionic surfactant useful in the present invention. Alkyl phosphates and alkyl ether phosphates are prepared by reacting $C_8$–$C_{18}$ alkyl fatty alcohols, $C_8$–$C_{18}$ alkyl fatty alcohol alkoxylates or $C_8$–$C_{18}$ alkyl phenol alkoxylates with either phosphorous pentoxide, phosphorous oxychloride, phosphoric acid or polyphosphoric acid to give a mixture of monoalkyl and dialkyl phosphate esters that may be neutralized with base. Preferred alkyl ether phosphates are those comprising an average alkyl chain length of about 10 to about 16 carbon atoms and an average degree of alkoxylation of about 1 to about 16 moles of ethylene oxide, propylene oxide or mixtures thereof. Specific examples of alkyl phosphate esters and alkyl ether phosphates useful in the present invention include sodium dodecyl phosphate, ammonium dodecyl phosphate, ammonium tetradecyl phosphate, sodium $C_{10}$–$C_{16}$ alkyl phosphate, sodium dodecyl (diethylene glycol) ether phosphate, sodium tetradecyl (triethylene glycol) ether phosphate, PPG-5 ceteth-10 phosphate, oleth-10 phosphate and mixtures thereof.

The sodium, potassium and ammonium salts of alkyl isethionates, alkyl ether isethionates, alkyl taurinates and alkyl ether taurinates having about 8 to about 18 carbon atoms and about 1 to about 25 moles of alkylene oxide represent another suitable class of anionic surfactant useful in the present invention. Alkyl isethionates, alkyl ether isethionates, alkyl taurinates and alkyl ether taurinates are prepared by reacting $C_8$–$C_{18}$ alkyl fatty acids, $C_8$–$C_{18}$ alkyl fatty acid halides, $C_8$–$C_{18}$ alkyl ether $C_1$–$C_3$ alkylcarboxylic acids or $C_8$–$C_{18}$ alkyl ether $C_1$–$C_3$ alkylcarboxylic acid halides with either the sodium, potassium or ammonium salts of isethionate, polyoxyalkylene isethionate, taurine, polyoxyalkylene taurine, N-methyl taurine or polyoxyalkylene N-methyl taurine. Preferred alkyl ether isethionates and alkyl ether taurinates are those comprising an average alkyl chain length of about 10 to about 16 carbon atoms and an average degree of alkoxylation of about 1 to about 6 moles of ethylene oxide. Specific examples of alkyl isethionates, alkyl ether isethionates, alkyl taurinates and alkyl ether taurinates useful in the present invention include sodium dodecyl isethionate, potassium dodecyl isethionate, ammonium dodecyl isethionate, sodium tetradecyl isethionate, ammonium tetradecyl isethionate, sodium coconut isethionate, ammonium coconut isethionate, sodium dodecyl (ethylene glycol) ether isethionate, sodium coconut (diethylene glycol) ether isethionate, sodium dodecyl taurinate, sodium coconut(ethylene glycol) ether taurinate, sodium dodecyl N-methyl taurinate, ammonium dodecyl N-methyl taurinate, sodium tetradecyl N-methyl taurinate, sodium coconut N-methyl taurinate, ammonium coconut N-methyl taurinate, sodium tetradecyl(ethylene glycol) ether taurinate, ammonium coconut(triethylene glycol) ether N-methyl taurinate and mixtures thereof.

Another suitable class of anionic surfactant useful in the present invention are the sodium, potassium and ammonium salts of alkyl benzene sulfonates in which the alkyl group contains from about 8 to about 18 carbon atoms in branched or preferably in straight chain configuration. Alkyl benzene sulfonates are prepared by sulfonation of linear $C_8$–$C_{18}$ alkyl benzenes with sulfur trioxide in a falling film or tube bundle reactor followed by neutralization with base. Other suitable sulfonating agents used to prepare $C_8$–$C_{18}$ alkyl benzene sulfonates include oleum, chlorosulfonic acid, sulfuric acid or sulfur trioxide complexes. Examples of suitable alkali metal, ammonium and alkanolammonium salts of alkyl benzene sulfonates are disclosed in U.S. Pat. Nos. 2,220,099 and 2,477,383 both of which are incorporated herein by reference. Specific examples of alkyl benzene sulfonates useful in the present invention include sodium dodecyl benzene sulfonate, potassium dodecyl benzene sulfonate, ammonium dodecyl benzene sulfonate, sodium $C_{11}$–$C_{13}$ alkyl benzene sulfonate, sodium tetradecyl benzene sulfonate, ammonium tetradecyl benzene sulfonate and mixtures thereof.

Another suitable class of anionic surfactant useful in the present invention are the sodium, potassium and ammonium salts of alkyl benzene ether sulfates in which the alkyl group contains from about 8 to about 18 carbon atoms in branched or preferably in straight chain configuration with about 1 to about 25 moles of alkylene oxide. Alkyl benzene ether sulfates are prepared by sulfation of linear $C_8$–$C_{18}$ alkyl phenol alkoxylates with sulfur trioxide, oleum, chlorosulfonic acid, sulfuric acid or sulfur trioxide complexes followed by neutralization with base. Preferred alkyl benzene ether sulfates are those comprising an average alkyl chain length of about 10 to about 16 carbon atoms and an average degree of alkoxylation of about 1 to about 6 moles of ethylene oxide. Specific examples of alkyl benzene ether sulfates useful in the present invention include sodium nonylphenol(diethylene glycol) ether sulfate, sodium nonylphenol(triethylene glycol) ether sulfate, sodium dinonylphenol(triethylene glycol) ether sulfate, sodium dodecylphenol(tetraethylene glycol) ether sulfate, ammonium dodecylphenol(diethylene glycol) ether sulfate and mixtures thereof.

Still another suitable class of anionic surfactant useful in the present invention are the sodium, potassium and ammonium salts of paraffin sulfonates having about 8 to about 18 carbon atoms, more desirably from about 12 to about 16 carbon atoms. Paraffin sulfonates are preferably prepared by sulfoxidation of a specific cut of paraffin with sulfur dioxide and oxygen. The product consists mainly of secondary sulfonic acids along with some primary sulfonic acids which are neutralized with a suitable base to provide a water soluble paraffin sulfonate. Similarly, paraffin sulfonates may also be obtained by sulfochlorination which utilizes a mixture of sulfur dioxide, chlorine and actinic light as the sulfonating agent. It is most desirable to prepare paraffin sulfonates as the monosulfonate, having no unreacted starting paraffin hydrocarbon (or having a limited portion thereof present) and little or no inorganic salt by-product. Similarly the proportions of disulfonate or higher sulfonate should be minimized, although some may be present. Specific examples of paraffin sulfonate useful in the present invention include sodium $C_{12}$–$C_{13}$ paraffin sulfonate, sodium $C_{12}$–$C_{14}$ paraffin sulfonate, sodium $C_{12}$–$C_{15}$ paraffin sulfonate, sodium $C_{13}$–$C_{15}$ paraffin sulfonate potassium $C_{12}$–$C_{15}$ paraffin sulfonate, ammonium $C_{13}$–$C_{15}$ paraffin sulfonate, sodium $C_{12}$–$C_{16}$ paraffin sulfonate and mixtures thereof.

Still another suitable class of anionic surfactant, useful in the present invention are the sodium, potassium and ammonium salts of alkanolamide sulfates and alkanolamide ether sulfates having about 8 to about 18 carbon atoms with about 1 to about 25 moles of alkylene oxide. Alkanolamide sulfates and alkanolamide ether sulfates are prepared by sulfating $C_8$–$C_{18}$ alkanolamides or $C_8$–$C_{18}$ alkanolamide alkoxylates with sulfur trioxide, oleum, chlorosulfonic acid, sulfuric acid or sulfur trioxide complexes followed by neutralization with base. Specific examples of alkanolamide sulfates and alkanolamide ether sulfates useful in the present invention include sodium dodecyl monoethanolamide sulfate, sodium tetradecyl diethanolamide monosulfate, sodium tetradecyl diethanolamide disulfate, sodium coconut monoethanolamide sulfate, ammonium coconut diethanolamide monosulfate, sodium coconut diethanolamide sesquisulfate, sodium coconut monoethanolamide (diethylene glycol) ether sulfate, sodium coconut monoethanolamide(triethylene glycol) ether sulfate and mixtures thereof.

Still another suitable class of anionic surfactant useful in the present invention are the sodium, potassium and ammonium salts of alkyl α-sulfomonocarboxylates having about 8 to about 18 carbon atoms. Alkyl α-sulfomonocarboxylates monocarboxylates are prepared by sulfonation of $C_8$–$C_{18}$ alkyl fatty acids, $C_8$–$C_{18}$ alkyl fatty acid esters with sulfur trioxide, oleum, chlorosulfonic acid, sulfuric acid or sulfur trioxide complexes followed by neutralization with base; or by esterification of sulfoacetic acid, α-sulfopropionic acid or α-sulfobutyric acid with higher $C_8$–$C_{18}$ alkyl alcohols followed by neutralization with base. Specific examples of alkyl α-sulfomonocarboxylates useful in the present invention include sodium methyl α-sulfolaurate, potassium ethyl α-sulfolaurate, sodium methyl α-sulfomyristate, ammonium ethyl α-sulfomyristate, sodium decyl α-sulfobutyrate, sodium dodecyl sulfoacetate, sodium coconut sulfoacetate, ammonium dodecyl α-sulfopropionate and mixtures thereof.

Still another suitable class of anionic surfactant useful in the present invention are the sodium, potassium and ammonium salts of alkyl glyceryl sulfates and alkyl glyceryl ether sulfates having about 8 to about 18 carbon atoms and about 1 to about 25 moles of alkylene oxide. Alkyl glyceryl sulfates and alkyl glyceryl ether sulfates are prepared by sulfation of $C_8$–$C_{18}$ alkyl monoglycerides, $C_5$–$C_{14}$ dialkyl glycerides, $C_8$–$C_{18}$ alkyl monoglyceride alkoxylates. fats or oils with sulfuric acid. Suitable examples of fats and oils include coconut, soya, tallow, castor, corn, cottonseed, palm, rapeseed, safflower, sesame, sunflower, fish, and tall oil. Preferred alkyl glyceryl ether sulfates are those comprising an average chain length of about 10 to about 16 carbon atoms and an average degree of alkoxylation of about 1 to about 6 moles of ethylene oxide. Specific examples of alkyl glyceryl sulfates useful in the present invention include sodium dodecyl glyceryl sulfate, potassium dodecyl glyceryl sulfate. ammonium dodecyl glyceryl sulfate, sodium tetradecyl glyceryl sulfate, ammonium oleyl glyceryl sulfate, ammonium tetradecyl glyceryl sulfate, sodium coconut glyceryl sulfate, sodium coconut(ethylene glycol) glyceryl ether sulfate, sodium coconut(diethylene glycol) glyceryl ether sulfate, sodium coconut(triethylene glycol) glyceryl ether sulfate and mixtures thereof.

Still another suitable class of anionic surfactant useful in the present invention are the sodium, potassium and ammonium salts of alkyl glyceryl sulfonates and alkyl glyceryl ether sulfonates having about 8 to about 18 carbon atoms and about 1 to about 25 moles of alkylene oxide. Alkyl glyceryl sulfonates and alkyl glyceryl ether sulfonates are prepared by the Strecker reaction of a higher $C_8$–$C_{18}$ alkyl chlorohydrin ether or $C_8$–$C_{18}$ alkyl polyoxyalkylene chlorohydrin ether with alkali sulfite, alkali bisulfite or analogous type salt. Preferred alkyl glyceryl sulfonates are those comprising an average chain length of about 10 to about 16 carbon atoms and an average degree of alkoxylation of about 1 to about 6 moles of ethylene oxide. Specific examples of alkyl glyceryl sulfonates useful in the present invention include sodium dodecyl glyceryl sulfonate, potassium dodecyl glyceryl sulfonate, ammonium dodecyl glyceryl sulfonate, sodium tetradecyl glyceryl sulfonate, ammonium oleyl glyceryl sulfonate, ammonium tetradecyl glyceryl sulfonate, sodium coconut glyceryl sulfonate, sodium coconut(ethylene glycol) glyceryl ether sulfonate, sodium coconut(diethylene glycol) glyceryl ether sulfonate, sodium coconut(triethylene glycol) glyceryl ether sulfonate and mixtures thereof.

Still another suitable class of anionic surfactant useful in the present invention are the sodium, potassium and ammonium salts of alkyl ether methylcarboxylates having about 8 to about 18 carbon atoms and about 1 to about 25 moles of alkylene oxide. Alkyl ether methylcarboxylates are prepared by carboxymethylating the condensation products of alkylene oxide and higher $C_8$–$C_{18}$ alkyl alcohols with halo-acetic acid salts or by chemical oxidation. The alcohols can be derived synthetically or naturally from fats or oils. Dodecyl alcohol, tetradecyl alcohol and coconut oil are preferred herein. Such alcohols are reacted with about 1 to about 25 moles of alkylene oxide followed by carboxymetoxide and neutralization with base. Preferred alkyl ether methylcarboxylates are those comprising an average alkyl chain length of about 10 to about 16 carbon atoms and an average degree of alkoxylation of about 1 to about 15 moles of ethylene oxide, propylene oxide or mixtures thereof. Specific examples of alkyl ether methylcarboxylates useful in the present invention include sodium dodecyl ether methylcarboxylate, sodium dodecyl(ethylene glycol) ether methylcarboxylate, sodium dodecyl(diethylene glycol) ether methylcarboxylate, ammonium dodecyl(triethylene glycol) ether methylcarboxylate, sodium tetradecyl(triethylene glycol) ether methylcarboxylate, sodium tetradecyl(tetraethylene glycol) ether methylcarboxylate, trideceth-7 carboxylate, laureth-13 carboxylate and mixtures thereof.

Still another suitable class of anionic surfactant useful in the present invention are the sodium, potassium, ammonium and alkanolammonium salts of alkyl sarcosinates having about 8 to about 18 carbon atoms. Alkyl sarcosinates are generally considered to be acylated amino acid salts prepared by amidation of $C_8$–$C_{18}$ alkyl fatty acids, $C_8$–$C_{18}$ alkyl fatty acid esters or $C_8$–$C_{18}$ alkyl fatty acid halides with an amino acid sarcosine salt. Specific examples of alkyl sarcosinates useful in the present invention include sodium dodecyl sarcosinate, potassium dodecyl sarcosinate, ammonium dodecyl sarcosinate, sodium tetradecyl sarcosinate, ammonium tetradecyl sarcosinate, sodium coconut sarcosinate, ammonium coconut sarcosinate, triethanolamine oleyl sarcosinate and mixtures thereof. Examples of other suitable acylated amino acid salts useful in the present invention include the sodium, potassium and ammonium salts of $C_8$–$C_{18}$ alkyl alaninate, $C_8$–$C_{18}$ alkyl β-alaninate, $C_8$–$C_{18}$ alkyl N-methyl alaninate, $C_8$–$C_{18}$ alkyl α-aminoisobutyrate, $C_8$–$C_{18}$ alkyl α-aminobutyrate, $C_8$–$C_8$ alkyl α-aminocaproicate, $C_8$–$C_{18}$ alkyl glycinate, $C_8$–$C_{18}$ alkyl N-ethyl glycinate, $C_8$–$C_{18}$ alkyl N-propyl glycinate, $C_8$–$C_{18}$ alkyl N-butyl glycinate, $C_8$–$C_{18}$ alkyl leucinate, $C_8$–$C_{18}$ alkyl methioninate, $C_8$–$C_{18}$ alkyl serinate, $C_8$–$C_{18}$ alkyl dlnorvalinate, $C_8$–$C_{18}$ alkyl aspartate, $C_8$–$C_{18}$ alkyl glutamate and mixtures thereof. Preferred acylated amino acid salts useful in the present invention include the sodium, potassium and ammonium salts of dodecyl, tetradecyl and coconut glycinate, sarcosinate and mixtures thereof. Besides amidating amino acids salts, mixtures of amino acids or polypeptides, obtained by hydrolyzing proteins, may be amidated with $C_8$–$C_{18}$ alkyl fatty acids, $C_8$–$C_{18}$ alkyl fatty acid esters or $C_8$–$C_{18}$ alkyl fatty acid halides. Suitable examples of hydrolyzable proteins include collagen, corn, keratin, silk, soy, scrapleather, wheat gluten and albumin. Preferred polypeptide amino acid salts useful in the present invention include the sodium, potassium and ammonium salts of dodecyl, tetradecyl, coconut and oleyl leather hydrolysate or collagen hydrolysate (animal protein).

Yet another suitable class of anionic surfactant useful in the present invention are the sodium, potassium and ammonium salts of alkyl or dialkyl sulfosuccinates and sulfosuccinamates having from ,about 8 to about 18 carbon atoms. Alkyl sulfosuccinates and sulfosuccinamates are prepared by the reaction of maleic anhydride, maleic and/or fumaric acid with one or two equivalents of an appropriate reactive moiety containing a labile hydrogen, followed by sulfonation with sodium bisulfite, sodium sulfite, sodium metabisulfite or analogous type salt. Suitable examples of appropriate labile reactants are the $C_8$–$C_{18}$ alkyl fatty amines, $C_8$–$C_{18}$ alkyl fatty alcohols, $C_8$–$C_{18}$ alkyl fatty alcohol alkoxylates, $C_8$–$C_{18}$ alkyl fatty amides, $C_8$–$C_{18}$ alkyl fatty alkanolamides and $C_8$–$C_{18}$ alkyl fatty alkanolamide alkoxylates. Preferred are the alkyl sulfosuccinates, particularly sodium dioctyl sulfosuccinate, disodium dodecyl sulfosuccinate, diammonium tetradecyl sulfosuccinate, disodium dodecyl(diethylene glycol) ether sulfosuccinate, disodium coconut(triethylene glycol) ether sulfosuccinate, disodium undecylenamido MEA sulfosuccinate, disodium laurethsulfosuccinate, disodium lauramido MEA sulfosuccinate, disodium cocoamidosulfosuccinate, disodium cocoamido MIPA sulfosuccinate, disodium oleamido MEA sulfosuccinate, disodium oleamido PEG-2 sulfosuccinate, disodium oleamidosulfosuccinate, disodium cocoamido(tetraethylene glycol) ether sulfosuccinate, disodium ricinoleyl MEA sulfosuccinate and mixtures thereof.

Yet another suitable class of anionic surfactant useful in the present invention are the sodium, potassium and ammonium salts of α-olefin sulfonates having about 8 to about 18 carbon atoms. α-Olefin sulfonates are prepared by continuous sulfonation of 1-alkenes with liquid or gaseous sulfur trioxide. The 1-alkenes are derived from oligomerization of ethylene or from thermocracking of certain hydrocarbons. Suitable examples of 1-alkenes include 1-dodecene, 1-tetradecene and 1-hexadecene. The sulfonation of 1-alkenes results in a fairly complex mixture of products comprised of alkene sulfonate, hydroxyalkane sulfonate and alkyl disulfonate in a ratio of about (60–70):(20–30):(4–12) respectively. Preferred α-olefin sulfonates are those comprising a mixture of individual compounds having an average chain length of about 12 to about 16 carbon atoms. Such mixtures can comprise from about 0% to about 30% by weight $C_{12}$ olefin sulfonate, from about 55% to about 75% by weight $C_{14}$ olefin sulfonate and from about 25% to about 45% by weight $C_{16}$ olefin sulfonate. Specific examples of α-olefin sulfonates useful in the present invention include sodium $C_{12}$–$C_{13}$ α-olefin sulfonate, sodium $C_{12}$–$C_{14}$ α-olefin sulfonate, sodium $C_{13}$–$C_{14}$ α-olefin sulfonate, sodium $C_{13}$–$C_{15}$ α-olefin sulfonate, sodium $C_{12}$–$C_{16}$ α-olefin sulfonate, potassium $C_{12}$–$C_{16}$ α-olefin sulfonate, ammonium $C_{12}$–$C_{16}$ α-olefin sulfonate and mixtures thereof. Further examples of α-olefin sulfonates are described more fully in U.S. Pat. No. 3,332,880 which is incorporated herein by reference.

A preferred class of anionic surfactant found to be useful in the present invention are the sodium, potassium and ammonium salts of alkyl sulfates, especially those obtained by sulfating higher $C_8$–$C_{18}$ alkyl alcohols produced naturally from coconut oil or those prepared synthetically from petroleum sources. Specific examples of alkyl sulfates useful in the present invention include sodium dodecyl sulfate, potassium dodecyl sulfate, ammonium dodecyl sulfate, monoethanolammonium dodecyl sulfate, diethanolammonium dodecyl sulfate, triethanolammonium dodecyl sulfate, sodium tetradecyl sulfate, potassium tetradecyl sulfate, ammonium tetradecyl sulfate, monoethanolammonium tetradecyl sulfate, triethanolammonium tetradecyl sulfate, sodium hexadecyl sulfate, ammonium hexadecyl sulfate, sodium coconut sulfate, sodium $C_{12}$–$C_{15}$ alkyl sulfate and mixtures thereof. Alkyl sulfates are sold commercially under several trade names which includes Carsonol ALS and Carsonol DLS, Carsonol SLS and Carsonol sold by Lonza Inc.; Duponol QC, Duponol D Paste, Duponol EP, Duponol G, Duponol LB Paste and Duponol WA Paste sold by Witco Corporation; Rhodapon CAV, Rhodapon L22, Rhodapon LSB, Rhodapon LT-6 and Rhodapon TDS sold by Rhone-Poulenc; Standpol A and Standpol DEA sold by Henkel Corpoporation; Sulfochem Sulfochem ALS, Sulfochem DLS, Sulfochem TLS and Sulfochem SLS sold by Chemron.

Another preferred class of anionic surfactant found to be most useful in the present invention are the sodium, potassium and ammonium salts of alkyl ether sulfates which are obtained by sulfating the higher $C_8$–$C_{18}$ alcohol ethoxylates. Such alcohols are reacted with about 1 to about 25 moles of alkylene oxide followed by sulfation and neutralization with base. Most highly preferred alkyl ether sulfates useful in the present invention include those comprising a mixture of individual compounds having an average chain length of about 10 to about 18 carbon atoms and an average degree of alkoxylation of about 1 to about 4 moles of ethylene oxide. Such a mixture can comprise from about 0% to about 50% by weight $C_{10}$–$C_{11}$ alkyl ether sulfate, from about 20% to about 100% by weight $C_{12}$ alkyl ether sulfate, from about 0% to about 80% by weight $C_{13}$–$C_{14}$–$C_{15}$–$C_{16}$ alkyl ether sulfates and from about 0% to about 30% by weight $C_{17}$–$C_{18}$ alkyl ether sulfates; and from about 5% to about 90% by weight of compounds having a degree of alkoxylation of 0; from about 7% to about 95% by weight of compounds having a degree of alkoxylation of 1 to 4; and from about 0% to about 35% by weight of compounds having a degree of alkoxylation greater than 5. Specific examples of alkyl ether sulfates useful in the present invention include sodium laureth-1 sulfate, sodium laureth-2 sulfate, sodium laureth-3 sulfate, potassium laureth-1 sulfate, potassium laureth-2 sulfate, potassium laureth-3 sulfate, ammonium laureth-1 sulfate, ammonium laureth-2 sulfate, ammonium laureth-3 sulfate, monoethanolammonium laureth-1 sulfate, monoethanolammonium laureth-2 sulfate, monoethanolammonium laureth-3 sulfate, diethanolammonium laureth-1 sulfate, diethanolammonium laureth-2 sulfate, diethanolammonium laureth-3 sulfate, triethanolammonium laureth-1 sulfate, triethanolammonium laureth-2 sulfate, triethanolammonium laureth-3 sulfate, sodium myreth-1 sulfate, sodium myreth-2 sulfate, sodium myreth-3 sulfate, ammonium myreth-1 sulfate, ammonium myreth-2 sulfate, ammonium myreth-3 sulfate, sodium $C_{10}$–$C_{16}$ alkyl (1) ether surfate, sodium $C_{10}$–$C_{16}$ alkyl (2) ether sulfate, sodium $C_{10}$–$C_{16}$ alkyl (3) ether sulfate and mixtures thereof. Alkyl ether sulfates are sold commercially under several trade names which includes Carson SLES-2 and Carson SES-A sold by Lonza Inc.; Duponol FAS sold by Witco Corporation; Norfox SLES-03 and Norfox SLES-60 sold by Norma, Fox & Co.; Standpol EA-1, Standpol EA-2, Standpol EA-3, Standpol EA-40, Standpol ES-1, Standpol ES-2, Standpol ES-3, Standpol ES-40, Standpol ES-50, Standpol ES-250 and Standpol 350 sold by Henkel Corporation; Sulfochem EA-1, Sulfochem EA-2, Sulfochem EA-3, Sulfochem EA-60, Sulfochem EA-70, Sulfochem ES-1, Sulfochem ES-2, Sulfochem ES-3, Sulfochem ES-60, Sulfochem ES-70 and Sulfochem K sold by Chemron.

Nonionic Surfactants

Suitable commercial nonionic surfactants are broadly exemplified as the polyoxyalkylene oxide condensation products of hydrophobic alkyl, alkene, or alkyl aromatic functional groups having a free reactive hydrogen available for condensation with hydrophilic alkylene oxide, such as ethylene oxide, propylene oxide, butylene oxide, polyethylene oxide or polyethylene glycol to form nonionic surfactants. Examples of such hydrophobic functional groups include hydroxy, carboxy, mercapto, amino or amido groups.

The overall reaction may be expressed as:

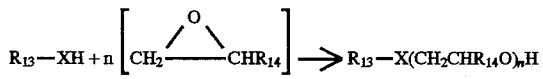

wherein $R_{13}$ is a hydrophobic alkene or alkane group having about 8 to about 18 carbon atoms: $R_{14}$ is hydrogen or an alkyl group with about 1 to about 2 carbon atoms; n is from about 1 to about 100; X is selected from the group consisting of O, $C_6H_4O$, $C_6H_3R_{13}O$, COO, S, NH, $NR_{15}$, CONH, $CONR_{15}$, $CONR_{15}(CH_2)_a(NR_{15})_2$ and $CONR_{15}(CH_2)_bNR_{15}(CH_2)_cN(R_{15})_2$; where $R_{15}$ is selected from the group consisting of H, $(CH_2CH_2O)_d$, $(CH_2CHCH_3O)_e$ and mixtures thereof; a+b+c is from about 1 to about 10; and d+e is from about 1 to about 100.

Examples of useful hydrophobes of commercial nonionic surfactants include higher $C_8$–$C_{18}$ alkyl fatty alcohols, middle $C_8$–$C_{14}$ alkyl phenols, higher $C_8$–$C_{18}$ alkyl fatty acids, higher $C_8$–$C_{18}$ alkyl mercaptans, higher $C_8$–$C_{18}$ alkyl fatty amines, higher $C_8$–$C_{18}$ alkyl amides and higher $C_8$–$C_{18}$ alkyl fatty alkanolamides. The polyoxyalkylene oxide condensate products of such materials may comprise from about 1 to about 100 moles of alkylene oxide, preferably from about 2 to about 60 moles of alkylene oxide, even more preferably from about 3 to about 25 moles alkylene oxide.

Description of Nonionic Surfactants

The polyoxyalkylene esters of alkyl fatty acids, the polyoxyalkylene alkyl mercaptans, the polyoxyalkylene alkyl fatty amides and the polyoxyalkylene alkyl fatty alkanolamides having an average alkyl chain length of about 8 to about 18 carbon atoms and from about 3 to about 25 moles of ethylene oxide represent a suitable class of nonionic surfactant useful in the present invention. Specific examples of such surfactants useful in the present invention include polyoxyethylene (8) lauryl mercaptan, polyoxyethylene (6) lauryl ester, polyoxyethylene (8) lauryl ester, polyoxyethylene (8) myristyl ester, polyoxyethylene (10) myristyl ester, polyoxyethylene (14) myristyl ester, polyoxyethylene (15) coconut ester, polyoxyethylene (7) laurylamide, polyoxyethylene (10) laurylamide, polyoxyethylene (20) laurylamide, polyoxyethylene (16) myristylamide, polyoxyethylene (12) cocoaide, polyoxyethylene (20) cocotriethanolamide and mixtures thereof.

Another suitable class of nonionic surfactant useful in the present invention are the polyoxyalkylene oxide block copolymers such as those obtained by the condensation of hydrophilic ethylene oxide with hydrophobic polyoxypropylene glycol. The hydrophobic portion of these compounds preferably has a molecular weight of about 1500 to about 1800 and exhibits water insolubility. The addition of polyoxyethylene units to this hydrophobic portion tends to increase the water solubility of the molecule as a whole and the liquid character of the product. Preferred surfactancy is retained up to the point where the polyoxyethylene content is from about 10% to about 50% by weight of the total condensation product. This corresponds to condensation of about 4 moles to about 40 moles ethylene oxide. Specific examples of commercially available polyoxyalkylene oxide block copolymers useful in the present invention include Pluronic L61, Pluronic L62, Pluronic L62D, Pluronic L62LF, Pluronic L63, Pluronic L64, Pluronic P65, and Pluronic F68 sold by BASF wherein the prefixes L, P and F before the numbers represent liquid, paste or flake form respectively. (Pluronic L62D is a low foaming version of Pluronic L62 and Pluronic L62LF is a mixture of 10% Pluronic L61 and 90% Pluronic L62).

Another suitable class of nonionic surfactant useful in the present invention are the polyoxyalkylene oxide block copolymers such as those obtained by the condensation of hydrophilic ethylene oxide with hydrophobic polyoxypropylene ethylenediamine or polyoxypropylene triethylenetetramine The hydrophobic portion of these compounds preferably has a molecular weight of about 2500 to about 4500 and exhibits water insolubility. The addition of polyoxyethylene units to this hydrophobic portion tends to increase the water solubility of the molecule as a whole and the liquid character of the product. Preferred surfactancy is retained up to the point where the polyoxyethylene content is from about 20% to about 90% by weight of the total condensation product. Specific examples of commercially available polyoxyethylene-polyoxypropylene ethylenediamines useful in the present invention includes Tetronic 702, Tetronic 704 and Tetronic 804 sold by BASF having the formula:

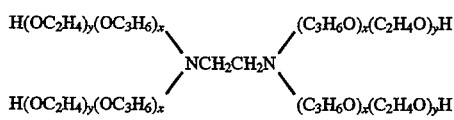

wherein x is from about 43 to about 78 of a polyoxypropylene group, which corresponds to an average molecular weight of about 2500 to about 4500; and y is from about 14 to about 920 of a polyoxyethylene group, which corresponds to an average molecular weight of about 625 to about 40,500 or about 20% to about 90% by weight of the total product.

Still another suitable class of nonionic surfactant useful in the present invention are the alkylmonoglycosides and alkylpolyglycosides as those disclosed in U.S. Pat. No. 4,565, 647 having the formula $R_{16}O(C_nH_{2n}O)_x(glycosyl)_y$ wherein $R_{16}$ is selected from the group consisting of alkyl, alkene, alkylphenyl, hydroxyalkyl, hydroxyalkylphenyl and mixtures thereof containing from about 8 to about 18 carbon atoms; preferably containing from about 10 to about 16 carbon atoms: n is 2 or 3, preferably n is 2; x is from about 0 to about 15, preferably x is 0; and y is from about 1 to about 8, preferably y is from about 1.1 to about 5, most preferably y is from about 1.2 to about 2.5. The glycosyl group may be derived from glucose, galactose, lactose, maltose, sucrose, starch, cellulose, fructose and mixtures thereof; preferably, however, the glycosyl is derived from high dextrose corn syrup, glucose or starch. Alkylpolyglycosides are prepared by the reaction of $C_8$–$C_{18}$ alkyl alcohols or $C_8$–$C_{18}$ alkylpolyoxyalkylene alcohols with glucose or a source of glucose at the anomeric position (carbon 1 hydroxyl group position) to form a glycoside. Additional glycosyl units can then be attached to the 2, 3, 4, and/or 6 hydroxyl group position of the newly formed glycoside to produce an alkylpolyglycoside. Optionally and less desirably the alkylpolyglycoside may be alkoxylated with alkylene oxide to form a polyoxyalkylene alkylpolyglycoside with about 8 to about 18 carbon atoms and about 1 to about 100 moles of ethylene oxide, preferably from about 2 to about 7 moles of ethylene oxide. Specific examples of alkylmonoglycosides useful in the present invention include dodecyl glucoside, tetradecyl glucoside and coconut glucoside. Specific examples of alkylpolyglycosides useful in the present invention include dodecyl polyglucoside with a degree of polymerization of 1.2, dodecyl polyglucoside with a degree of polymerization of 1.3, dodecyl polyglucoside with a degree of polymerization of 1.5, tetradecyl polyglucoside with a degree of polymerization of 1.2, tetradecyl polyglucoside with a degree of polymerization of 1.4, tetradecyl polyglucoside with a degree of polymerization of 1.6, $C_{10}$–$C_{16}$ alkyl polyglucoside with a degree of polymerization of 1.2, $C_{10}$–$C_{16}$ alkyl polyglucoside with a degree of polymerization of 1.4, coconut polyglucoside with a degree of polymerization of 1.2, coconut polyglucoside with a degree of polymerization of 1.3, coconut polyglucoside with a degree of polymerization of 1.5, coconut polyglucoside with a degree of polymerization of 2.1 and mixtures thereof.

Still another suitable class of nonionic surfactant useful in the present invention are the alkene oxide condensation products of polyhydroxyalkyl esters having about 8 to about 18 carbon atoms and about 1 to about 100 moles of ethylene oxide, preferably from about 3 to about 45 moles of ethylene oxide. Examples of polyhydroxyalkyl esters include those having about 2 to about 7 hydroxyl groups per alkyl chain such as ethylene glycol esters, propylene glycol esters, glycerol esters, polyglycerol esters, erythritol esters, xylitol esters, pentaerythritol esters, sorbitol/sorbitan esters, mannitol/mannitan esters, alkyl glucoside esters, glucose esters and sucrose esters. Preferred polyhydroxypolyoxyalkylene alkyl esters useful in the present invention include the polyoxyalkylene sorbitan, and mannitan esters having about 8 to about 18 carbon atoms and about 3 to about 45 moles of ethylene oxide. Specific examples of polyoxyalkylene sorbitan and mannitan esters include the Tweens, such as polyoxyethylene (10) sorbitan monolaurate, polyoxyethylene (20) sorbitan monolaurate, polyoxyethylene (44) sorbitan monolaurate, polyoxyethylene (20) monopalmitate, polyoxyethylene (20) sorbitan monostearate, polyoxyethylene (10) sorbitan monococoate, polyoxyethylene (20) sorbitan monococoate, polyoxyethylene (30) mannitan dilaurate and mixtures thereof.

Still another suitable class of nonionic suffactant useful in the present invention are the amine oxides of the formula:

$$R_{17}(OR_{18})_x(R_{19})_2N \to O$$

wherein $R_{17}$ is alkyl, alkene, hydroxyaikyl, acylamidopropyl and alkylphenyl group or mixtures thereof, containing about 8 to about 18 carbon atoms, preferably from about 10 to about 16 carbon atoms; $R_{18}$ is an alkylene or hydroxyalkylene group containing from about 2 to about 3 carbon atoms, preferably 2 carbon atoms; x is from about 0 to about 3, preferably x is 0; and each $R_{19}$ is an alkyl or hydroxyalkyl group containing from about 1 to about 3 carbon atoms, preferably from about 1 to about 2 carbon atoms, or a polyoxyethylene group having about 1 to about 3 moles of ethylene oxide, preferably from about 1 mole of ethylene oxide. The $R_{19}$ group can also be attached to each other e.g., through an oxygen or nitrogen atom to form a ring structure. Specific examples of amine oxides useful in the present invention include dimethyloctylamine oxide, diethyldecylamine oxide, dimethyldodecylamine oxide, diethyldodecylamine oxide, dimethyltetradecylamine oxide, dimethyl Alfol 1214 amine oxide, methylethylhexadecylamine oxide, diethyloctadecylamine oxide, dimethylcocoamine oxide, dimethyl-2-hydroxydodecylamine oxide, bis(2-hydroxyethyl)dodecylamine oxide, bis(2-hydroxyethyl) cocoamine oxide, bis(2-hydroxyethyl)oleylamine oxide, bis (2-hydroxyethyl) $C_{12}$–$C_{15}$ alkoxypropylamine oxide, dimethyldodecyloxyethylamine oxide, dodecylamidopropyldimethylamine oxide, tetradecylamidopropyldimethylaine oxide, cocoamidopropyldimethylamine oxide and mixtures thereof. Preferred amine oxide are the $C_{10}$–$C_{18}$ alkyldimethylamine oxides and the $C_{10}$–$C_{18}$ acylamidoalkyldimethylamine oxides.

Still another suitable class of nonionic surfactant useful in the present invention are the polyhydroxy fatty acid amides of the formula:

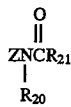

wherein $R_{20}$ is H, a $C_1$–$C_4$ alkyl, 2-hydroxyethyl, 2-hydroxypropyl group or mixtures thereof, preferably $R_{20}$ is methyl; and $R_{21}$ is a straight or branched chain $C_5$–$C_{31}$ alkyl, alkenyl, alkylphenyl, hydroxyalkyl, hydroxyalkylphenyl group, preferably a straight chain $C_9$–$C_{17}$ alkyl or alkene group; and Z is a polyhydroxy group containing at least 2 hydroxyl groups or an alkoxylated derivative thereof (preferably an ethoxylated or propoxylated derivative). Z may be derived from a reducing sugar in a reductive amination reaction and is preferably a glycityl. Examples of suitable reducing sugars include glucose, fructose, sucrose, maltose, lactose, galactose, mannose, xylose, starch and cellulose. As for commercial raw materials, high dextrose corn syrup, high fructose corn syrup and high maltose corn syrup can be utilized and may be preferred in some cases over the individual sugar components. Z may be selected from the group consisting of $HOCH_2(CHOH)_nCH_2$—or $HOCH_2(CHOH)CHOR_{22}(CHOH)_2CH_2$—where n is an integer from about 2 to about 6, inclusive, and $R_{22}$ is H or a cyclic or aliphatic monosaccharide. Most preferred are glycityls wherein n is 4, particularly $HOCH_2(CHOH)_4CH_2$—. Examples of $R_{20}$ include N-methyl, N-ethyl, N-propyl, N-isopropyl, N-butyl, N-2-hydroxyethyl and N-2-hydroxypropyl. Examples of >$NCOR_{21}$ include lauramide, myristamide, palmitamide, stearamide, oleamide, cocoamide and tallowamide. Examples of Z include 1-deoxyglucityl, 2-deoxyfructityl, 1-deoxymaltityl, 1-deoxylactityl, 1-deoxygalactityl, 1-deoxymannityl and 1-deoxymaltotriotityl. Optionally the polyhydroxy fatty acid aide may be alkoxylated with alkylene oxide to form a polyoxyalkylene polyhydroxy fatty acid aide with about 8 to about 18 carbon atoms and about 1 to about 100 moles of ethylene oxide, preferably from about 2 to about 7 moles of ethylene oxide. Methods for making polyhydroxy fatty acid aides are known in the art. In general, they are prepared by the reaction of an alkyl amine with a reducing sugar followed by reductive amination to form the corresponding N-alkyl polyhydroxyamine, which is then reacted with a fatty aliphatic ester or triglyceride in a condensation/amidation step to form the final N-alkyl N-polyhydroxy fatty acid aide product. Processes for making polyhydroxy fatty acid aides are disclosed in for example, U.S. Pat. No. 1,985,424 to Piggott, U.S. Pat. No. 2,703,798 to Schwartz and U.S. Pat. No. 2,965,576 to Wilson all of which are incorporated herein by reference.

Yet another suitable class of nonionic surfactant useful in the present invention are the non-heteroatom containing alkyl aldonamides and aldobionamides having about 8 to about 18 carbon atoms. Alkyl aldonamides and aldobionamides are prepared by the reaction of an aldonic acid, aldobionic acid, aldonolactone or aldobionolactone with a non-heteroatom containing alkyl amine such as decylamine, dodecylamine, tetradecylamine, hexadecylamine, octadecylamine, oleylamine and cocoamine in an organic solvent. Specific examples of alkyl aldonamides and aldobionamides useful in the present invention include dodecyl gluconamide, tetradecyl gluconamide, coco gluconamide, coco glucoheptonamide, decyl lactobionamide, dodecyl lactobionamide, tetradecyl lactobionamide, hexadecyl lactobionamide, octadecyl lactobionamide, oleyl lactobionamide, coco lactobionamide, coco maltobionamide and mixtures thereof.

Yet another suitable class of nonionic surfactant useful in the present invention are the alkyl glycoside esters having the formula:

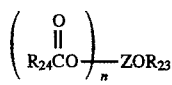

wherein $R_{23}$ is H, a $C_1$–$C_6$ alkyl, hydroxyethyl or hydroxypropyl group; preferably $R_{23}$ is methyl or ethyl; n is from about 1 to about 3; $R_{24}$ is a straight or branched chain alkyl, alkene, alkylphenyl, hydroxyalkyl, hydroxyalkylphenyl group having about 7 to about 17 carbon atoms and $ZOR_{23}$ is a polyhydroxy sugar group derived from the glycosidation of reducing sugars. Examples of suitable reducing sugars include glucose, fructose, sucrose, maltose, lactose, galactose, mannose, xylose, starch and cellulose. As for commercial raw materials, high dextrose corn syrup, high fructose corn syrup and high maltose corn syrup can be utilized and may be preferred in some cases over the individual sugar components. Examples of $ZOR_{23}$ include methyl glucoside, ethyl glucoside, hydroxyethyl glucoside, methyl galactoside, methyl fructoside, ethyl fructoside, methyl lactoside and ethyl sucroside. Alkyl glycoside esters are prepared by enzymatic esterification of $C_8$–$C_{18}$ fatty acids or by alkaline transesterification of $C_8$–$C_{18}$ fatty acid esters/triglycerides with alkyl glycosides such as methyl or ethyl glucoside at elevated temperature. The alkyl glycoside esters may also be ethoxylated or propoxylated with about 1 to about 150 moles of ethylene oxide, propylene oxide or mixtures thereof. Specific examples of alkyl glycoside esters useful in the present invention include methyl glucoside monococoate, ethyl glucoside monolaurate, ethyl glucoside monomyristrate, ethyl glucoside monococoate, ethyl glucose sesquicocoate, ethyl glucose dicocoate, methyl fructoside monococoate, methyl lactoside monococoate, methyl sucroside monococoate, sucrose cocoate, methyl gluceth-20 sesquistearate, PEG-120 methyl glucose dioleate, methyl gluceth-10, methyl gluceth-20 and mixtures thereof.

A preferred class of nonionic surfactant found to be useful in the present invention are the polyoxyalkylene alkyl alcohols having about 8 to about 18 carbon atoms in either branched or preferably straight chain configuration and about 1 to about 100 moles of ethylene oxide. Particularly preferred are the condensation products of alcohols having an alkyl group containing about 10 to about 16 carbon atoms with from about 3 to about 45 moles of ethylene oxide per mole of alcohol. Specific examples of commercially available nonionic surfactants of this type include Tergitol 15-S-9 (the condensation product of $C_{11}$–$C_{15}$ linear secondary alcohol with 9 moles of ethylene oxide and a narrow molecular weight distribution) and Tergitol 24-L-6NMW (the condensation product of $C_{12}$–$C_{14}$ primary alcohol with 6 moles of ethylene oxide) both sold by Union Carbide Corporation; Neodol 45-7 (the condensation product of $C_{14}$–$C_{15}$ linear alcohol with 7 moles of ethylene oxide), Neodol 45-9 (the condensation product of $C_{14}$–$C_{15}$ linear alcohol with 9 moles of ethylene oxide), Neodol 23-6.5 (the condensation product of $C_{12}$–C13 linear alcohol with 6.5 moles of ethylene oxide), Neodol 45-4 (the condensation product of $C_{14}$–$C_{15}$ linear alcohol with 4 moles of ethylene oxide), Neodol 25-7 (the condensation product of $C_{12}$–$C_{15}$ linear alcohol with 7 moles of ethylene oxide and Neodol 25-9 (the condensation product of $C_{12}$–$C_{15}$ linear alcohol with 9 moles of ethylene oxide) all sold by Shell Chemical Company. The CTFA adopted name for this class of nonionic surfactant is laureth-x (PEG-x lauryl ether), isolaureth-x (PEG-x isolauryl ether), myreth-x (PEG-x myristyl ether), ceteth-x (PEG-x cetyl ether), steareth-x (PEG-x stearyl ether), oleth-x (PEG-x oleyl ether), cetoleth-x (PEG-x cetyl/oleyl ether) and ceteareth-x (PEG-x cethyl/stearyl ether) wherein x is about 1 to about 60 and represents the degree of ethoxyltion. Preferred are laureth-4 through 25, myreth-4 through 10, ceteth-5 through 30 and stearth-3 through 40.

Another preferred class of nonionic surfactant found to be useful in the present invention are the polyoxyalkylene alkylphenols having about 8 to about 14 carbon atoms in either branched or preferably straight chain configuration and about 1 to about 100 moles of ethylene oxide, preferably from about 5 to about 23 moles of ethylene oxide. Specific examples of commercially available nonionic surfactants of this type include Igepal CO-610 (the condensation product of nonylphenol with about 7 to about 8.5 moles of ethylene oxide), Igepal CO-630 (the condensation product of nonylphenol with 9 moles of ethylene oxide), Igepal RC-620 (the condensation product of dodecylphenol with about 10 moles of ethylene oxide, Igepal RC-630 (the condensation product of dodecylphenol with about 12 moles of ethylene oxide), Igepal DM-710 (the condensation product of dinonylphenol with about 15 moles of ethylene oxide) all sold by GAF Corporation and Triton X-114 (the condensation product of octylphenol with about 7 to about 8 moles of ethylene oxide), Triton X-100 (the condensation product of octylphenol with about 9 to about 10 moles of ethylene oxide) and Triton X-102 (the condensation product of octylphenol with about 12 to about 13 moles of ethylene oxide) all sold by Rohm & Haas Company. The CTFA adopted name for this class of nonionic surfactant is octoxynol, nonoxynol and dodoxynol. Preferred are octoxynol-5 through 20, nonoxynol-5 through 23 and dodoxynol-5 through 12.

Amphoteric Surfactants

There are two classes of amphoteric surfactant; those that are pH sensitive (amphoteric) and those that are pH insensitive (zwitterionic).

Suitable amphoteric surfactants are exemplified as those which can be broadly classified as derivatives of aliphatic secondary and tertiary amines which contain a quaternary ammonium or non-quaternary ammonium group and one long chained alkyl or alkene group having about 8 to about 18 carbon atoms and at least water solubilizing radical selected from the group consisting of sulfates, sulfonates, carboxylates, phosphates or phosphonates.

Examples of such amphoteric surfactants include the N-alkyl β-amino propionates, such as sodium(dodecyl β-amino)propionate (sodium lauraminopropionate), diethanolamine lauraminopropionate and sodium cocoaminopropionate; the N-alkyl β-imino dipropionates, such as disodium(dodecyl β-imino)dipropionate (sodium lauriminodipropionate) and cocoiminodipropionate; the alkyl taurinates, such as monoethanolammonium coconut taurinate as taught in U.S. Pat. No. 2,658,072 which is incorporated herein by reference and the derivatives derived from 2-alkyl-2-imidazoline, such as those sold under the trade name Miranol as taught in U.S. Pat. Nos. 2,528,378, 2,773,068, 2,781,354 and 2,781,357 all of which are incorporated herein by reference. The amphoteric imidazoline derived surfactants are a preferred class of amphoteric surfactant and are prepared by condensing aminoethylethanolamine, diethylenetriamine or ethylenediamine with a fatty acid having about 8 to about 18 carbon atoms to form a five-membered imidazoline ring which may be ionized by an anionizable alkylating agent such as sodium chloroacetate, methyl or ethyl acrylate, acrylic acid, 2-hydroxy-1,3-propane sultone, 3-chloro-2-hydroxypropane sulfonic acid and 1,3-propane suitone on or near the cyclic portion or cationic portion of the molecule. Alkylations may be done with or without solvent or in aqueous solution. In aqueous solution, the imidazoline ring may be hydrolytically opened to form a mixture of imidazoline and linear amide. Specific examples of amphoteric imidazoline-derived surfactants useful in the present invention include lauroamphocarboxypropionate, lauroamphopropionate, lauroamphoglycinate, lauroamphocarboxyglycinate, lauroamphopropylsulfonate, lauroamphocarboxypropionic acid, myristoamphocarboxypropionate, myristoamphopropionate, myristoamphoglycinate, myristoamphocarboxyglycinate, myristoamphopropylsulfonate, myristoamphocarboxypropionic acid, cocoamphocarboxypropionate, cocoamphopropionate, cocoamphoglycinate, cocoamphocarboxyglycinate, cocoamphopropylsulfonate, cocoamphocarboxypropionic acid and mixtures thereof. The CTFA adopted name for this class of amphoteric surfactant is amphoteric-1 through 20. Preferred are amphoteric-1, amphoteric-2, amphoteric-6, amphoteric-10, amphoteric-12, amphoteric-17, amphoteric-18, amphoteric-19 and amphoteric-20.

Zwitterionic Surfactants

Suitable zwitterionic surfactants are exemplified as those which can be broadly described as derivatives of aliphatic quaternary ammonium, sulfonium and phosphonium compounds with one long chain group having about 8 to about 18 carbon atoms and at least one water solubilizing radical selected from the group consisting of sulfate, sulfonate, carboxylate, phosphate or phosphonate. A general formula for these compounds is:

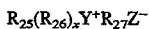

$$R_{25}(R_{26})_xY^+R_{27}Z^-$$

wherein $R_{25}$ contains an alkyl, alkene or hydroxyalkyl group with about 8 to about 18 carbon atoms, from about 0 to about 10 moles of ethylene oxide and from about 0 to about 2 glyceryl units; Y is a nitrogen, sulfur or phosphorous atom; $R_{26}$ is an alkyl or hydroxyalkyl group with about 1 to about 3 carbon atoms; x is 1 when Y is a sulfur atom and 2 when Y is a nitrogen or phosphorous atom; $R_{27}$ is an alkyl or hydroxyalkyl group with about 1 to about 5 carbon atoms and Z is radical selected from the group consisting of sulfate, sulfonate, carboxylate, phosphate or phosphonate. Examples of such zwitterionic surfactants include the sulfatobetaines, such as 3-(dodecyldimethylammonio)-1-propane sulfate and 2-(cocodimethylammonio)-1-ethane sulfate; the sulfobetaines, such as 3-(dodecyldimethylammonio)-2-hydroxy-1-propane sulfonate, 3-(tetradecyldimethylammonio)-1-propane sulfonate, 3-($C_{12}$-$C_{14}$ alkylamidopropyldimethylammonio)-2-hydroxy-1-propane sulfonate, 3-(cocodimethylammonio)-1-propane sulfonate; the carboxybetaine such as (dodecyldimethylammonio)acetate (lauryl betaine), (tetradecyldimethylammonio)acetate (myristyl betaine), (cocodimethylammonio)acetate (coconut betaine), (oleyldimethylammonio)acetate (oleyl betaine), (dodecyloxymethyldimethylammonio)acetate, (tetradecyloxyhydroxylpropyldimethylammonio)acetate, [cocodi(polyethoxyethanol)ammonio]acetate, (dodecyldimethylammonio)propionate, (dodecylamidopropyldimethylammonio)acetate, (cocoamidopropyldimethylammonio)acetate (also known as cocoamidopropyl betaine); the sulfoniobetaines such as (dodecyldimethylsulfonio)acetate and 3-(cocodimethylsulfonio)-1-propane sulfonate and the phosphoniobetaines such as 4-(trimethylphosphonio)-1-hexadecane sulfonate 3-(dodecyldimethylphosphonio)-1-propanesulfonate, 2-dodecyldimethylphosphonio)-1-ethane sulfite and mixtures thereof.

Means for preparing many of the surfactant compounds of this class are described in U.S. Pat. Nos. 2,129,264, 2,697,656, 2,774,786, 2,813,898, 2,828,332, 3,265,719, 3,529,521 and German Pat. No. 1,018,421, all of which are incorporated herein by reference.

Of all the above described types of zwitterionic surfactants, preferred compounds include the sulfobetaines such as 3-(cocodimethylammonio)-1-propanesulfonate, 3-(cocodimethylammonio)-2-hydroxy-1-propanesulfonate and the carboxybetaines such as (cocodimethylammonio)

acetate, (dodecylamidopropylammonio)acetate and (cocoamidopropylammonio)acetate (cocoamidopropyl betaine).

Cationic Surfactants

Cationic surfactants have been taught in the art as conditioning agents for the hair. Suitable cationic surfactants are broadly exemplified as those of the general formula:

$$[R_{28}R_{29}N^+R_{30}R_{31}]_A{}^-$$

wherein $R_{28}$ contains an alkyl, alkene or alkylphenyl group with about 10 to about 24 carbon atoms; $R_{29}$, $R_{30}$ and $R_{31}$ contains an alkyl, alkene or alkylphenyl group with about 10 to about 24 carbon atoms, or an alkyl or alkylhydroxy group with about 1 to about 5 carbon atoms; and A- can be any salt forming anion such as halide, hydroxide, sulfate, carbonate and phosphate.

Examples of such cationic surfactants include myristyltrimethyl ammonium chloride, cetyltrimethylammonium chloride, stearyltrimethylammonium chloride, oleyltrimethylammonium chloride, tallowtrimethylammonium chloride, dimyristyldimethylammonium chloride, dicetyldimethylammonium chloride, distearyldimethylammonium chloride, distearyldiethylammonium bromide, dioleyldimethylammonium chloride, ditallowdimethylammonium chloride, stearyldimethylbenzyl ammonium chloride (stearalkonium chloride), PPG-9 diethylmonium chloride, PPG-25 diethylmonium chloride, PPG-40 diethylmonium chloride, trimyristylmethyl ammonium chloride, tricetylmethylammonium chloride, tristearylmethylammonium chloride, bishydroxyethyl dihydroxypropyl steramonium chloride, gaur hydroxypropyltrimonium chloride, benzyl trimethylammonium hydrolyzed animal protein or mixtures thereof. The CTFA adopted name for this class of cationic surfactant is quaternium. Preferred cationic surfactants are quaternium-1 through 84, most preferably quaternium-6, quaternium-16, quaternium-19, quaternium-20, quaternium-22, quaternium-23, quaternium-26, quaternium-32, quaternium-33, quaternium-41, quaternium-60 and quaternium-70. The polymeric cationic surfactants such as polyquaternium-1 through 39 are useful as well, preferably polyquaternium-7, polyquaternium-8, polyquaternium-10, and polyquaternium-11.

Many additional non-soap surfactants are described in McCutcheon's Detergents and Emulsifiers (Vol. 1) and McCutcheon's Functional Materials (Vol. 2), 1992 Annual, published by MC Publishing Co. as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference.

The above mentioned cosurfactants (anionic, nonionic, amphoteric, zwitterionic, cationic surfactant and mixtures thereof) are used in combination with the heteroatom containing alkyl aldonamides in hair care compositions of the present invention. The anionic surfactants, particularly the alkyl sulfates and the alkyl ether sulfates, the nonionic surfactants, particularly the alkyl polyoxyalkylene sorbitan esters and the alkyl polyglycosides, and the amphoteric surfactants particularly, the alkyl carboxybetaines are preferred for use herein.

Typical levels of cosurfactant are from about 0% to about 45%, preferably from about 0.1% to about 40%, even more preferably from about 0.2% to about 35% by weight of the composition.

Hair Conditioning Agents

Various materials have been taught in the art for use as agents that condition the hair. In general, such conditioning agents are designed to enhance fullness, body, manageability, softness, luster and overall attractive appearance and handling properties of the hair. Examples of such conditioning agents include, lanolin and its derivatives, long chain esters such as isopropyl myristate, butyl palmitate, stearyl stearate, carylic/capric triglycerides, polyols such as glycerol (glycerin), propylene glycol and the like, oils, amine oxides, fatty alcohols, carbohydrates, fatty acids, alkyl pyrrolidones, polyvinylpyrrolidone (PVP), sodium PCA, vitamins, amino acids, silicones and certain cationic surfactants. It is to be understood that any such conditioning agent can be employed herein, depending on the formulations desires, however, the silicones and cationics are particularly preferred.

Suitable non-volatile silicone fluids are exemplified as polyalkylsiloxane, polyarylsiloxane, polyalkylarylsiloxane and polyethersiloxane copolymers which are present at about 0% to about 10%, preferably from about 0% to about 8%, even more preferably from about 0% to about 6% by weight of the composition. Mixtures of these fluids may also be used and are preferred in certain executions. The silicone fluid should be insoluble in the shampoo matrix and present as a dispersion.

Examples of non-volatile polyalkylsiloxane fluids useful in the present invention include, for example, the polydimethylsiloxanes having viscosities from about 5 to about 600,000 centistokes at 25° C., preferably from about 350 to about 100,000 centistokes at 25° C.

Examples of non-volatile polyalkylarylsiloxane fluids useful in the present invention include, for example, the polymethylphenylsiloxanes having viscosities from about 15 to about 30,000 centistokes at 25° C.

Examples of non-volatile polyethersiloxane copolymer fluids useful in the present invention include, for example, the polyethylene oxide modified dimethylpolysiloxanes (dimethicone copolyol), polypropylene oxide modified dimethylpolysiloxanes and polyethylene oxide/polypropylene oxide modified dimethylpolysiloxanes and mixtures thereof.

Other silicone materials useful in the present compositions are the silicone gums as described in U.S. Pat. No. 4,152,416 and in Chemistry and Technology of Silicones published by Academic Press (1968) both of which are incorporated herein by reference. Silicone gums are generally high molecular weight polydiorganosiloxanes having a mean molecular weight from about 200,000 to about 1,000,000. Specific examples of silicone gums include polydimethylsiloxane, (polydimethylsiloxane) (methylvinylsiloxane) copolymer, poly (dimethylsiloxanediphenyl)(methylvinylsiloxane) copolymer and mixtures thereof. References that describe suitable silicone fluids include U.S. Pat. Nos. 2,826,551, 3,964,500, 4,364,837, British Pat. No. 849,433 and Silicon Compounds distributed by Petrarch Systems, Inc. all of which are incorporated herein by reference.

The silicone fluids are present from about 0% to about 10%, preferably from about 0% to about 8%, even more preferably from about 0% to about by weight of the composition.

Auxiliary Thickening Agents

Various materials have been taught in the art as auxiliary thickening agents that are useful in combination with heteroatom containing alkyl aldonamide compounds of the present invention for enhancing viscosity and rendering the composition more acceptable.

Examples of common thickening agents include fumed silica, bentonite (hydrated aluminum silicone dioxide), PEG 55 propylene glycol oleate, PEG 6000 distearate, cellulose gum, hydroxypropyl cellulose, hydroxyethyl cellulose, hydroxypropyl methyl cellulose, sodium carboxymethyl cellulose, carrageenan, veegum (magnesium aluminum silicate), xanthan gum, gaur hydroxypropyltrimonium chloride, gaur gum, pectin, amine oxides, glucose glutmate, stearamidopropyldimethylamine lactate and the alkanolamides.

Examples of another type of thickening agent (gelling agent/viscosity control agent) found to be useful in the present invention include the poly(oxyethylene)-poly (oxypropylene) block copolymers such as poloxamer 101 through 941 sold by BASF, ICI Americas and Hodag. Of this class of thickening agent, poloxamer 101, poloxamer 182, poloxamer 238, poloxamer 934 and poloxamer 941 and mixtures thereof are preferred and poloxamer 188, poloxamer 237, poloxamer 338, poloxamer 407 and mixtures thereof are highly preferred. The poly(oxyethylene)-poly (oxypropylene) block polymers are of the formula:

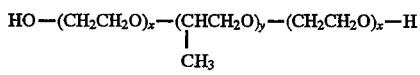

wherein:

X=75 and Y=30 for poloxamer 188
X=62 and Y=39 for poloxamer 237
X=128 and Y=54 for poloxamer 338
X=98 and Y=67 for poloxamer 407

These products are complex mixtures of copolymer produced in a wide range of molecular weights (1,100–14,000) with varying degrees of ethylene oxide and propylene oxide. The block polymers are prepared by polymerizing propylene oxide in a controlled fashion to give a desired weight followed by ethoxylation with ethylene oxide. The ethoxylated portions of the block polymer can provide from about 10% to about 80% by weight of the final product.

Preferred thickeners are the alkanolamides which are prepared by the reaction of a $C_8$–$C_{18}$ alkyl fatty acid, $C_8$–$C_{18}$ alkyl fatty acid ester or $C_8$–$C_{18}$ alkyl fatty acid halide with a hydroxyl alkylamine such as monoethanolamine or diethanolamine. Suitable examples of alkanolamides useful as auxiliary thickening agents include lauric monoethanolamide, lauric diethanolamide, myristic monoethanolamide, myristic diethanolamide, coco monoethanolamide, coco diethanolamide, palmitic monoethanolamide, linoleic monoethanolamide, linoleic diethanolamide, hydroxystearyl monoethanolamide, almond diethanolamide, palm kernel diethanolamide, oleic monoethanolamide and mixtures thereof. Most highly preferred auxiliary thickening agent useful in the present invention include are lauric monoethanolamide (lauramide MEA), lauric diethanolamide (lauramide DEA), coco monoethanolamide (cocoamide MEA) and coco diethanolamide (cocoamide DEA) which may be present from about 0% to about 10%, preferably at about 0% to about 8%, even more preferably from about 0% to about 6% by weight of the composition.

Antidandruff Agents

Various materials have been taught in the art as agents that are useful in removing or preventing the formation of a flaky, itchy condition generally known as dandruff.

Examples of traditional antidandruff agents include menthol, sulfur, salicylic acid, piroctone olamine (octopirox), hexachlorophene, resorcinol, coal tar coal, tar extract, coal tar solution and certain cationics such as cetyldimethylbenzylammonium bromide. Currently however, most authorities in this area recognize that antidandruff agents based on pyridinethione salts, piroctone olamine or selenium sulfide are most effective against dandruff, and such materials are preferred. It should be understood that any such antidandruff agent can be employed herein, depending on the formulators desires, however, the pyridinethione salts are most especially preferred. The pyridinethione salts are based on suitable heavy metals such as in zinc, cadmium, magnesium, tin, aluminum and zirconium, however, zinc as in zinc pyridinethione (zinc pyrithione) is highly preferred. The use of pyridinethione salts as antidandruff agents in shampoos and hair rinses are disclosed in the U.S. Pat. Nos. 2,809,971, 3,236,733, 3,723, 325, 3, 753,916, 3,761,417 and 3,761,418 all of which are incorporated herein by reference.

Typical levels of antidandruff agent are from about 0% to about 8%, preferably from about 0% to about 6%, even more preferably from about 0% to about 4% by weight of the composition. Mixtures of antidandruff agents can also be used.

Suspending Agents

Various materials have been taught in the art as agents that are useful in suspending certain performance ingredients such as zinc pyridinethione platelets, silicone fluids, and the like, uniformly, thereby assisting in the delivery of the desirable performance attributes associated with these ingredients. The suspending agent useful in the present invention can be any of several long chain acyl derivatives or mixtures thereof. Included are the glycol mono-, di- and triesters having about 14 to about 22 carbon atoms. Preferred glycol esters include the ethylene glycol mono- and distearates, glyceryl stearates, palm off glyceride, tripalmitin, tristearin and mixtures thereof.

Another example of a suspending agent useful in the present invention include the alkanolamides having from about 14 to about 22 carbon atoms. Preferred alkanolamides are stearic monoethanolamide, steric diethanolamide, stearic monoisopropanolamide, stearic monoethanolamide stearate and mixtures thereof.

Still another example of a suspending agent useful in the present invention include the long chain fatty acid esters such as stearyl stearate, stearyl palmirate and palmityl palmirate.

Still another example of a suitable suspending agent useful in the present invention include the long chain amine oxides having from about 14 to about 22 carbon atoms. Preferred mine oxides are hexadecyldimethylamine oxide and octadecyldimethylamide oxide.

Yet another example of a suitable suspending agent (or thickening agent) useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, hydroxymethyl carboxypropyl cellulose, methyl cellulose, ethyl cellulose, guar gum, gum karaya, gum tragacanth, gum arabic, gum acacia, gum agar, xanthan gum and mixtures thereof. Preferred carbohydrate gums are the cellulose gums and xanthan gum.

Of all the above described types of suspending agents, preferred compounds include the long chain glycol esters and the carbohydrate gums.

The suspending agent or mixtures of agent may be present from about 0% to about 7%, preferably from about 0% to about 5%, even more preferably from about 0% to about 4% by weight of the composition.

Water

Water is the last essential component of the present invention and forms the remainder of the composition.

Water is generally present from about 1% to about 95%, preferably from about 45% to about 90%.

Optional Ingredients (Auxilary Agents)

The shampoos herein can contain a variety of less essential optional ingredients (auxilary agents) suitable for rendering such compositions more acceptable. Such ingredients are well known to those skilled in the art and include, but are not limited to, hair styling agents, viscosity control agents, emulsifiers/emollients, dispersants, conditioning emollient oils, conditioning extracts, humectants. solubilizing/clarifying agents, stabilizers, sun-screens/UV absorbers, opacifiers/pearlescent agents, vitamins amino acids, proteins, curl enhancing agents, hair coloring agents, chelating/sequestering agents, hydrotropes, anti-lice agents, hair straightening agents, preservatives/antimicrobial agents, bactericides/fungicides, antioxidants, brightening agents (bleaches), pH control agents, buffering agents, colorants and perfumes/fragrances. These ingredients, when used, are added at their usual levels, each generally up to about 10% by weight of the composition and usually totaling up to about 0.001% to about 35% by weight of the composition.

Examples of hair styling agents useful in the present invention include styling polymers such as vinyl pyrrolidone/vinyl acetate copolymers (30/70 by weight), vinyl acetate homopolymer, t-butyl acrylate homopolymer, t-butyl sterene/ethyl hexyl methacrylate copolymer (50/50 by weight), dimethyl acrylamide/t-butyl acrylate/ethylhexyl methacrylate copolymer (10/45/45 by weight), ethylene/vinyl acetate copolymer (12.5/87.5 by weight), allyl alcohol/styrene copolymer (19/81 by weight), vinyl chloride/vinyl acetate copolymer (83/17 by weight and lower), vinyl pyrrolidone/vinyl acetate/butyl acrylate copolymer (10/78/12 and 10/70/20 by weight), vinyl pyrrolidone/vinyl acetate/butyl acrylate/styrene sulfonate copolymer (10/70/15/5 by weight), vinyl pyrrolidone/vinyl propionate copolymer (5/95 by weight), vinyl caprolactam/vinyl acetate copolymer (5/95 by weight), ethyl acrylate/acrylic acid/t-butyl acrylamide copolymer, vinyl acetate/crotonic acid copolymer (90/10 by weight), vinyl acetate/vinyl propionate/crotonic acid (50/40/10 by weight) and vinyl acetate/vinyl neodecanoate/crotonic acid copolymer. Typical levels of hair styling agent which are designed to assist the user in having the shampooed hair retain a particular shape are from about 0% to about 10% by weight of the composition.

Examples of organic viscosity modifying agents useful in the present invention include $C_8$–$C_{18}$ alkyl fatty alcohols, $C_8$–$C_{18}$ alkyl fatty acids, $C_8$–$C_{18}$ alkyl fatty esters, ethanol, isopropanol and benzyl alcohol. Examples of inorganic viscosity modifying agents include ionizable salts such as sodium chloride, potassium chloride, calcium chloride, magnesium chloride, potassium bromide, ammonium chloride, sodium sulfate, potassium sulfate, magnesium sulfate and sodium thiosulfate. The ionizable salts are particularly useful for obtaining or modifying a desired viscosity. The amount of ionizable salt used depends on the amount of active ingredient present and can be adjusted according to the formulators desires. Typical levels of salt used to control composition viscosity are from about 0.1% to about 10% by weight of the composition.

Examples of emulsifiers/emollients (refattying agents) or dispersants useful in the present invention which condition the hair and scalp and assist in the ease of combing, detangling, body, shine, manageability, split-end mending and prevent static build-up include dimethicone, cyclomethicone, amodimethicone, lanolin oil, lanolin fatty acid, lanolin alcohol, acetylated lanolin alcohol, acetylated alkoxylated lanolin such as laneth-9 acetate and laneth-10 acetate, alkoxylated lanolin having about 30 to about 75 moles of ethylene oxide or propylene oxide such as PEG-16 lanolin, PEG-27 lanolin, PEG-40 lanolin, PEG-75 lanolin and PPG-12-PEG-50 lanolin, long chain esters such as cetyl acetate, stearyl acetate, oleyl acetate, lauryl lactate, myristyl lactate, cetyl lactate, stearyl lactate, decyl neopentanoate, decyl oleate, isopropyl myristate, lauryl myristate, myristyl myristate, myreth-3-myristate, palmityl myristate, stearyl myristate, isopropyl palmitate, octyl palmitate, 2-ethylhexyl palmitate, lauryl palmirate, myristyl palmitate, palmityl palmirate, stearyl palmitate, butyl stearate, myristyl stearate, palmityl stearate, isocetyl stearate, isostearyl isostearate, myristyl alcohol, cetyl alcohol, isocetyl alcohol, stearyl alcohol, oleyl alcohol, dioctyl succinate, didecyl succinate, caprylic/capric triglycerides, ethoxylated cholesterol, PEG-16 soya sterol, and mixtures thereof. Typical levels of emulsifier or emollient are from about 0% to about 10% by weight of the composition.

Examples of conditioning emollient oils useful in the present invention which condition the hair and scalp and assist in the ease of combing, detangling, body, shine, manageability, split-end mending and prevent static build-up include arnica blossom oil, apricot kernel oil, avocado oil, babassa oil, balm mint oil, basil oil, bergamot oil, bitter almond oil, bitter orange oil, castor oil, calendula oil, coconut oil, collagen/lanolin oil, cod liver oil, cucumber oil, corn oil, carrot oil, egg oil, eucalyptus oil, evening primrose oil, geranium oil, gardenia oil, grapefruit oil, grape seed oil, hybrid safflower oil, jasmine oil, jojoba oil, kiwi oil, light mineral oil, lemon oil, mandarin orange oil, orange flower oil, orange oil, mink oil, olive oil, palm oil, peach kernel oil, passionflower oil, rapeseed oil, sesame oil, soybean oil, safflower oil, sunflower oil, sweet almond oil, wheat germ oil and mixtures thereof. Typical levels of conditioning emollient oil are from about 0% to about 10% by weight of the composition.

Examples of conditioning extracts useful in the present invention which condition the hair and scalp and assist in the ease of combing, detangling, body, shine, manageability, split-end mending and prevent static build-up include aloe extract, aloe flower extract, aloe vera gel extract, apple extract, apple leaf extract, apple pectin extract, balsam canada extract, balsa oregon extract, balsam peru extract, balsam tolu extract, balm mint extract, black walnut extract, birch leaf extract, birch sap extract, calendula extract, chamomile extract, colocynth extract, comfrey extract, comfrey leaf extract, coltsfoot extract, clover blossom extract, custard apple extract, egg extract, fennel extract, gelatin extract, geranium extract, grapefruit extract, horsetail extract, henna extract, hazel extract, hops extract, honey extract, indian cress extract, kelp extract, lemon extract, lemon juice extract, lemon peel extract, lime extract, malt extract, mandarin orange extract, matricaria extract, mint extract, nettle extract, oakmoss extract, orange extract, orange peel extract, ponkan extract, papaya extract, pummelo extract, red raspberry extract, red raspberry leaf extract, rhubarb extract, rosemary extract, thyme extract, tamarind extract, tangerine extract, sage extract, strawberry extract, strawberry leaf extract, valerian extract, witch hazel extract, autolyzed yeast extract, yarrow extract and mixtures thereof. Preferred extracts are balsam canada, balsam oregon, balsam peru, balsam tolu and honey. Typical levels of conditioning extract are from about 0% to about 10% by weight of the composition.

Examples of humectants useful in the present invention which provide moisture to the hair and scalp include propylene glycol (PG), butylene glycol, hexylene glycol, PEG (polyethylene glycol), PEG-5M, PEG-6, PEG-9, PEG-10, PEG-14M, PPG-12-buteth-16, PPG-12-buteth-16, PPG-28-buteth-35, glycerol (glycerin), erythritol, xylitol, sorbitol, mannitol, lactitol, hydrogenated starch hydrolyzates, sodium pyrrolidone carboxylic acid (sodium PCA), ethoxylated/propoxylated methyl glucose, lactic acid, acetamide MEA, lactamide MEA, wheat germamidopropyldimethyl lactate, $C_{12}$–$C_{15}$ lactate, stearamidopropyldimethyl lactate and mixtures thereof. Preferred humectants are propylene glycol, glycerol, hydrogenated starch hydrolyzates acetamide MEA, lactamide MEA and sodium pyrrolidone carboxylic acid. Typical levels of humectant are from about 0% to about 10% by weight of the composition.

Examples of solubilizing or clarifying agents useful in the present invention which assist in maintaining hair care composition clarity by solubilizing poorly soluble ingredients include methanol, ethanol, propanol, isopropanol, butanol, ethoxydiglycol, phenyl ethanol, phenyl propanol, benzyl alcohol, ethyl buyrate, isopropyl butyrate, diethyl phthalate, phenylethyldimethyl carbinol, ethyl-6-acetoxyhexanoate, methyl(2-pentanyl-3-oxy) cyclopentylacetate, ethylene glycol, diethylene glycol, triethylene glycol, polyethylene glycol having a molecular weight of about 200 to about 1000, propylene glycol, glycerol, 3,6-dimethyl-4-octyne-3,6-diol, 2-methyl-2,4-pentanediol, 2-ethyl-1,3-hexanediol and nonionic surfactants particularly polyoxyethylene nonionic surfactants. Typical levels of solubilizing or clarifying agent are from about 0% to about 10% by weight of the composition.

Examples of sunscreens or UV absorbers useful in the present invention which protect the hair and certain sensitive ingredients from harmful sunlight include dipropyleneglycol salicylate, octyl salicylate, 2-ethylhexyl p-dimethylaminobenzoate (octyldimethyl-PABA), polyoxyethylene p-dimethylaminobenzoate (PEG-25 PABA), Tri-PABA-panthenol, dromtrizole, 2-ethylhexyl p-methoxycinnamate, DEA p-methoxycinnamate, butyl methoxybenzoylmethane, benzophenones 1 through 12 particularly, 2,4-dihydroxybenophenone (benzophenone 1), 2,2',4,4'-tetrahydroxybenzophenone (benzophenone 2), 2-hydroxy-4-methoxybenzophenone (benzophenone 3), 2-hydroxy-4-methoxybenzophenone-5-sulfonic acid (benzophenone 4), 2,2'-dihydroxy-4,4'-dimethoxybenzophen (benzophenone 6), 2,2'-dihydroxy-4-methoxybenzophenone (benzophenone 8), disodium-2,2'-dihydroxy-4,4'-dimethoxy-5,5'-disulfobenzophenone (benzophenone 9), 2-hydroxy-4-n-octoxybenzophenone, menthyl anthranilate, 2-(2-hydroxy-5'-methylphenyl)-benzotriazole, 2-phenylbenzimidazole-5-sulfonic acid and mixtures thereof. Preferred sunscreens are the benzophenones 1 through 6, 8, 9 and 11. Typical levels of sunscreen or UV absorber are from about 0% to about 8% by weight of the composition.

Examples of opacifiers and pearlescent agents useful in the present invention which provide a soft, silvery and pearly luster to hair care compositions include hexadecanol, octadecanol, tallow alcohol, oleyl alcohol, ethylene glycol monostearate, ethylene glycol distearate, diethylene glycol distearate, triethylene glycol distearate, glycerol mono/distearate, PEG 400 stearate, PEG 600 oleate, PEG-4 to PEG 150 laurate/dilaurate, PEG 4 to PEG 150 stearate/distearate, PEG-4 to PEG 150 oleate/dioleate, coco gluconamide, tallow gluconamide, dodecyl gluconamide hexadecyl gluconamide, octadecyl gluconamide, coco glucoheptonamide, tallow lactobionamide, octadecyl lactobionamide, tallow maltobionamide, bismuthoxychloride, spermaceti, magnesium silicate, calcium silicate, guanine, zinc oxide, titanium dioxide (anatose form or rutile form), titanium dioxide coated mica and coloured pigments coated mica and as well as the zinc, calcium and magnesium salts of fatty acids such as myristic acid, palmitic acid, stearic acid, behenic acid, coconut fatty acid. Preferred are the non-hetero-atom containing alkyl aldonamides/aldobionamides and the ethylene glycol esters such as ethylene glycol monostearate and distearate. Typical levels of opacifiers or pearlescent agent are from about 0% to about 7% by weight of the composition.

Examples of vitamins useful in the present invention which provide the hair with valuable nutrition include vitamin A (as retinyl acetate, propionate or palmitate) provitamin A (based on earrot extract, as β-carotene), vitamin $B_1$ (as thiamine mononitrate), vitamin $B_2$ (as riboflavin), vitamin $B_3$ (as niacinamide, vitamin $B_5$ (as pantothenic acid), provitamin $B_5$ (as panthenol), vitamin $B_6$ (as pyridoxine hydrochloride, dioctenoate, dilaurate, dipalmitate or tripalmitate), vitamin $B_{12}$ (as cyanocobalamin), vitamin $B_{15}$ (as pangamic acid), vitamin C (as aseorbie add), vitamin $D_2$ (as ergocalciferol), vitamin $D_3$ (as cholecalciferol), vitamin E (as dl-α-tocopherol acetate, linoleate or nicotinate,), vitamin F (as glyceryl linoleate and glyceryl linolenate), vitamin $K_1$ (as phytonadione), vitamin $K_3$ (as menadione), paba (p-aminobenzoic acid), oholine, folio acid, biotin, allantoin biotin, retinol, inositol, allantoin calcium pantothenate, licithin (oholine di-$C_{16}$–$C_{18}$ glycerophosphate), cholesterol, PEG 16 soya sterol and mixtures thereof. Preferred vitamins are provitamin A, vitamin $B_1$, vitamin $B_2$, provitamin $B_5$, vitamin $B_6$, vitamin $B_{12}$ and vitamin E. Typical levels of vitamin are from about 0% to about 7% by weight of the composition.

Examples of amino acids useful in the present invention which provide the hair with valuable nutrition include alanine, β-alanine, N-methylalanine, N-phenylalanine, β-aminoisobutyric acid, β-aminobutyric acid, β-aminocaproic acid, ε-aminocaproic acid, glycine, N-ethylglycine, N-propylglycine, N-butylglycine, leucine, methionine, derivatives of methionine, sarcosine, serine, norvaline, tryptophan, lysine, aspartic acid, glutamic acid, iminodiacetic acid, keratin amino acids (keratin polypeptides), silk amino acids, allantoin acetyl methionine, allantoin, deoxyribonucleic acid, protamine/nucleic acid complex, nucleic acid and mixtures thereof. Preferred amino acids are glycine, methionine, sarcosine, keratin amino acids and silk amino acids. Typical levels of amino acid are from about 0% to about 7% by weight of the composition.

Examples of proteins useful in the present invention which provide the hair with valuable nutrition include hydrolyzed casein, hydrolyzed collagen (hydrolyzed animal protein), myristoyl hydrolyzed animal protein, hydrolyzed corn protein, hydrolyzed glycosaminoglycans, hydrolyzed keratin (keratin protein), hydrolyzed milk protein, hydrolyzed pea protein, hydrolyzed potato protein, hydrolyzed rice protein, hydrolyzed silk (silk protein), hydrolyzed soy protein, hydrolyzed vegetable protein, hydrolyzed wheat gluten, hydrolyzed wheat protein, hydrolyzed yeast protein and mixtures thereof. Preferred proteins are hydrolyzed collagen, hydrolyzed keratin protein, hydrolyzed silk protein and hydrolyzed soy protein. Typical levels of protein are from about 0% to about 7% by weight of the composition.

Examples of curl enhancing agents useful in the present invention which hold the hair in a waved or curled position include sodium, potassium, ammonium and alkanolammonium salts of thioglycolic acid, dithiodiglycolic acid, mercaptobutane sulfonic acid, thiolactic acid, thioparaconic acid, $\alpha,\alpha'$-dimercaptoadipic acid, formamidine sulfonic acid, $\beta$-mercaptoethane sulfonic acid as well as mercaptans such as $\alpha$-thiolglycerol, $\beta$-aminoethylmercaptan, mercaptoethyl alcohol, $\beta$-mercaptopionamide, mercaptoethylacetamide, thioglycolamide, methyl mercaptoethyl sulfone, mercaptoethyl nitrile, mercaptoethyl trifluoroacetamide-1,4-dimercapto-2,3-butanediol, cysteine and mixtures thereof. Still other examples of curl enhancing agents are those that liberate thioglycolic acid by decomposition or reaction in the presence of water just before or during actual use or are derivatives which are active curling agents by virtue of thier free thiol (SH) groups. Examples of compounds that liberate thioglycolic acid include carbaminyl thioglycolic acid, ditiocarbamyl derivatives, glycolic esters of di- and trithiocarbonic acid, thioglycolic hydrazide, monothiopropylene glycol, dithiopropyleneglycol, bisthioglycolic acid imide, heterocyclic compounds such as 2,4-thiazoledione, esters and amides of thioglycolic acid such as the thioglycolic esters of monomethyl-, dimethyl- and trimethylsilanol, thioglycolamide, $\beta$-aminoethylthioglycolamide, thioglycolic amides of amino acids and mixtures thereof. Further examples of curling agents are described in British Patent Nos. 0,771,627, 804, 077, and 0,824,426; German Patent Nos. 0,971,899, 1,067, 566 and 1,096,551; French Patent No. 1,174,561; Austrian Patent No. 0,210,071 and U.S. Pat. No. 3,148,126 all of which are incorporated herein by reference. Yet other examples of curl enhancing agents useful in the present invention are nonmercaptan reducing agents such as sodium sulfite, potassium sulfite, ammonium sulfite, sodium bisulfite, potassium bisulfite, ammonium bisulfite, guanidine bisulfite, alkyl or aryl substituted guanidinium bisulfites, phosphine derivatives such as tetrakishydroxymethylphosphonium chloride as well as the organic or inorganic salts of sulfurous acid and base/sulfite mixtures such as borax/ sodium hyposulfite, potassium carbonate/sodium sulfite, sodium bicarbonate/potassium sulfite, monoethanolamine/ potassium sulfite, ammonium carbonate/ammonium sulfite, sodium hydroxide/sodium bisulfite and mixtures thereof. The curling or waving action of sulfites and bisulfites can be accelerated through chemical additives such as quinones, polyphenols, urea, formamide and denaturants. In principle, waving or curling of the hair is accomplished by altering the chemical configuration of the hair. In general, curling agents such as those described above break or rearrange disulfide hair linkages which normally hold the hair in a straight configuration. Preferred curl enhancing agents are the sodium, potassium, ammonium salts of thioglycolic acid, sulfite, bisulfite and mixtures thereof. Typical levels of curl enhancing agent are from about 0% to about 7% by weight of the composition.

Examples of hair coloring agents which effect useful in the present invention include the temporary, semi-permanent or permanent organic, plant and metallic hair dyes. Examples of temporary organic hair dyes which areeasily removed by shampooing include brilliant blue FCF, indigotine IA, Alphazurine FG erioglaucine, indigo, fast green FCF, alizarin cyanine green, quinizarin green SS, naphthol green B, orange II, ammaranth, erythrosine,ponceau SX, Eosin YS, helindone pink CN, acid fuchsin D, napthalene red B, acid violet 6B, alizurol purple SS, tartrazine, sunset yellow FCF, quionoline yellow WS, quionoline yellow SS, metanti yellow, naphthol yellow S and mixtures thereof. Examples of semipermanent to permanent organic hair dyes that remain on the hair after several shampooing sessions include p-aminodiphenylamine, p-aminodiphenylamine hydrochloride, p-aminodiphenylamine sulfonic acid, 2-amino-5-hydroxytoluene, 5-amino-2-hydroxytoluene, 2-amino-4-nitrophenol, 4-amino-2-nitrophenol, o-aminophenol, p-aminophenol, m-aminophenol, p-aminophenol hydrochloride, p-aminophenol sulfate, 2-aminophenol-4-sulfonic acid, 4-aminophenol-2-sulfonic acid, N-(p-aminophenyl)glycine, o-anisidine, p,p'-diaminodiphenylamine, p,p'-diamminodiphenylamine sulfonate, p,p'-diaminodiphenylamine methane, 1,8-diaminonaphthalene, 2,4-diaminophenol, 2,4-diaminophenol hydrochloride, 2,4-diaminophenol-4-sulfonic acid, 3,4-diaminotoluene, N,N-di-sec-butyl-o-phenylenediamine, N,N-dimethyl-p -phenylenediamine, 4,6-dinitro-2-aminophenol, 5-nitro-o-aminophenol, 4-nitro-o-aminophenol, 5-nitro-2-aminophenol, 4-nitro-2-aminophenol, 2-nitro-o-aminophenol, N-(p-hydroxyphenyl) glycine, N-(p-hydroxy-5-nitrophenyl)glycine, p-methylamino phenol surfate, 1,5-naphthalenediol, 4-nitro-o-phenylenediamine, 2-nitro-p-phenylenediamine, nitro-m-phenylenediamine, N-(p-nitrophenyl)-glycine, o-phenylenediamine, m-phenylenediamine, m-phenylenediamine hydrochloride, p-phenylenediamine, p-phenylenediamine hydrochloride, p-phenylenediamine sulfate, 4-methoxy-6-methyl-m-phenylenediamine, 2,5-tolylenedia mine sulfate, m-tolylenediamine, p-tolylenediamine, p-tolylenediamine sulfate, 2,4,6-trinitroaniline, $\alpha$-naphtho, 2,4-diaminoanisole, 2,4-diaminoanisole sulfate, 2,4-diaminophenetole, hydroxyquinone, hydroxyhydroquinol, phloroglycinol, pyrocatechol, resorcinol, xylenol, 1,2,3-trihydroxybenzene (pyrogallol), 1,2,4-trihydroxybenzene, 2,4,5-trihydroxytoluene, 1,5-dihydroxynaphthalene 6-chloro-4-nitrophenol, 2,5-diaminopyridine, 2,6-diaminopyridine, 2,5-dihydroxypyridine, 2,6-dihydroxypyridine and mixtures thereof. Examples of plant hair dyes include henna (2-hydroxy-1,4-naphthoqunione), indigo, camomile (4',5,7-trihydroxyflavone), Roman camomile (anthemis nobills), German/Hungarian camomile (matricaria chamomilla), wood extracts such as brazilin from brazilwood, catechu (catechin/1,2-dihydroxybenzene mixture), fustic (2',3,4'5,7-pentahydroxyflavone/morintannic acid mixture), logwood (hydroxybrasilin), nutgalls, quercitron (3,3', 4'5,7-pentahydroxyflavone/quercitrin mixture), walnut (5-hydroxy-1,4-naphthoquinone/pyrogallol mixture), rhubarb, sage, black tea, chrysophanol (1,8-dLhydroxy-3-methylanthraquinone) and mixtures thereof. Typical levels hair coloring agent used in coloring shampoo preparations of the invention are from about 0% to about 7% by weight of the composition.

Examples of chelating or sequestering agents (builders) useful in the present invention include the sodium, potassium and ammonium salts of diphosphoric acid, triphosphoric acid, pyrophosphoric acid, orthophosphoric acid, hexametaphosphoric acid, 1-hydroxyethane-1,1-phosphonic acid, diethylenetriamine penta(methylene diphosphonic acid), ethylenediamine tetraacetic acid (EDTA), diethylenetriamine pentaacetic acid (DTPA), N-(hydroxyethyl) ethylenediamine triacetic acid (HEDTA), propylenediamine tetraacetic acid (PDTA), nitrilotriacetic acid (NTA), mellitic acid, 1,2,3,4-cyclopentane tetracarboxylic acid, succinic acid, lauryl succinic acid, oxydisuccinic acid (ODS), carboxymethyloxysuccinic acid, citric acid, lactic acid, tartaric acid, O-carboxymethyltartronic acid, polyacrylic acid, poly (α-hydroxyacrylic acid), poly(tetramethylene-1,2-dicarboxylic acid), poly(4-methoxytetramethylene-1,2-dicarboxylic acid), acrylic acid/maleic acid copolymer (polycarboxylate), acrylic acid/allyl alcohol copolymer (polycarboxylate), sodium PCA, gluconic acid, glucoheptonic acid, lactobionic acid, maltobionic acid and mixtures thereof. Preferred are the sodium, potassium and ammonium salts of ethylenediamine tetraacetic acid and diethylenetriamine pentaacetic acid. Typical levels of chelating or sequestering agent useful for complexing hard ions such as calcium and magnesium are from about 0% to about 6% by weight of the composition.

Examples of hydrotropes useful in the present invention include the sodium, potassium and ammonium salts of toluenesulfonic acid, ethylbenzenesulfonic acid, xylenesulfonic acid, cumenesulfonic acid, urea, and mixtures thereof. Preferred are the sodium, potassium and ammonium salts of toluenesulfonic acid and xylenesulfonic acid. Typical levels of hydrotrope useful in maintaining hair care composition clarity are from about 0% to about 6% by weight of the composition.

Examples of anti-lice agents useful in the present invention which provide control of lice infestations include lindane (gamma-benzene hexachloride), piperonyl butoxide, natural pyrethrins and synthetic pyrethroids. Natural pyrethrins are prepared from extracts of chrysanthemum flower heads and compositions comprising such ingredients are described more fully in EP Patent Applications 0,191,236 and 0,262,885; U.S. Pat. No. 4,668,666 all of which are incorporated herein by reference. Natural pyrethrins are esters formed by the combination of cyclopentolone alcohols (pyrethrolone, cinerolone and jasmolone) with chrysanthemic acid or pyrethric acid. The natural pyrethrin actives consists of a mixture of several isomeric esters such as pyrethrin I, pyrethrin II, cinerin I, cinerin II, jasmolin I and jasmolin II. The synthetic analogues of natural pyrethrins are called synethetic pyrethroids. These compounds are prepared by combining phenylacetic acid with esters of dichlorovinyl analogues of chrysanthemic acid. Preferred synthetic pyrethroids are phenothrin, permethrin and mixtures thereof. Although synthetic pyrethroids are generally more effective against lice than natural pediculicides, some synthetic pyrethroids are toxic to the subject being treated. To reduce the safety risks associated with synthetic pyrethroids, preparations are formulated with a combination of natural and synthetic pediculicides. The combination is considered to be more effective than either active alone. Preferred anti-lice agents are mixtures of synthetic pyrethroids and natural pyrethrins from about 12:1 to about 6:1, preferably from about 10:1 to about 8:1, most preferably from about 9:1 to about 8.5:1 by weight ratio. At these ratios, the hair care compositions remain stable even at elevated temperatures. Typical levels of anti-lice agent are from about 0% to about 5% by weight of the composition.

Examples of hair straighteners useful in the present invention which are used to lubricate and aid in fixing the hair in a straight position include fats, oils, waxes, arachidyl alcohol, behenyl alcohol, polyvinylpyrrolidones, thioglycolates, mercaptans, sulfites and silicones. Preferred are waxes such as polyethylene homopolymer waxes, microcrystalline wax, oxidized microcrystalline wax, low and high density oxidized waxes, castorwax, chemically modified waxes, spermaceti wax, beeswax, paraffin wax, petroleum wax, carnauba wax, candelilla wax, ozokerite wax, ceresine wax, glyceride wax and mixtures thereof. Typical levels of hair straighteners are from about 0% to about 5% by weight of the composition.

Examples of preservatives or antimicrobial agents that function as bactericides and/or fungicides useful in the present invention include glutaraldehyde, formaldehyde, paraformaldehyde, glyoxal, benzoic acid, salicylic acid, sorbic acid, dehydroacetic acid, benzyl alcohol, ethanol, 2-phenoxyethanol, chlorohexidine hydrochloride, triclosan, chloroacetamide, p-chloro-m-xylenol, 1-(3-chloroallyl)-3,5, 7-triaza-1-azoniaadamantane chloride, methyl paraben, propyl paraben, butyl paraben, benzyl paraben, imidazolidinyl urea, diazolidinyl urea, monomethylol dimethyl hydantoin (MDM hydantoin), dimethylol dimethyl hydantoin (DMDM hydantoin), iodopropylnyl butylcarbamate, 2-bromo-2-nitropropane-1,3-diol, 2-octyl-4-isothiazolin-3-one, 5-chloro-2-methyl-4-isothiazolin-3-one (methylchloroisothiazoline), 2-methyl-4-isothiazolin-3-one (methylisothaizoline) and dicocodimethylammonium chloride. Preferred is a combination of methyl isothiazoline and chloromethyl isothiazoline as described in U.S. Pat. No. 4,265,899 sold under the trade name Kathon CG by Rohm and Haas Company which is incorporated herein by reference. Typical levels of preservative used to control bacterial or fungal action are from about 0.001% to about 4% by weight of the composition.

Examples of antioxidants useful in the present invention which prevent the oxidation of certain ingredients by air and prevent the development of unpleasant, rancid odors include vitamin E (tocopherol), lecithin, wheat germ oil, sodium sulfite, sodium bisulfite, uric acid, propyl gallate, butylated hydroxyanisole (BHA), toluhydroquinone (THQ) sold as Tenox PG, Tenox BHA and Tenox THQ by Eastman Chemical Products Inc., and butylated hydroxytoluene (BHT) sold as Sustane BHT by UOP Process Division. Typical levels of antioxidant used to prevent oxidation, are from about 0% to about 4% by weight of the composition.

Examples of brightening agents (bleaching agents) used to bring out the highlights in dull hair or cause a shade change in hair color include hydrogen peroxide, sodium hypochlorite, potassium hypochlorite, ammonium hypochlorite, sodium bromate, potassium bromate, ammonium bromate, sodium percarbonate, potassium percarbonate, ammonium percarbonate, sodium perborate, potassium perborate, ammonium perborate, sodium perpyrophosphate, sodium perborosilicates, urea peroxide, melamine perhydrate, heavy metal ions and air mixtures such as copper/air, manganese/air, iron/air and mixtures thereof. A preferred brightening agent is hydrogen peroxide. Typical levels of brightening agent are from about 0% to about 3% by weight of the composition.

Examples of pH-control agents useful in the present invention include citric acid, tartaric acid, lactic acid, gluconic acid, lactobionic acid, glycolic acid, propionic acid, succinic acid, maleic acid, hydrochloric acid, phosphoric acid, nitric acid, sulfuric acid, formic acid, boric acid, acetic acid, benzoic acid, methylsulfonic acid, ethylsulfonic acid, palmitic acid, stearic acid, hexadecylamine, octadecylamine, dimethylstearylamine, stearylamidopropyldimethyl amine, sodium hydroxide, sodium carbonate, potassium hydroxide and mixtures thereof. The mount of pH-control agent used will be that which is sufficient to provide the desired pH.

Examples of buffering agents useful in the present invention which resist changes in their hydrogen-ion concentration resulting in a constant pH include mixtures of weak acids (or their salts) and weak bases (or their salts) such as citric acid/disodium phosphate, citric acid/sodium citrate, acetic acid/sodium acetate and citric acid/borax (sodium tetraborate). The composition of the salt pair is highly variable and one skilled in the art can with simple experimentation arrive at various salt pairs that will be functional and that will not detract from the overall compositions. The pH of the present compositions may be in the range of about 5 to about 9, preferably from about 5.5 to about 8.5, even more preferably from about 6 to about 8. In practice however, a shampoo composition or conditioning shampoo composition is adjusted to a pH of about less than 7 to provide a composition that is non-irritating and non-damaging to the hair, skin and eyes of the consumer. The mount of buffering agent used will be that which is sufficient to provide the desired buffered pH.

Examples of colorant which provide color to the hair care compositions of the invention include D&C blue #1, D&C blue #4, D&C brown #1, D&C green #5 through #8, D&C orange #4 through #11, D&C yellow #2 through #11, D&C red #6 through #40, D&C violet #2, FD&C blue #1, FD&C blue #2, FD&C blue #4, FD&C red #3, FD&C red #4, FD&C red #33, FD&C red #40, FD&C yellow #5, FD&C yellow #6, FD&C yellow #10, FD&C orange #4, FD&C green #3, carmine and mixtures thereof. Typical levels of colorant are from about 0% to about 2% by weight of the composition.

Other minor components include perfumes or fragrances which may be present from about 0.1% to about 4% by weight of the composition.

Many additional optional ingredients that are useful in the present invention are described in McCutcheon's, Detergents and Emulsifiers (Vol 1) and McCutcheon's, Functional Materials (Vol 2), 1992 Annual Edition, published by McCutcheon's MC Publishing Co. as well as the CTFA (Cosmetic, Toiletry and Fragrance Association) 1992 International Buyers Guide, published by CTFA Publications and OPD 1993 Chemical Buyers Directory 80th Annual Edition, published by Schnell Publishing Co. which are all incorporated herein by reference.

According to the present invention, a hair care composition comprises the following ingredients:
(a) from about 0.1% to about 40% by weight of the composition is a heteroatom containing alkyl aldonamide compound;
(b) from about 0% to about 45% by weight of the composition is a cosurfactant (cleansing agent) selected from the group consisting of soap, anionic, nonionic, amphoteric, zwitterionic, cationic and mixtures thereof;
(c) from about 0% to about 10% by weight of the composition is a hair conditioning agent;
(d) from about 0% to about 10% by weight of the composition is an auxiliary thickening agent;
(e) from about 0% to about 8% by weight of the composition is an antidandruff agent;
(f) from about 0% to about 7% by weight of the composition is a suspending agent;
(g) from about 0% to about 10% by weight of the composition is a hair styling agent;
(h) from about 0.1% to about 10% by weight of the composition is a viscosity control agent;
(i) from about 0% to about 10% by weight of the composition is an emulsifier/emollient/dispersant;
(j) from about 0% to about 10% by weight of the composition is a conditioning emollient off;
(k) from about 0% to about 10% by weight of the composition is a conditioning extract;
(l) from about 0% to about 10% by weight of the composition is a humectant;
(m) from about 0% to about 10% by weight of the composition is a solubilizing/clarifying agent;
(n) from about 0% to about 8% by weight of the composition is a sunscreen/UV absorber;
(o) from about 0% to about 7% by weight of the composition is an opacifier/pearlescent agent;
(p) from about 0% to about 7% by weight of the composition is a vitamin;
(q) from about 0% to about 7% by weight of the composition is an amino acid;
(r) from about 0% to about 7% by weight of the composition is a protein;
(s) from about 0% to about 7% by weight of the composition is a curl enhancing agent;
(t) from about 0% to about 7% by weight of the composition is a hair coloring agent;
(u) from about 0% to about 6% by weight of the composition is a chelating/sequestering agent;
(v) from about 0% to about 6% by weight of the composition is an hydrotrope;
(w) from about 0% to about 5% by weight of the composition is an anti-lice agent;
(x) from about 0% to about 5% by weight of the composition is a hair straightening agent;
(y) from about 0.001% to about 4% by weight of the composition is a preservative/antimicrobial agent;
(z) from about 0% to about 4% by weight of the composition is an antioxidant;
(aa) from about 0% to about 3% by weight of the composition is a brightening agent;
(bb) a pH control agent or buffering salt pair in an amount sufficient to provide a pH in the range of about 5 to about 9
(cc) from about 0% to about 2% by weight of the composition is a colorant;
(dd) from about 0.1% to about 4% by weight of the composition is a perfume/fragrance; and
(ee) the remainder is water In a more narrow aspect of the present invention, a hair care composition comprises the following ingredients:
(a) from about 0.2% to about 35% by weight of the composition is a heteroatom containing alkyl aldonamide compound;
(b) from about 0.1% to about 40% by weight of the composition is a cosurfactant (cleansing agent) selected from the group consisting of soap, anionic, nonionic, amphoteric, zwitterionic, cationic and mixtures thereof;
(c) from about 0% to about 8% by weight of the composition is a hair conditioning agent;
(d) from about 0% to about 8% by weight of the composition is an auxiliary thickening agent;
(e) from about 0% to about 6% by weight of the composition is an antidandruff agent;
(f) from about 0% to about 5% by weight of the composition is a suspending agent;
(g) from about 0% to about 8% by weight of the composition is a hair styling agent;
(h) from about 0.2% to about 8% by weight of the composition is a viscosity control agent;

(i) from about 0% to about 8% by weight of the composition is an emulsifier/emollient/dispersant;

(j) from about 0% to about 8% by weight of the composition is a conditioning emollient oil;

(k) from about 0% to about 8% by weight of the composition is a conditioning extract;

(l) from about 0% to about 8% by weight of the composition is a humectant;

(m) from about 0% to about 8% by weight of the composition is a solubilizing/clarifying agent;

(n) from about 0% to about 7% by weight of the composition is a sunscreen/UV absorber:

(o) from about 0% to about 6% by weight of the composition is an opacifier/pearlescent agent;

(p) from about 0% to about 5% by weight of the composition is a vitamin;

(q) from about 0% to about 5% by weight of the composition is an amino acid;

(r) from about 0% to about 5% by weight of the composition is a protein;

(s) from about 0% to about 5% by weight of the composition is a curl enhancing agent;

(t) from about 0% to about 5% by weight of the composition is a hair coloring agent;

(u) from about 0% to about 4% by weight of the composition is a chelating/sequestering agent;

(v) from about 0% to about 4% by weight of the composition is an hydrotrope;

(w) from about 0% to about 4% by weight of the composition is an anti-lice agent;

(x) from about 0% to about 3% by weight of the composition is a hair straightening agent;

(y) from about 0.002% to about 2% by weight of the composition is a preservative/antimicrobial agent;

(z) from about 0% to about 2% by weight of the composition is an antioxidant;

(aa) from about 0% to about 2% by weight of the composition is a brightening agent;

(bb) a pH control agent or buffering salt pair in an amount sufficient to provide a pH in the range of about 5.5 to about 8.5

(cc) from about 0% to about 1% by weight of the composition is a colorant;

(dd) from about 0.2% to about 3% by weight of the composition is a perfume/fragrance; and (ee) the remainder is water.

In an even more narrow aspect of the present invention, a hair care composition comprises the following ingredients:

(a) from about 0.3% to about 30% by weight of the composition is a heteroatom containing alkyl aldonamide compound;

(b) from about 0.2% to about 35% by weight of the composition is a cosurfactant (cleansing agent) selected from the group consisting of soap, anionic, nonionic, amphoteric, zwitterionic, cationic and mixtures thereof;

(c) from about 0% to about 6% by weight of the composition is a hair conditioning agent;

(d) from about 0% to about 6% by weight of the composition is an auxiliary thickening agent;

(e) from about 0% to about 4% by weight of the composition is an antidandruff agent;

(f) from about 0% to about 4% by weight of the composition is a suspending agent;

(g) from about 0.001% to about 35% by weight of the composition is an optional ingredient(s); and (h) the remainder is water.

In the most narrow aspect of the present invention, a hair care comprises the following ingredients:

(a) from about 0.4% to about 25% by weight of the composition is a heteroatom containing alkyl aldonamide compound;

(b) from about 0.3% to about 30% by weight of the composition is a cosurfactant (cleansing agent) selected from the group consisting of soap, anionic, nonionic, amphoteric, zwitterionic, cationic ahd mixtures thereof;

(c) from about 0% to about 6% by weight of the composition is a hair conditioning agent;

(d) from about 0% to about 6% by weight of the composition is an auxiliary thickening agent;

(e) from about 0% to about 3% by weight of the composition is an antidandruff agent;

(f) from about 0% to about 4% by weight of the composition is a suspending agent;

(g) from about 0.01% to about 25% by weight of the composition is an optional ingredient(s); and (h) the remainder is water.

Method of Manufacture

Aldonic acids, aldobionic acids and their lactones are prepared by microbial fermentation, chemical oxidation or enzymatic oxidation of sugars. (See for example, EP 142,725 (1985) to Saito, et al.; EP 232,202 (1986) and EP 233,816 (1987) to Fuertes et al.; JP 62/269728 (1987) to Kimura, et al.; Biotechnology Letters 6:487 (1984) to Chang, et al.; Biotechnology Letters 9:252 (1987) to Burdick, et al.; German Pat. No. 2,911,192 (1980) and U.S. Pat. No. 4,460,686 (1984) to Hartmeier and Appl. Microbiol. Biotechnol. 21:356 (1985) to Seiskari, et al. all of which are incorporated herein by reference). Examples of aldonic acids, aldobionic acids and their lactones suitable for the preparation of heteroatom containing alkyl aldonamide compounds include but are not limited to threonic acid, arabinonic acid, lyxonic acid, allonic acid, altronic acid, idonic acid, talonic acid, gluconic acid, galactonic acid, mannonic acid, lactobionic acid, maltobionic acid, cellobionic acid, gentiobionic acid, melibionic acid, glucopyranosyl-(1–5)-arabinonic acid, erythronolactone, ribonolactone, xylonolactone, gluconolactone, galactonolactone, mannonolactone, gulonolactone, glucoheptonolactone, lactobionolactone and maltobionolactone.

Heteroatom containing alkyl aldonamide compounds of the invention are prepared by reaction of the appropriate heteroatom containing amine with an aldonic acid or aldobionic acid (preferably with the corresponding aldonolactone or aldobionolactone) in an organic solvent (such as methanol) with or without an acid catalyst (such as methanesulfonic acid) at about 0° C. to about 90° C., preferably at about 20° C. to about 70° C., even more preferably at about 30° C. to about 60° C.

Heteroatom containing alkyl aldonamide salt compounds of the invention are prepared by reaction of an alkylaminoalkyl aldonamide or aldobionamide compound with an organic or inorganic acid in water or organic solvent at about 0° C. to about 100° C., preferably at about 20° C. to about 70° C., even more preferably at about 25° C. to about 55° C.

All raw materials such as D-gluconolactone, D-lactobionlactone, alkyloxypropylamine, alkylaminopropylamine and alkyloxypropylaminopropylamine are available in bulk and the end products are easily prepared by the commercially feasible process described above.

The compositions of the present invention can be prepared by adding the appropriate amount of water and admixing the active ingredients with appropriate stirring at about 18° C. to about 100° C., preferably from about 40° C. to about 80° C., even more preferably from about 50° C. to about 75° C. Ingredients may be added as a main mix, partial mix or as a premix. When the conditioning agent silicone is used, it is sometimes added as the last ingredient and it is sheared with a high shear mixer until the silicone particle size has an average diameter of 10 microns or less. All temperature sensitive components are added after the composition has cooled from about 18° C. to about 38° C. after which the composition is stirred until homogeneous. Commercial quantities of the compositions of the present invention can be easily prepared in a stainless steel or glass lined kettle equipped with a provision for agitation, heating and cooling. Processing may be continuous or batch wise, however cost savings may be further increased through continuous processing by virtue of economy of scale.

Hair Care Composition Types and Form

Hair care compositions are available in a variety of types and forms. A classification according to product type include, but are not limited to rinses, conditioners, shampoos, conditioning shampoos, antidandruff shampoos, antilice shampoos, coloring shampoos, curl maintenance shampoos, baby shampoos, herbal shampoos, hair loss prevention shampoos, hair growth promoting/stimulating shampoos, hairwave neutralizing shampoos, hair setting products, hair sprays, hair styling products, permanent wave products, hair straightening/relaxing products, mousses, hair lotions, hair tonics, hair promade products, brilliantines and the like. Preferred are the conditioners, shampoos, conditioning shampoos and antidandruff shampoos.

A classification according to product form would consist of aerosol, liquid, gel, creme, lotion, paste, granular, powdered, tablet and bar form. Preferred are the gel, creme (cream) and liquid forms.

Industrial Application and Use

The heteroatom containing alkyl aldonamide compounds of the invention are useful as surfactants that may be used alone or in combination with other surfactants to provide improved foam, viscosity, clarity and conditioning characteristics. More specifically, the heteroatom containing alkyl aldonamide compounds of the invention are useful as foam stabilizing agents, thickening agents, solubilizing agents and hair conditioning agents. In addition, it has been found that the heteroatom containing alkyl aldonamide compounds of the invention are also useful as gelling agents, foam boosting agents, detergency enhancing agents, soil release agents, lime soap dispersants, wetting agents and stabilizing agents. Furthermore, certain long chained heteroatom containing alkyl aldonamide compounds of the invention wherein the alkyl group contains 12 darbons or more (Kf>60° C.) were found to be useful as pearlescent agents (opacifiers), suspending agents, emollients (moisturizers/humectants) and emulsifying agents.

The non-heteroatom containing alkyl aldonamide compounds of the invention wherein the alkyl group contains 10 carbons or more have poor water solubility (Kf>60° C.) and were found to be useful as pearlescent agents (opacifiers) and suspending agents.

Home Application and Use

The present compositions are used in a conventional manner for cleaning, conditioning, waving, curling, relaxing or styling the hair. From about 0.1 g to about 15 g of a composition is applied to hair that has been thoroughly wetted with water. The composition is worked through the hair from about 30 seconds to about twenty minutes and then rinsed out.

The following Examples further describe and demonstrate the preferred embodiments that are within the scope of the present invention. The Examples are given solely for the purpose of illustration and are not to be construed as being limiting to the present invention since many variations are possible without departing from the spirit and scope of the invention.

EXAMPLES

Analysis of Monosaccharide Aldonamides by Gas Chromatography

Gas chromatography was found to be a convenient method for the examination of monosaccharide aldonamide compounds. The method of persilylation with hexamethyldisilazane (HMDS) and trimethylchlorosilane (TMCS) in pyridine is the simplest way for producing sufficienfiy stable and volatile derivatives for analysis. The mixture of both agents are more reactive than either reagent alone, and the by-products combine to form neutral ammonium chloride ($NH_4Cl$) or pyridine hydrochloride ($C_5H_5N.HCl$).

The purity of several monosaccharide aldonamides were determined and found to be 97–99.9%. All products were well separated from starting materials, however aldonamides with alkyl chains containing eighteen carbons or more were not volatile enough for analysis.

Approximately 7–10 mg of a monosaccharide aldonamide compound was treated with 1 ml of sil-prep reagent (pyridine:HMDS:TMCS=9:3:1) in a 1 dram stoppered vial containing a magnetic stirring bar. The mixture was stirred vigorously at room temperature for about a hour or longer prior to chromatography. The solution became cloudy owing to precipitation of $NH_4Cl$ and $C_5H_5N.HCl$ which was filtered through a CAMEO II 25 mm filter. From about 1.0 µl to about 1.1 µl of the resulting mixture was injected into the gas chromatograph.

All gas chromatography was conducted on a Hewlett Packard 5890 Series II Gas Chromatograph. All sample components were detected by a flame ionization detector using a split ratio of 100:1 and separated on a crosslinked 5% phenylmethyl silicone capillary column 25 m×0.32 mm×0.53 µm. The carrier gas was helium at 1 ml/minute and the temperature program was 3 minutes at 140° C. then 30° C./minute to 250° C. for 75 minutes.

Example 1 (No Heteroatom)

Preparation of Dodecyl D-Ribonamide (Used for Comparative Purposes)

A 200 ml four necked round bottom flask equipped with a condenser, addition funnel, thermometer and mechanical stirrer was charged with D-ribonon-1,4-lactone (15.0 g, 0.10 mole) and methanol (45 g, for 43% total solids). The suspension was heated to 40°–43° C. for 15 minutes and the heating mantle removed. Dodecylamine (18.8 g, 0.10 mole) containing methanol (5 ml) was added dropwise over ½ hour. The reaction mixture was allowed to cool to room temperature (about 21° C.) followed by stirring overnight to allow complete crystallization. The white, product was filtered, washed with methanol (3×20 ml) and dried under vacuum at 40°–45° C. giving 31.5 g (93% yield) of dodecyl D-ribonamtde with a melting point of 101°–102° C. and 99.9% purity.

Example 2 (No Heteroatom)

Preparation of Coco D-Gluconamide (Used for Comparative Purposes)

A 5 liter four necked round bottom flask equipped with a condenser, addition funnel, thermometer and mechanical stirrer was charged with D-glucono-1,5-lactone (480.0 g, 2.69 moles) and methanol (2752 g, for 27% total solids). The suspension was heated to 40°–50° C. for 15 minutes and the heating mantle removed. Cocoamine (538.0 g, 2.69 moles) containing methanol (80 ml) was added dropwise over ½ hour. The reaction mixture was allowed to cool to room temperature (about 21° C.) followed by stirring overnight to allow complete crystallization. The white product was filtered, washed with methanol (3×500 ml) and dried under vacuum at 40°–45° C. giving 947.0 g (93% yield) of coco D-gluconamide with a melting point of 147°–148° C.

Examples 3–22 (No Heteroatom)

The monosaccharide alkyl aldonamides (Examples 3–22) in Table 1 were prepared in a simfiar manner as in Example 2.

TABLE 1

Monosaccharide Alkyl Aldonamides
(Compounds Without Heteroatom for Comparative Purposes)

| Example | Structure | Attached Hydrocarbon | MP (°C.) | % Yield | % Purity |
|---|---|---|---|---|---|
| 3 | HOCH$_2$CHCHCHCHCNH— with OH, OH, OH, OH and C=O<br>D-Gluconamide | C$_7$H$_{15}$ | 159–160 | 93 | 99.7 |
| 4 | D-Gluconamide | C$_8$H$_{17}$ | 159–160 | 90 | 99.9 |
| 5 | D-Gluconamide | C$_9$H$_{19}$ | 158–159 | 92 | 99.9 |
| 6 | D-Gluconamide | C$_{10}$H$_{21}$ | 157–158 | 91 | 99.9 |
| 7 | D-Gluconamide | C$_{11}$H$_{23}$ | 156–157 | 92 | 99.9 |
| 8 | D-Gluconamide | C$_{12}$H$_{25}$ | 155–156 | 96 | 99.9 |
| 9 | L-Gluconamide | C$_{12}$H$_{25}$ | 154–155 | 95 | 99.9 |
| 10 | D-Gluconamide | C$_{13}$H$_{27}$ | 155–156 | 95 | 99.9 |
| 11 | D-Gluconamide | C$_{14}$H$_{29}$ | 154–155 | 92 | 97.4 |
| 12 | D-Gluconamide | C$_{16}$H$_{33}$ | 152–153 | 94 | 99.9 |
| 13 | D-Gluconamide | C$_{18}$H$_{37}$ | 147–149 | 94 | — |
| 14 | D-Gluconamide | Tallow | 141–142 | 91 | — |
| 15 | D-Gluconamide | Soya | 135–137 | 86 | — |
| 16 | D-Gluconamide | Oleyl | 130–131 | 86 | — |
| 17 | HOCH$_2$CHCHCHCHCNH— with OH, OH, OH, OH and C=O<br>D-Galactonamide | C$_{12}$H$_{25}$ | 187–188 (d) | 93 | 99.8 |
| 18 | HOCH$_2$CHCHCHCHCNH— with OH, OH, OH and C=O<br>L-Galactonamide | C$_{12}$H$_{25}$ | 187–188 (d) | 95 | 99.7 |
| 19 | HOCH$_2$CHCHCHCHCNH— with OH, OH, OH and C=O<br>L-Mannonamide | C$_{12}$H$_{25}$ | 159–160 | 95 | 99.6 |
| 20 | HOCH$_2$CHCHCHCHCHCNH— with OH, OH, OH, OH and C=O<br>D-Glycero-L-Mannoheptonamide | C$_{12}$H$_{25}$ | 195–197 (d) | 97 | 98.6 |
| 21 | HOCH$_2$CHCHCHCHCHCNH— with OH, OH, OH, OH and C=O<br>D-Glucoheptonamide | C$_{12}$H$_{25}$ | 156–157 | 93 | 99.9 |

TABLE 1-continued

Monosaccharide Alkyl Aldonamides
(Compounds Without Heteroatom for Comparative Purposes)

| Example | Structure | Attached Hydrocarbon | MP (°C.) | % Yield | % Purity |
|---------|-----------|---------------------|----------|---------|----------|
| 22 | OH      O<br> \|        ‖<br>HOCH$_2$CHCHCHCHCHCHCNH—<br>    \|  \|    \| \|   \|<br>   OH OH OHOH OH<br>D-Glucooctonamide | C$_{12}$H$_{25}$ | 156–157 | 93 | 99.9 | d = decomposition occurred during melting.

Example 23 (1 Ether Heteroatom)

Preparation of Octyl/Decyloxypropyl D-Ribonamide

A 250 ml four necked round bottom flask equipped with a condenser, additional funnel, thermometer and mechanical stirrer was charged with ribono-1,4-lactone (10.0 g, 0.07 mole) and methanol (37 g for 40% total solids). The suspension was heated to 40–°50° C. for 15 minutes and heating mantle removed. Octyl/decyloxypropylamine (14.6 g, 0.07 mole) was added dropwise over ½ hour and the reaction mixture stirred for six hours. The white product was filtered, washed with cold acetone (3×10 ml) and dried under vacuum at 40°–45° C. giving 14.0 g (57% yield) of octyl/decyloxypropyl D-ribonamide with a melting point of 71°–72° C. and 98.7% purity (62.8%/35.9%:C$_8$/C$_{10}$).

Examples 24–34 (1 Ether Heteroatom)

The monosaccharide alkyloxypropyl aldonamides (Examples 24–34) in Table 2 were prepared in a similar manner as in Example 23.

Example 35 (1 Ether Heteroatom)

Preparation of Octyl/Decyloxypropyl D-Glyceramide (No Solvent)

A 50 ml four necked round bottom flask equipped with a condenser, additional funnel, thermometer and mechanical stirrer was charged with methyl glycerate (5.1 g, 0.04 mole) and octyl/decyloxypropylamine (8.0 g, 0.04 mole). The reaction mixture was heated to 65° C. for 24 hours. Isopropanol was added and the product was recrystallized, filtered, washed with cold isopropanol (3×5 ml) and dried under vacuum at 40°–45° C. giving 3.4 g (29% yield) of octyl/decyloxypropyl D-glyceramide.

Example 36 (1 Ester Heteroatom)

Preparation of N-D-Gluconyl Dodecyl Glycinate

A 100 ml round bottom flask equipped with a condenser, addition funnel, thermometer and mechanical stirrer was charged with D-glucono-1,5-lactone (5.0 g, 0.03 mole) and isopropanol (35 g). The suspension was heated to 50° C. over 15 minutes. A mixture of glycine dodecyl ester

TABLE 2

Monosaccharide Alkyloxypropyl Aldonamides

| Example | Structure | Attached Hydrocarbon | MP (°C.) | % Yield | % Purity |
|---------|-----------|---------------------|----------|---------|----------|
| 24 | OH    O<br> \|     ‖<br>HOCH$_2$CHCHCHCHCNH—<br>    \|  \|   \|<br>  OH OH OH<br>D-Gluconamide | C$_3$H$_6$OCH$_2$CHC$_4$H$_9$<br>               \|<br>               C$_2$H$_5$ | 89–90 | 73 | 99.9 |
| 25 | D-Gluconamide | C$_3$H$_6$OC$_8$H$_{17}$/C$_{10}$H$_{21}$ | 119–120 | 83 | 63.7/35.6 |
| 26 | D-Gluconamide | C$_3$H$_6$O-Isodecyl | 96–101 | 83 | — |
| 27 | D-Gluconamide | C$_3$H$_6$OC$_{12}$H$_{25}$ | 129–130 | 96 | 99.5 |
| 28 | D-Gluconamide | C$_3$H$_6$O-Isotridecyl | 81–86 | 74 | — |
| 29 | D-Gluconamide | C$_3$H$_6$OC$_{12}$H$_{25}$ to C$_{15}$H$_{31}$ | 125–126 | 82 | — |
| 30 | D-Gluconamide | C$_3$H$_6$OC$_{14}$H$_{29}$ | 129–130 | 86 | 99.7 |
| 31 | OH    O<br> \|     ‖<br>HOCH$_2$CHCHCHCHCHCNH—<br>   \|  \|   \|   \|<br>  OH OH OH OH<br>D-Glucoheptonamide | C$_3$H$_6$OC$_8$H$_{17}$/C$_{10}$H$_{21}$ | 129–130 | 88 | 66.2/33.6 |
| 32 | D-Glucoheptonamide | C$_3$H$_6$O-Isodecyl | 100–105 | 85 | — |
| 33 | D-Glucoheptonamide | C$_3$H$_6$OC$_{12}$H$_{25}$ | 133–134 | 89 | 99.9 |
| 34 | D-Glucoheptonamide | C$_3$H$_6$OC$_{12}$H$_{25}$ to C$_{15}$H$_{31}$ | 128–129 | 75 | — | p-toluenesulfonate salt (11.7 g, 0.03 mole), triethylamine (2.9 g 0.03 mole) and isopropanol (20 g) were added dropwise over 15 minutes from an addition funnel. The reaction mixture was stirred rapidly for about 2 hrs and then cooled to room temperature. The white product was filtered, washed with chloroform (3×150 ml) and dried under high vacuum at 35° C. giving 7.2 g (61% yield) of N-D-gluconyl dodecyl glycinate with a melting point of 121°–122° C. and 98.6% purity.

Example 37 (1 Ester Heteroatom)

Preparation of N-D-Gluconyl Dodecyl Ester of Ethanolmine

A 100 ml round bottom flask equipped with a condenser, addition funnel, thermometer and mechanical stirrer was charged with D-glucono-1,5-lactone (7.0 g, 0.04 mole) and isopropanol (30 g). The suspension was heated to 65° C. over 15 minutes. A mixture of dodecyl ester of monoethanolamine p-toluenesulfonate salt (16.3 g, 0.04 mole), triethylamine amine (4.0 g 0.04 mole) and isopropanol (20 g) were added dropwise over 15 minutes from an addition funnel. The reaction mixture was stirred rapidly for about 6 hrs and then cooled to room temperature. The white product was filtered, washed with chloroform (3×150 ml) and dried under high vacuum at 35° C. giving 13.3 g (81% yield) of N-D-gluconyl dodecyl ester of ethanolamine with a melting point of 142°–143° C. and 97.4% purity.

Example 38 (1 Ester Heteroatom)

Preparation of N-D-Gluconyl Dodecyl DL-Alaninate

A 100 ml round bottom flask equipped with a condenser, addition funnel, thermometer and mechanical stirrer was charged with D-glucono-1,5-lactone (7.0 g, 0.04 mole) and isopropanol (30 g). The suspension was heated to 60° C. over 15 minutes. A mixture of DL-alanine dodecyl ester p-toluenesulfonate salt (16.9 g, 0.04 mole), triethylamine (4.0 g 0.04 mole) and isopropanol (20 g) were added dropwise over 15 minutes from an addition funnel. The reaction mixture was stirred rapidly for about 6 hrs and then cooled to room temperature. The white product was filtered, washed with chloroform (3×150 ml) and dried under high vacuum at 35° C. giving 12.5 g (73% yield) of N-D-gluconyl dodecyl alaninate with a melting point of 97°–98° C. and 98.8% purity.

Example 39 (1 Ester and 2 Ether Heteroatoms)

Preparation of N-D-Gluconyl Dodecyldi(oxyethyl) Glycinate

A 100 ml round bottom flask equipped with a condenser, addition funnel, thermometer and mechanical stirrer was charged with D-glueono-1,5-lactone (7.0 g, 0.04 mole) and isopropanol (30 g). The suspension was heated to 60° C. over 15 minutes. A mixture of glycine dodecyldi(oxyethyl) ester p-toluenesulfonate salt (20.2 g, 0.04 mole), triethylamine (4.0 g 0.04 mole) and isopropanol (20 g) were added dropwise over 15 minutes from an addition funnel. The reaction mixture was stirred rapidly for about 8 hrs and then cooled to room temperature. The white product was filtered, washed with chloroform (3×150 ml) and dried under high vacuum at 35° C. giving 8.9 g (43% yield) of N-D-gluconyl dodecyldi(oxyethyl) glycinate.

Example 40 (1 Amino Heteroatom)

Preparation of Cocoaminopropyl D-Gluconamide

A 1 liter round bottom flask equipped with a condenser, addition funnel, thermometer and mechanical stirrer was charged with D-glucono-1,5-lactone (100.0 g, 0.56 mole) and methanol (208 g for 55% total solids). The suspension was heated to 40° C. over 15 minutes and the heating mantle removed. Cocoaminopropylamine (153.8 g, 0.56 mole) was added dropwise over 15 minutes with rapid stirring. The reaction mixture was cooled and placed in a refrigerator at 0° C. overnight. The white product was filtered, washed with cold isopropanol (3×100 ml) and dried under high vacuum at 35° C. giving 206.0 g (81% yield) of cocoaminopropyl D-gluconamide with a melting point of 109°–111° C.

Example 41 (1 Amino Heteroatom)

Preparation of Hydrogenated Tallowaminopropyl D-Gluconamide

A 1 liter round bottom flask equipped with a condenser, addition funnel, thermometer and mechanical stirrer was charged with D-glucono-1,5-lactone (20.0 g, 0.11 mole) and methanol (56 g). The suspension was heated to 40° C. over 15 minutes and the heating mantle removed. Hydrogenated tallowaminopropylamine (36.0 g, 0.11 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 46.2 g (83% yield) of hydrogenated tallowaminopropyl D-gluconamide with a melting point of 112°–115° C.

Example 42 (1 Amino Heteroatom)

Preparation of Soyaaminopropyl D-Gluconamide

A 100 ml round bottom flask equipped with a condenser, addition funnel, thermometer and mechanical stirrer was charged with D-glucono-1,5-lactone (5.4 g, 0.03 mole) and methanol (7 g). The suspension was heated to 40° C. over 15 minutes and the heating mantle removed. Soyaaminopropylamine (10.0 g, 0.03 mole) was added dropwise over 15 minutes with rapid stirring. The reaction mixture was cooled arid placed in a refrigerator at 0° C. overnight. The white product was filtered, washed with cold isopropanol (3×100 ml) and dried under vacuum at 35° C. giving 14.1 g (92% yield) of soyaaminopropyl D-gluconamide with a melting point of 97°–100° C.

Example 42b (1 Amino Heteroatom)

Preparation of Oleylaminopropyl D-Gluconamide

A 500 ml round bottom flask equipped with a condenser, addition funnel, thermometer and mechanical stirrer was charged with D-glucono-1,5-lactone (25.0 g, 0.14 mole) and methanol (31 g). The suspension was heated to 40° C. over 15 minutes and the heating mantle removed. Oleylaminopropylamine (47.7 g, 0.14 mole) was added dropwise over 10 minutes and the reaction stirred for 6 hours. Acetone (300 ml) was added and the flask placed in a refrigerator overnight. The white solid was filtered, washed with cold acetone (3×50 g) and dried under vacuum at 35° C. giving 65.0 g (89% yield) of oleylaminopropyl D-gluconamide with a melting point of 100° C.–103° C.

Examples 43–44 (1 Amino and 1 Ether Heteroatom)

The monosaccharide alkyloxypropylaminopropyl aldonamides (Examples 43–44) in Table 3 were prepared in a similar manner as in Example 42.

TABLE 3

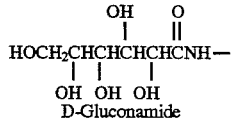

Example 45 (1 Amide Heteroatom)

Preparation of Hexylamido-2-Methylpentyl D-Gluconamide and Hexylamido-4-Methylpentyl D-Gluconamide A 100 ml round bottom flask equipped with a condenser, addition funnel, thermometer and mechanical stirrer was charged with D-glucono-1,5-lactone (6.7 g, 0.04 mole) and isopropanol (35 g). The suspension was heated to 50° C. over 25 minutes and the heating mantle removed. A mixture of hexylamido-2-methylpentylamine and hexylamido-4-methylpentylamine (45%/55%, 8.0 g, 0.04 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 7.6 g (52% yield) of hexylamido-2-methylpentyl D-gluconamide and hexylamido-4-methylpentyl D-gluconamide.

Example 46 (1 Amide and 1 Ether Heteroatom)

Preparation of Dodecyl to Pentadecyloxypropylacetamidopropyl D-Gluconamide

A 50 ml round bottom flask equipped with a condenser, addition funnel, thermometer and mechanical stirrer was charged with dodecyl to pentadecyloxypropylaminopropyl D-gluconamide (1.0 g, 2.93×10$^{-3}$ mole) and methanol (5 g). The suspension was heated to 40° C. and acetic anhydride (1.2 g, 1.18×10$^{-2}$ mole) was added dropwise over 15 minutes with rapid stirring. The reaction mixture was heated at 40° C. for 48 hours and the solvent, acetic acid and excess anhydride was removed by vacuum distillation (1.1 g, 98% yield). Water was added (3.6 g) to the reaction mixture and the product neutralized to a pH of about 7 with 0.1N sodium hydroxide solution. Hydrogen peroxide 3% (0.5 ml) was added and the product stirred for several hours. The sample is a pureable liquid ready for formulation.

Example 47 (1 Amide and 1 Ether Heteroatom)

Preparation of Dodecyl to Pentadecyloxypropylpropionamidopropyl D-Gluconamide

A 50 ml round bottom flask equipped with a condenser, addition funnel, thermometer, pH meter and mechanical stirrer was charged with dodecyl to pentadecyloxypropylaminopropyl D-gluconamide (1.0 g, 2.93×10$^{-3}$ mole) and water (4.0 g). Propionic arthydride (0.95 g, 7.33×10$^{-3}$ mole) is added portionwise along with 1N sodium hydroxide (which is added to maintain a pH of 7) at room temperature (21° C.). The mixture was stirred for 24 hours at room temperature and hydrogen peroxide 3% (0.5 ml) was then added. The sample is a pureable liquid ready for formulation.

Example 48 (1 Amide and 1 Ether Heteroatom)

preparation of Dodecyl to Pentadecyloxypropyltrifluoroacetamidopropyl D-Gluconamide A 50 ml plastic beaker equipped with an addition funnel, thermometer and stir bar was charged with dodecyl to pentadecyloxypropylaminopropyl D-gluconamide (1.0 g, 2.93×10$^{-3}$ mole) and methanol (15 g). The suspension was heated to 25° C. and trifioroacetic anhydride (1.2 g, 5.86× 10$^{-3}$ mole) was added dropwise over 15 minutes with rapid stirring. The reaction mixture was stirred at room temperature for 8 hours and the solvent, trifiuoroacetic acid and excess anhydride was removed by nitrogen sparge (1.4 g). Water (4.6 g) was added to the reaction mixture and the solution neutralized to a pH of about 7 with 0.1N sodium hydroxide solution. Sodium borohydride (0.03 g) was added and the product stirred for several hours. The sample is a pureable liquid ready for formulation.

Example 49 (1 Amide and 1 Ether Heteroatom)

Preparation of Dodecyl to Pentadecyloxypropylcaproamidopropyl D-Gluconamide

A 50 ml round bottom flask equipped with a condenser, addition funnel, thermometer and mechanical stirrer was charged with dodecyl to pentadecyloxypropylaminopropyl D-gluconamide (2.0 g, 5.86×10$^{-3}$ mole) and methanol (30 g). A separate 50 ml round bottom flask equipped with a stir bar and nitrogen blanket was charged with caproic acid (0.68 g, 5.86×10$^{-3}$ mole), triethylamine (0.60 g, 5.86×10$^{-3}$ mole) and diethyl ether (10 g). This mixture was stirred at 0° C. and ethyl chloroformate (0.64 g, 5.91×10$^{-3}$ mole) was added rapidly. After about 0.5 hour the resulting ethyl hydrogen carbonate caproic anhydride was filtered, washed with ether (3 ml) and added to methanolic solution containing dodecyI to pentadecyloxypropylaminopropyl D-gluconamide. The reaction mixture was stirred at 40° C. for 2 hours and the solvent was removed by vacuum distillation (2.3 g 91% yield). Water was added to the reaction mixture and the solution neutralized to a pH of about 7 with 0.1N sodium hydroxide solution. About 0.5 ml of 3% hydrogen peroxide was added and the product stirred for several hours. The sample is a pureable liquid ready for formulation.

Example 50 (1 Amide and 1 Ether Heteroatom)

Preparation of Dodecyl to Pentadecyloxypropylpropionamidopropyl D-Lactobionamide A 50 ml round bottom flask equipped with a condenser, addition funnel, thermometer and mechanical stirrer was charged with dodecyl to pentadecyloxypropylaminopropyl D-lactobionamide (3.0 g, 4.40×10$^{-3}$ mole) and methanol (20 g). The suspension was heated to 35° C. and propionic anhydride (1.7 g, 1.32×10$^{-2}$ mole) was added dropwise over 15 minutes with rapid stirring. The reaction mixture was heated at room temperature for 24 hours and the solvent, propionic acid and excess arthydride was removed by vacuum distillation (3.1 g, 95% yield).

Example 51 (1 Amide Heteroatom)

Preparation of Cocolauramidopropyl D-Lactobionamide

A 250 ml round bottom flask equipped with a condenser, addition funnel, thermometer and mechanical stirrer was charged with cocoaminopropyl D-lactobionamide (15.8 g, 2.57×10$^{-2}$ mole), methanol (200 ml) and lauric arthydride (15.0 g, 3.92×10$^{-2}$ mole). The mixture was stirred and heated at 50° C. for several hours, then at room temperature for several days. The solvent was removed by rotaevaporation and the mixture slurried with ethyl acetate (100 ml), filtered and washed with ethyl acetate (2×90 ml) followed by air drying. The solid residue was then extracted with butanol (400 ml) and acidic water (400 ml). The butanol layer was separated and extracted with water (2×200 ml) containing sodium chloride followed by drying over magnesium sulfate. The dry butanol layer was filtered and washed with additional butanol (2×50 ml) which was removed by vacuum distillation giving 9.7 g (48% yield) of cocolauramidopropyl D-lactobionamide Example 52 (No Heteroatom)

Preparation of Nonyl D-Lactobionamide (Used for Comparative Purposes)

A 100 ml round bottom flask equipped with a condenser, addition funnel, thermometer and mechanical stirrer was charged with D-lactobiono-1.5-lactone (100.0 g, 0.29 mole) and methanol (300 g). The suspension was heated to 50° C. over 15 minutes. Nonylamine (39.1 g, 0.27 mole) was added dropwise over 15 minutes with rapid stirring. The reaction mixture was cooled to room temperature and stirred overnight. The product was filtered, washed with cold methanol (1×100 ml) and dried under vacuum at 35° C.The product was then recrystallized in methanol giving 110.0 g (84% yield) of nonyl D-lactobionamide with a melting point of 149°–150° C.

Examples 53–66 (No Heteroatom)

The disaccharide alkyl aldonamides (Examples 53–66) in Table 4 were prepared in a similar manner as in Example 52.

TABLE 4

Disaccharide Alkyl Aldobionamides
(Compounds Without Heteroatom Used for Comparative Purposes)

| Example | Structure | Attached Hydrocarbon | MP (°C.) | % Yield | % Purity (HPLC) |
|---|---|---|---|---|---|
| 53 | D-Lactobionamide | $C_{10}H_{21}$ | 138–139 | 47 | 99.0 |
| 54 | D-Lactobionamide | $C_{11}H_{23}$ | 147–148 | 34 | 99.2 |
| 55 | D-Lactobionamide | $C_{12}H_{25}$ | 137–138 | 35 | 99.3 |
| 56 | D-Lactobionamide | $C_{13}H_{27}$ | 147–148 | 36 | 99.9 |
| 57 | D-Lactobionamide | $C_{14}H_{29}$ | 126–127 | 92 | 97.4 |
| 58 | D-Lactobionamide | $C_{15}H_{31}$ | 147–148 | 70 | 99.3 |
| 59 | D-Lactobionamide | $C_{16}H_{33}$ | 130–131 | 60 | 99.3 |
| 60 | D-Lactobionamide | $C_{18}H_{37}$ | 112–113 | 92 | — |
| 61 | D-Lactobionamide | Tallow | 109–111 | 65 | 97.5 |
| 62 | D-Lactobionamide | Oleyl | 104–106 | 71 | — |
| 63 | D-Maltobionamide | $C_{11}H_{23}$ | 109–110 | 26 | 99.7 |
| 64 | D-Maltobionamide | $C_{12}H_{25}$ | 114–115 | 26 | 99.7 |
| 65 | D-Maltobionamide | $C_{14}H_{29}$ | 118–119 | 31 | 99.7 |
| 66 | D-Maltobionamide | $C_{16}H_{33}$ | 122–123 | 67 | 98.0 |

Example 67 (1 Ether Heteroatom)

Preparation of Octyl/Decyloxypropyl D-Lactobionamide

A 2 liter round bottom flask equipped with a condenser, addition funnel, thermometer and mechanical stirrer was charged with D-lactobion-1,5-lactone (84.1 g, 0.25 mole), methanol (250 g for 35% total solids) and methanesulfonic acid (3 drops). The suspension was heated to 50° C. over 15 minutes and the heating mantle removed. Octyl/decyloxypropylamine (50.0 g, 0.25 mole) was added dropwise over 15 minutes with rapid stirring. The reaction mixture was cooled and stirred at room remperature overnight with 30% hydrogen peroxide (1 ml). Methanol was removed by vacuum distillation and acetone (1000 ml) added. The white product was filtered, washed with cold acetone (3×250 ml) and dried under high vacuum at 35° C. giving 112.2 g (84% yield) of octyl/decyloxypropyl D-lactobionamide with a melting point of 99–°101° C.

Example 68 (1 Ether Heteroatom)

Preparation of Dodecyloxypropyl D-Lactobionamide

A 3 liter round bottom flask equipped with a condenser, addition funnel, thermometer and mechanical stirrer was charged with D-lactobiono-1,5-lactone (180.0 g, 0.53 mole) and methanol (1100 ml). The suspension was heated to 50° C. over 15 minutes and the heating mantle removed. Dodecyloxypropylamine (128.8 g, 0.53 mole) was added dropwise over 30 minutes with rapid stirring. The reaction mixture was cooled and stirred at room temperature overnight. The white product was filtered, washed with cold acetone (2×400 ml) and dried under high vacuum at 40° C. giving 224.5 g (73% yield) of dodecyloxypropyl D-lactobionamide with a melting point of 117°–118° C.

Example 69 (1 Ether Heteroatom)

Preparation of Dodecyloxypropyl D-Maltobionamide

A 100 ml round bottom flask equipped with a condenser, addition funnel, thermometer and mechanical stirrer was charged with D-maltobiono-1,5-lactone (6.0 g, 0.02 mole) and methanol (25 ml). The suspension was heated to 50° C. over 15 minutes and the heating mantle removed. Dodecyloxypropylamine (4.3 g, 0.02 mole) was added dropwise over 30 minutes with rapid stirring. Acetone (50 ml) was added and the reaction mixture stirred at room temperature overnight. The white product was filtered, washed with cold acetone (3×30 ml) and dried under high vacuum at 30° C. giving 5.9 g (57% yield) of dodecyloxypropyl D-maltobionamide.

Example 70 (1 Ether Heteroatom)

Preparation of Dodecyl to Pentadecyloxypropyl D-Lactobionamide

A 2 liter round bottom flask equipped with a condenser, addition funnel, thermometer and mechanical stirrer was charged with D-lactobion-1,5-lactone (65.2 g, 0.19 mole), methanol (214 g for 30% total solids) and methanesulfonic acid (3 drops). The suspension was heated to 50° C. over 15 minutes and the heating mantle removed. Dodecyl to pentadecyloxypropylamine (50.0 g, 0.19 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 98.7 g (86% yield) of dodecyl to pentadecyloxypropyl D-lactobionamide with a melting point of 95°–98° C.

Example 71 (1 Ether Heteroatom)

Preparation of Tetradecyloxypropyl D-Lactobionamide

A 5 liter round bottom flask equipped with a condenser, addition funnel, thermometer and mechanical stirrer was charged with D-lactobiono- 1,5-lactone (500.0 g, 1.47 moles) and methanol (3000 ml). The suspension was heated to 50° C. over 30 minutes and the heating mantle removed. Tetradecyloxypropylamine (401.7 g, 1.47 mole) was added dropwise over 30 minutes with rapid stirring. The reaction mixture was cooled and stirred at room temperature overnight. The white product was filtered, washed with cold acetone (2×700 ml) and dried under high vacuum at 40° C. giving 656.1 g (73% yield) of tetradecyloxypropyl D-lactobionamide.

Example 72 (1 Ester Heteroatom)

Preparation of N-D-Lactobionyl Dodecyl Glycinate

A 50 ml round bottom flask equipped with a condenser, thermometer and mechanical stirrer was charged with dodecyl glycinate hydrochloride (9.0 g, 0.03 mole) and 2.0M methanolic ammonia (16 ml, 0.03 mole). The mixture was stirred at room temperature for 10 minutes and lactobiono-1,5-lactone (10.9 g, 0.03 mole) added followed by heating at reflux for 1 hour. Activated charcoal was then added and the reaction mixture stirred for 15 minutes at reflux. Activated charcoal was removed by filtration over a bed of celite while warm, washed with methanol (3×50 ml) and the flitrate allowed to cool to room temperature. The solvent was removed by rotary evaporation, the product washed with ethyl ether (2×100 ml), filtrered and dried in a vacuum oven at room temperature over phosphorous pentoxide giving 14.0 g (75% yield) of N-D-lactobionyl dodecyl glycinate.

Example 73 (1 Ester Heteroatom)

Preparation of N-D-Lactobionyl Dodecyl β-Alaninate

A 25 ml round bottom flask equipped with a condenser, thermometer and stir bar was charged with dodecyl β-alaninate hydrochloride (3.0 g, 0.01 mole) and 2.0M methanolic ammonia (5 ml, 0.01 mole). The mixture was stirred at room temperature for 10 minutes and lactobiono-1,5-lactone (3.5 g, 0.01 mole) added followed by heating at reflux for 1 hour. Activated charcoal was then added and the reaction mixture stirred for 15 minutes at reflux. Activated charcoal was removed by filtration over a bed of celite while warm, washed with methanol (3×25 ml) and the flitrate allowed to cool to room temperature. The solvent was removed by rotary evaporation, the product washed with ethyl ether (2×50 ml), filtrered and dried in a vacuum oven at room temperature over phosphorous pentoxide giving 4.3 g (70% yield) of N-D-lactobionyl dodecyl β-alaninate.

Example 74 (1 Amino Heteroatom)

Preparation of Cocoaminopropyl D-Lactobionamide

A 2 liter round bottom flask equipped with a condenser, addition funnel, thermometer and mechanical stirrer was charged with D-lactobion-1,5-lactone (66.4 g, 0.20 mole), methanol (175 g for 40 % total solids) and methanesulfontc acid (3 drops). The suspension was heated to 50° C. over 15 minutes and the heating mantle removed. Cocoaminopropylamine (50.0 g, 0.20 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 96.9 g (83% yield) of cocoaminopropyl D-lactobionamide with a melting point of 97°–101° C.

Example 75 (1 Amino Heteroatom)

Preparation of Oleylaminopropyl D-Lactobionamide

A 2 liter round bottom flask equipped with a condenser, addition funnel, thermometer and mechanical stirrer was charged with D-lactobion- 1,5-lactone (52.7 g, 0.15 mole), methanol (103 g for 50% total solids) and methanesulfonic acid (4 drops). The suspension was heated to 50° C. over 15 minutes and the heating mantle removed. Oleylaminopropylamine (50.0 g, 0.15 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 93.1 g (91% yield) of oleylaminopropyl D-lactobionamide with a melting point of 117°–118° C.

Example 76 (1 Amino Heteroatom) Preparation of Hydrogenated Tallowaminopropyl D-Lactobionamide A 1 liter round bottom flask equipped with a condenser, addition funnel, thermometer and mechanical stirrer was charged with D-lactobiono-1,5-lactone (20.0 g, 0.06 mole) and methanol (50 g): The suspension was heated to 40° C. over 15 minutes and the heating manfie removed. Hydrogenated tallowaminopropylamine (19.0 g, 0.06 mole) was added dropwise over 15 minutes with rapid stirring. The reaction mixture was cooled and placed in a refrigerator at 0° C. overnight. The white product was filtered, washed with cold isopropanol (3×100 ml) and dried under vacuum at 35° C. giving 46.2 g (84% yield) of hydrogenated tallowaminopropyl D-lactobionamide with a melting point of 135°–137° C.

Example 77 (1 Amino and 1 Ether Heteroatom)

Preparation of Dodecyl to Pentadecyloxypropylaminopropyl D-Lactobionamide

A 2 liter round bottom flask equipped with a condenser, addition funnel, thermometer and mechanical stirrer was charged with D-lactobion- 1,5-lactone (53.6 g, 0.16 mole), methanol (104 g for 50% total solids) and methanesulfonic acid (3 drops). The suspension was heated to 50° C. over 15 minutes and the heating mantle removed. Dodecyl to pentadecyloxypropylaminopropylamine (50.0 g, 0.16 mole) was added dropwise over 15 minutes with rapid stirring. The reaction mixture was cooled and stirred at room temperature overnight with 30% hydrogen peroxide (1 ml). Acetone (1000 ml) was added and the product stirred for about 2 hrs. The white product was filtered, washed with cold acetone (3×250 ml) and dried under high vacuum at 35° C. giving 91.3 g (88% yield) of dodecyl to pentadecyloxypropylaminopropyl D-lactobionamide with a melting point of 107°–111° C.

Example 78 (6 Ether Heteroatoms)

Preparation of Dodecyl to Pentadecyloxypropyl D-Gluconamide Pentaoxyethylene ether A 100 g autoclave equipped with a pressure gau,ge, mechanical stirrer, rupture disk, gas inlet and gas outlet was charged with dodecyl to pentadecyloxypropyl D-gluconamide (7.0 g, 1.60×10$^{-2}$ mole) dissolved in dimethylformamide (30 g) and potassium hydroxide (0.04 g, 8.0×10$^{-4}$ mole). The autoclave was flushed with a blanket of nitrogen and a mild vacuum pulled. Ethylene oxide (3.5 g, 8.0×10$^{-2}$ mole) was then added and the mixture heated to 70° C.–100° C. for seven hours. The mixture was then cooled and discharged into a 100 ml round bottom flask equipped with a distillation head, thermometer and mechanical stirrer containing 30% hydrogen peroxide (0.5 ml). The mixture was stirred for several hours at 30° C. and then neutralized with 0.1N hydrochloric acid followed by removal of dimethylformamide by vacuum distillation giving 10.7 g of dodecyl to pentadecyloxypropyl D-gluconamide pentaoxyethylene ether.

Example 79 (5 Ether Heteroatoms)

Preparation of Dodecyloxypropyl D-Maltobionamide

Tetraoxyethylene ether

A 100 g autoclave equipped with a pressure gauge, mechanical stirrer, rupture disk, gas inlet and gas outlet was charged with dodecyl oxypropyl D-maltobionamide (4.5 g, 7.49×10$^{-3}$ mole) dissolved in tert-butanol (20 g) and triethylamine (0.45 g, 4.45×10$^{-3}$ mole). The autoclave was flushed with a blanket of nitrogen and a mild vacuum pulled. Ethylene oxide (1.3 g, 3.0×10$^{-2}$ mole) was then added and the mixture heated to 70° C.–80° C. for seven hours. The mixture was then cooled and discharged into a 100 ml round bottom flask equipped with a distillation head, thermometer and mechanical stirrer containing 30% hydrogen peroxide (0.5 ml). The mixture was stirred for several hours at 30° C. and then neutralized with 1N hydrochloric acid followed by removal of tert-butanol by vacuum distillation giving 6.4 g of dodecyloxypropyl D-maltobionamtde tetraoxyethylene ether.

Example 80 (11 Ether Heteroatoms)

Preparation of Dodecyloxypropyl D-Lactobionamide Octaoxyethylene Dipropylene ether A 100 g autoclave equipped with a pressure gauge, mechanical stirrer, rupture disk, gas inlet and gas outlet was charged with dodecyl oxypropyl D-lactobionamide (7.0 g, 1.16×10$^{-2}$ mole) dissolved in dimethylformamide (30 g) and potassium hydroxide (0.03 g, 5.82×10$^{-4}$ mole). The autoclave was flushed with a blanket of nitrogen and a mild vacuum pulled. Ethylene oxide (4.1 g, 9.28×10$^{-2}$ mole) was then added and the mixture heated to 70° C.–100° C. for six hours. Propylene oxide (1.3 g, 2.32×10$^{-2}$ mole) was then added and the mixture heated to 70° C.–100° C. for additional five hours. The mixture was then cooled and discharged into a 100 ml round bottom flask equipped with a distillation head, thermometer and mechanical stirrer containing sodium borohydride (0.1 g). The mixture was stirred for several hours at 30° C. and then neutralized with 0.1N hydrochloric acid followed by removal of dimethylformamide by vacuum distillation giving 12.5 g of dodecyl oxypropyl D-lactobionamide octaoxyethylenedipropylene ether.

Examples 81–84

Krafft Points and Foam Heights

Krafft Points

The temperature at and above which surfactants begin to form micelles instead of precipitates is referred to as the Krafft point ($T_k$) and at this temperature the solubility of a surfactant becomes equal to its CMC (numerical value at which micelles are formed).

The appearance and development of micelles are important since detergency (solubilization of soils) by dishwashing liquids, shampoos, detergents, etc., depend on the formation of these aggregates in solution.

The Krafft point was measured by preparing 650 ml of a 0.1% or 1.0% dispersion of aldonamide in water by weight. If the surfactant was soluble at room temperature, the solution was slowly cooled to 0° C. If the suffactant did not precipitate out of solution, its Krafft point was considered to be <0° C. (less than zero). If it precipitated out of solution, the temperature at which precipitation occurs was taken as the Krafft point.

If the surfactant was insoluble at room temperature, the dispersion was slowly heated until the solution became homogeneous. It was then slowly cooled until precipitation occurred. The temperature at which the surfactant precipitates out of solution upon cooling was taken as the Krafft point.

Foam Height

Foam is an important attribute in many consumer products. It is one of the dominant factors that determines the commercial value of products such as dishwashing liquids, shampoos and soaps. Also, acceptabflity of many consumer products is closely related to the quality and texture of the foam they produce (psychological aspect).

Since most of the foaming data on suffactants is typically obtained by the Ross-Miles Foam Height Assay (Ross, J. and Miles, G. D. Am Soc. for Testing Material Method D1173-63 Philadelphia, Pa. (1953); Oil & Soap (1958) 62:1260) the foaming ability of these surfactants were acquired using this method.

In the Ross-Miles method, 200 mL of a suffactant solution contained in a pipette of specified dimensions with a 2.9

-mm-i.d. orifice is allowed to fall 90 cm onto 50 mL of the same solution contained in a cylindrical vessel maintained at a given temperature by means of a water jacket. The height of the foam produced in the cylindrical vessel is read immediately after all the solution has run out of the pipette and then again after a given amount of time.

Using this method, the foam production (initial foam height in mm) and foam stability (final foam height after 10 minutes in mm) were measured at 0.1% aldonamtde concentration, 40° C. and 0 ppm (parts per million) hardness. Aldonamides that were not soluble at 40° C. were measured at about 5°–10° C. above their Krafft points.

In order to show the unexpected enhancement in solubility and foam, applicants compared a series of heteroatom containing alkyl aldonamlde compound to a series of alkyl aldonamide compound having no heteroatom in the attached aliphatic group The results are as follows:

Example 81

Monosaccharide Aldonamides Containing Four Hydroxyl Groups

| Entry | Compound | Average # of Hydrocarbons | Foam Height Initial (mm) | Foam Height Final (mm) | Krafft Point (0.1%), °C. |
|---|---|---|---|---|---|
| A | $C_{12}$ Ribonamide (Comparative) | 12 | 184 | 103 | 54 |
| B | $C_8/C_{10}$ Oxypropyl D-Ribonamide | 11.6 | 217 | 200 | 10 |

Example 82

Monosaccharide Aldonamides Containing Five Hydroxyl Groups

| Entry | Compound | Average # of Hydrocarbons | Foam Height Initial (mm) | Foam Height Final (mm) | Krafft Point (0.1%), °C. |
|---|---|---|---|---|---|
| C | $C_7$ D-Gluconamide (Comparative) | 7 | 0 | 0 | <0 |
| D | $C_8$ D-Gluconamide (Comparative) | 8 | 0 | 0 | 12 |
| E | $C_9$ D-Gluconamide (Comparative) | 9 | 0 | 0 | 53 |
| F | $C_{10}$ D-Gluconamide (Comparative) | 10 | 199 | 6 | 75 |
| G | $C_{11}$ D-Gluconamide (Comparative) | 11 | X | X | 87 |
| H | $C_{12}$ D-Gluconamide (Comparative) | 12 | X | X | 91 |
| I | $C_{12}$ L-Gluconamide (Comparative) | 12 | X | X | 91 |
| J | $C_{12}$ D-Galactonamide (Comparative) | 12 | - Insoluble - | | >100 |
| K | $C_{12}$ L-Galactonamide (Comparative) | 12 | - Insoluble - | | >100 |
| L | $C_{12}$ L-Mannonamide (Comparative) | 12 | - Insoluble - | | >100 |
| M | $C_{14}$ D-Gluconamide (Comparative) | 14 | - Insoluble - | | >100 |
| N | $C_{16}$ D-Gluconamide (Comparative) | 16 | - Insoluble - | | >100 |
| O | $C_{18}$ D-Gluconamide (Comparative) | 18 | - Insoluble - | | >100 |
| P | Ethylhexyloxypropyl D-Gluconamide | 11 | 0 | 0 | <0 |
| Q | $C_8/C_{10}$ Oxypropyl D-Gluconamide | 11.6 | 212 | 165 | 48 |
| R | Iso $C_{10}$ Oxypropyl D-Gluconamide | 13 | 213 | 206 | <0 |
| S | $C_{12}$ Oxypropyl D-Gluconamide | 15 | 200 | 110 | 61 |
| T | Iso $C_{13}$ Oxypropyl D-Gluconamide | 16 | 190 | 100 | <15 |
| U | $C_{12}$–$C_{15}$ Oxypropyl D-Gluconamide | 16.3 | 200 | 110 | 58 |
| V | $C_{14}$ Oxypropyl D-Gluconamide | 17 | 203 | 101 | 53 |
| W | N—D-Gluconyl $C_{12}$ Glycinate | 14 | 183 | 107 | 63 |
| X | N—D-Gluconyl $C_{12}$ Ester of Ethanolamine | 14 | 185 | 111 | 63 |
| Y | N—D-Gluconyl $C_{12}$ DL-Alaninate | 15 | 197 | 112 | 53 |
| Z | N—D-Gluconyl $C_{12}$ Di(oxyethyl) Glycinate | 18 | 203 | 169 | <0 |
| AA | Cocoaminopropyl D-Gluconamide | 16 | 186 | 182 | 18 |
| BB | Soyaaminopropyl D-Gluconamide | 20.7 | 160 | 88 | <18 |
| CC | Oleylaminopropyl D-Gluconamide | 21 | 158 | 84 | <0 |
| DD | ISO $C_{13}$ Oxypropylaminopropyl D-Gluconamide | 19 | 180 | 178 | <0 |
| EE | $C_{12}$–$C_{15}$ Oxypropylaminopropyl D-Gluconamide | 19.3 | 180 | 176 | <0 |

X indicates low water solubility, foam height cannot be measured.

Example 83

Monosaccharide Aldonamides Containing Six to Seven Hydroxyl Groups

| Entry | Compound | Average # of Hydrocarbons | Foam Height Initial (mm) | Foam Height Final (mm) | Krafft Point (0.1%), °C. |
|---|---|---|---|---|---|
| FF | $C_{12}$ D-Glucooctonamide (Comparative) | 12 | X | X | 86 |
| GG | $C_{12}$ D-Glycero-L-Mannoheptonamide (Comparative) | 12 | - Insoluble - | | >100 |
| HH | $C_{12}$ D-Glucoheptonamide (Comparative) | 12 | X | X | 91 |
| II | $C_8/C_{10}$ Oxypropyl D-Glucoheptonamide | 11.7 | 221 | 90 | 60 |
| JJ | Iso $C_{10}$ Oxypropyl D-Glucoheptonamide | 13 | 215 | 204 | 18 |
| KK | $C_{12}$ Oxypropyl D-Glucoheptonamide | 15 | 245 | 80 | 73 |
| LL | $C_{12}$–$C_{15}$ Oxypropyl D-Glucoheptonamide | 16.3 | 239 | 97 | 68 |

X indicates low water solubility, foam height cannot be measured.

Example 84

Disaccharide Aldonamides Containing Eight Hydroxyl Groups

| Entry | Compound | Average # of Hydrocarbons | Foam Height Initial (mm) | Foam Height Final (mm) | Krafft Point (0.1%), °C. |
|---|---|---|---|---|---|
| MM | $C_9$ D-Lactobionamide (Comparative) | 9 | 0 | 0 | 42 |
| NN | $C_{11}$ D-Lactobionamide (Comparative) | 11 | 0 | 0 | 61 |
| OO | $C_{12}$ D-Lactobionamide (Comparative) | 12 | 153 | 20 | 38 |
| PP | $C_{13}$ D-Lactobionamide (Comparative) | 13 | 145 | 78 | 70 |
| QQ | $C_{14}$ D-Lactobionamide (Comparative) | 14 | 141 | 59 | 18 |
| RR | $C_{14}$ D-Maltobionamide (Comparative) | 14 | 145 | 140 | 46 |
| SS | $C_{15}$ D-Lactobionamide (Comparative) | 15 | X | X | 84 |
| TT | $C_{16}$ D-Lactobionamide (Comparative) | 16 | 95 | 95 | 64 |
| UU | $C_{18}$ D-Lactobionamide (Comparative) | 18 | X | X | 82 |
| VV | $C_8/C_{10}$ Oxypropyl D-Lactobionamide | 11.6 | 168 | 158 | <0 |
| WW | $C_{12}$ Oxypropyl D-Lactobionamide | 15 | 165 | 154 | <0 |
| XX | $C_{12}$ Oxypropyl D-Maltobionamide | 15 | 163 | 155 | <0 |
| YY | $C_{12}-C_{15}$ Oxypropyl D-Lactobionamide | 16.3 | 166 | 155 | <0 |
| ZZ | $C_{14}$ Oxypropyl D-Lactobionamide | 17 | 163 | 154 | <0 |
| AAA | D-Lactobionyl $C_{12}$ Glycinate | 14 | 161 | 153 | <0 |
| BBB | D-Lactobionyl $C_{12}$ β-Alaninate | 15 | 159 | 152 | <0 |
| CCC | Cocoaminopropyl D-Lactobionamide | 16 | 171 | 168 | <0 |
| DDD | Oleylaminopropyl D-Lactobionamide | 18 | 169 | 165 | <0 |
| EEE | $C_{12}-C_{15}$ Oxypropyl-aminopropyl D-lactobionamide | 19.3 | 173 | 169 | <0 |

X indicates low water solubility, foam height cannot be measured.

Detailed Discussion of Examples 81–84

From the above Tables (81–83), it can be clearly seen that monosaccharide alkyl aldonamide compounds lacking a heteroatom in the hydrocarbon chain (A, C-O, FF-HH) provide little or no foam and have significantly higher Krafft points. While not wishing to be bound by theory, it is believed that these compounds pack closely in the solid state through strong amide/hydroxyl hydrogen bonding and strong hydrocarbon Van der Waal forces. The net result is an unfavorable heat of hydrailLion, high Krafft point, low or no water solubility and a poor foaming profile. Changing the stereochemistry (I-L) or increasing the hydrophilicity (FF-HH) of the sugar head group (by hydroxyl group addition) results in little or no improvement. However, monosaccharide alkyl aldonamide compounds that contain a heteroatom such as an oxygen (B, Q-V, II-LL), an ester (W-Y), an ester/oxygen combination (Z), a nitrogen (AA-CC) or a nitrogen/oxygen combination (DD, EE) in the hydrocarbon chain are believed to pack more loosely (favorably) in the solid state thereby resulting in a low Krafft point, increased water solubility and superior foaming profile. Also, closer comparison reveals that monosaccharide aldonamide compounds containing a heteroatom in the hydrocarbon chain unexpectedly allow the introduction of the same or greater alkyl chain length without sacrificing foaming and solubility characteristics. (Compare the average number of hydrocarbons of G-O to Q-EE and HH to II-LL).

Disaccharide alkyl aldobionamide compounds in Table 84 (MM-UU) tend to have reasonable Krafft points and foaming profiles. However, the addition of a heteroatom such as an oxygen (VV-ZZ), an ester (AAA, BBB), a nitrogen (CCC, DDD) or a nitrogen/oxygen combination in the hydrocarbon chain results in extremely low Krafft points (<0° C.), increased water solubility and enhanced foaming profile. Again, closer comparison reveals that disaccharide aldobionamide compounds containing a heteroatom in the hydrocarbon chain unexpectedly allow the introduction of the same or greater alkyl chain length without sacrificing foaming and solubility characteristics. (Compare the average number of hydrocarbons of OO-UU to VV-EE).

Thus, the ability of significantly improving the water solublity and foaming profile of an alkyl aldonamide or aldobionamide compound by heteroatom introduction is a significant achievement. These findings are quite unusual and unexpected, since monosaccharide alkyl aldonamide compounds are generally considered to be poor surfactants with poor emulsifing properties that are insoluble in water with little or no foaming capability.

Example 85

Foam Stability and Enhancement of Anionic Surfactants with Heteroatom Containing Alkyl Aldonamide Compofinds In order to demonstrate the improved ability of heteroatom containing alkyl aldonamide compounds to stabilize and enhance foam, several surfactant compositions were prepared and the foam height measured under the following conditions:

Foam Stability and Enhancement Conditions

| | |
|---|---|
| Temperature | 35° C. |
| pH | 10 |
| Sodium Triphosphate 6 $H_2O$ | $2.5 \times 10^{-3}$ M (1.2 g/L) |
| Sodium Carbonate | $3.9 \times 10^{-3}$ M (0.4 g/L) |
| Calcium Chloride (Hardness) | $2.0 \times 10^{-3}$ M (0.2 g/L) |
| Surfactant = $C_8/C_{10}$ OPG: $C_{12}$ LAS | 10:90 mole % |
| Surfactant = $C_{12}$ Amide DEA: $C_{12}$ LAS | 10:90 mole % |
| Surfactant = $C_{12}$ Amide MEA: $C_{12}$ LAS | 10:90 mole % |
| Surfactant = Cocopolyglucoside: $C_{12}$ LAS | 10:90 mole % |
| Surfactant = $C_{12}$ Gluconamide: $C_{12}$ LAS | 10:90 mole % |
| Total Surfactant Concentration | $5.0 \times 10^{-3}$ M |
| Triolein/Calcium Stearate (90/10 by wt.) | 1 g/L |

The triolein/calcium stearate mixture was dispersed to the above solutions using a high speed shear mixer at 60° C. and then cooled to 35° C. The triolein/calcium stearate mixture represents an extreme type of antifoam behavior found in sebum soil.

The foaming behavior of the above surfactants was determined by the Ross-Miles Foam Height Assay (Ross, J. and Miles, G. D. Am Soc. for Testing Material Method Dl173-63 Philadelphia, Pa. (1953); Oil & Soap (1958) 62:1260) and the cylinder shaking method.

In the Ross-Miles method, 200 mL of a surfactant solution contained in a pipette of specified dimensions with a 2.9-mm-i.d. orifice is allowed to fall 90 cm onto 50 mL of the same solution contained in a cylindrical vessel maintained at a given temperature by means of a water jacket. The height of the foam produced in the cylindrical vessel is read after 30 minutes has elapsed.

In the cylinder shaking method, 25 ml of a surfactant solution is placed in a 250 ml graduated cylinder and shook for 10 seconds. The height of the foam produced in the cylinder is read after 30 minutes has elapsed.

The foam stability and enhancement of the heteroatom containing alkyl aldonamides was determined using a 0:100 and 10:90 mole percent of a solution of $C_8/C_{10}$ oxypropyl D-gluconamide ($C_8/C_{10}$ OPG): sodium dodecyl benzene sulfonate ($C_{12}$ LAS) and compared to identical solutions of lauramide diethanolamine ($C_{12}$ amide DEA): sodium dodecyl benzene sulfonate, coconut polyglucoside: sodium dodecyl benzene sulfonate, lauramide monoethanolamine ($C_{12}$ amide MEA): sodium dodecyl benzene sulfonate and dodecyl D-gluconamide ($C_{12}$ Gluc): sodium dodecyl benzene sulfonate in the presence and absence of the triolein/calcium stearate antifoam. The results were determined by cylinder shaking and are as follows:

Foam Stability and Enhancement of Sodium Dodecyl Benzene Sulfonate with Various Foam Stabilizers/Enhancers

|  | Foam Height (mm) | |
| --- | --- | --- |
| Mole % | No Antifoam | With Antifoam |
| $C_8/C_{10}$ OPG: $C_{12}$ LAS | 195 | 85 |
| $C_{12}$ amide DEA: $C_{12}$ LAS | 190 | 30 |
| Coconut polyglucoside: $C_{12}$ LAS | 160 | 28 |
| $C_{12}$ amide MEA: $C_{12}$ LAS | 150 | 30 |
| $C_{12}$ LAS (Control) | 160 | 20 |
| $C_{12}$ Gluc: $C_{12}$ LAS (Comparative) | Insoluble | Insoluble |

From the above table it can be seen that $C_8/C_{10}$ oxypropyl D-gluconamide was found to enhance as well as stabilize the foam of a typical anionic surfactant. This enhancement was better than lauramide diethanolamine, coconut polyglucoside, lauramide monoethanolamine, dodecyl D-gluconamide and sodium dodecyl benzene sulfonate (alone) especially in the presence of triolein/calcium stearate antifoam. This finding suggests that the heteroatom containing alkyl aldonamide compounds of the present invention are useful as effective foam stabilizers and foam enhancers.

The foam stability and enhancement of the heteroatom containing alkyl aldonamides was further determined using a 10:90 mole percent solution of $C_8/C_{10}$ oxypropyl D-gluconamide ($C_8/C_{10}$ OPG): sodium dodecyl benzene sulfonate ($C_{12}$ LAS) and compared to identical solutions of dodecyl D-gluconamide ($C_{12}$ Gluc): sodium dodecyl benzene sulfonate in the presence and absence of the triolein/calcium stearate antifoam. The results were determined by the Ross-Miles method and are as follows:

Foam Stability and Enhancement of Sodium Dodecyl Benzene Sulfonate with Heteroatom Containing Alkyl Aldonamide Compounds

|  | Foam Height (mm) | |
| --- | --- | --- |
| Mole % | No Antifoam | With Antifoam |
| $C_8/C_{10}$ OPG: $C_{12}$ LAS | 147 | 98 |
| $C_{12}$ LAS (Control) | 131 | 61 |
| $C_{12}$ Gluc: $C_{12}$ LAS (Comparative) | Insoluble | Insoluble |

From the above table it can be seen that $C_8/C_{10}$ oxypropyl D-gluconamide was found to enhance as well as stabilize the foam of a typical anionic surfactant. This enhancement was better than dodecyl D-gluconamide and sodium dodecyl benzene sulfonate alone especially in the presence of triolein/calcium stearate antifoam. This finding suggests that the heteroatom containing alkyl aldonamide compounds of the present invention are useful as effective foam stabilizers and foam enhancers.

Example 86

Foam Stability and Enhancement of Anionic Surfactants with Heteroatom Containing Alkyl Aldonamide Compounds In order to further demonstrate the improved ability of heteroatom containing alkyl aldonamide compounds to stabilize and enhance foam, several prototype shampoo compositions were prepared and their foam stability and enhancement measured at 45° C. by the Ross-Miles Foam Height assay. The results were compared to identical compositions comprising petrochemitcally derived foam stabilizing agents, in particular, alkanolamides and alcohol ethoxylates. The prototype shampoo composition is as follows:

Prototype Shampoo Compositions Comprising Sodium/Ammonium Lauryl Surfate and Heteroatom Containing Alkyl Aldonamide Compounds

| Ingredients | Wt | Function |
| --- | --- | --- |
| Sodium Lauryl Sulfate | 9.0% | Cleansing Agent |
| Ammonium Lauryl Sulfate (30% Active) | 15.0% | Cleansing Agent |
| Heteroatom Containing Alkyl Aldonamide, Alkanolamide or Alcohol Ethoxylate | 4.0% | Foam Stabilizer/Thickener |
| Glycerine | 3.0% | Solubilizer |
| Sodium Chloride | 0.9% | Viscosity Cobuilder |
| Methyl Cellulose (25 cp at 2%) | 0.4% | Viscosity Cobuilder |
| Disodium EDTA | 0.1% | Sequestering Agent |
| Methyl Paraben | 0.1% | Preservative |
| Propyl Paraben | 0.01% | Preservative |
| Distilled Water | 67.49% |  |
| Total | 100.0% |  |

The compositions were prepared by admixing the ingredients in listed order with rapid stirring at 45°–50° C. Foam stability and enhancement were measured at 0.1% based on sodium and ammonium lauryl sulfate (0.16% total solids) at 45° C. and 0 or 120 parts per million (ppm) hardness calcium:magnesium ion 2:1. The results are set forth below:

Foam Stability and Enhancement of Sodium/Ammonium Lauryl Sulfate with Heteroatom Containing Alkyl Aldonamide Compounds at 0 ppm Hardness

| Formulation (Example 86) | Initial FH (mm) | Final FH after 60 Min. (mm) |
| --- | --- | --- |
| $C_8/C_{10}$ Oxypropyl D-Gluconamide | 187 | 150 |
| Lauramide DEA | 190 | 151 |
| Cocoamide MEA | 178 | 70 |
| Neodol 91-6 | 174 | 6 |
| No Foam Stabilizer (Control) | 149 | 5 |

Foam Stability and Enhancement of Sodium/Ammonium Lauryl Sulfate with Heteroatom Containing Alkyl Aldonamide Compounds at 120 ppm Hardness

| Formulation (Example 86) | Initial FH (mm) | Final FH after 60 Min. (mm) |
|---|---|---|
| $C_8/C_{10}$ Oxypropyl D-Gluconamide | 161 | 128 |
| Lauramide DEA | 159 | 126 |
| Cocoamide MEA | 148 | 53 |
| Neodol 91-6 | 145 | 5 |
| No Foam Stabilizer (Control) | 127 | 5 |

From the above table it can be seen that $C_8/C_{10}$ oxypropyl D-gluconamide was found to enhance as well as stabilize the foam of a typical prototype shampoo formulation. This enhancement was comparable to lauramide diethanolamine and better than cocoamide monoethanolamine or Neodol 91-6 ($C_9$–$C_{11}$ alcohol ethoxylate with 6 moles of ethylene oxide) especially in the presence of hardness. This finding suggests that the heteroatom containing alkyl aldonamide compounds of the present invention are useful as effective foam stabilizers and foam enhancers.

Example 87

Clarity Enhancement of Heteroatom Containing Alkyl Aldonamide Compounds

In order to demonstrate the improved ability of heteroatom containing alkyl aldonamide compounds to enhance clarity, several prototype shampoo compositions were prepared and their clarity measured at room temperature (~21° C.). The prototype shampoo composition is as follows:

Prototype Shampoo Compositions Comprising Sodium Lauryl Sulfate and Alkyl Aldonamide Compounds (Comparative)

| Ingredients | Wt | Function |
|---|---|---|
| Sodium Lauryl Sulfate | 15.0% | Cleansing Agent |
| Alkyl Aldonamide | 3.0–5.0% | Comparative |
| Sodium Chloride | 2.0% | Viscosity Cobuilder |
| Distilled Water | 78.0–80.0% | |
| Total | 100.0% | |

Prototype Shampoo Compositions Comprising Sodium Lauryl Sulfate and Heteroatom Containing Alkyl Aldonamide Compounds

| Ingredients | Wt | Function |
|---|---|---|
| Sodium Lauryl Sulfate | 15.0% | Cleansing Agent |
| Heteroatom Containing Alkyl Aldonamide | 3.0–5.0% | Foam Stabilizer/ Thickener |
| Sodium Chloride | 2.0% | Viscosity Cobuilder |
| Distilled Water | 78.0–80.0% | |
| Total | 100.0% | |

The above formulations were prepared by admixing the above ingredients in listed order and heating the mixture to about 80° C. with rapid stirring. The mixture was then cooled to about 40° C., placed in a clear jar and stored at room temperature for 6 months. The results are as follows:

The Clarity Enhancement of Prototype Shampoo Compositions Comprising Heteroatom Containing Alkyl Aldonamide Compounds and Sodium Lauryl

| Wt Thickener (Example 87) | Appearance (Time) |
|---|---|
| 0.0% No Thickener (Control) | Precipitate (2 weeks) |
| 4.0% $C_9$ D-Gluconamide (Comparative) | Precipitate (2 weeks) |
| 5.0% $C_9$ D-Gluconamide (Comparative) | Precipitate (2 weeks) |
| 3.0% $C_{10}$ D-Gluconamide (Comparative) | Precipitate (1 week) |
| 5.0% $C_{10}$ D-Gluconamide (Comparative) | Precipitate (5 days) |
| 3.0% $C_{12}$ D-Gluconamide (Comparative) | Precipitate (2 days) |
| 5.0% $C_{12}$ D-Gluconamide (Comparative) | Precipitate (1 hour) |
| 3.0% Coco D-Gluconamide (Comparative) | Precipitate (1 day) |
| 5.0% Coco D-Gluconamide (Comparative) | Precipitate (2 hours) |
| 3.0% $C_8/C_{10}$ Oxypropyl D-Gluconamide | Clear |
| 4.0% $C_8/C_{10}$ Oxypropyl D-Gluconamide | Clear |
| 5.0% $C_8/C_{10}$ Oxypropyl D-Gluconamide | Clear |
| 3.0% $C_{12}$ Oxypropyl D-Gluconamide | Clear |
| 5.0% $C_{12}$ Oxypropyl D-Gluconamide | Precipitate (5 months) |
| 3.0% Cocoaminopropyl D-Gluconamide | Clear |
| 5.0% Cocoaminopropyl D-Gluconamide | Clear |
| 3.0% $C_8/C_{10}$ Oxypropyl D-Lactobionamide | Clear |
| 5.0% $C_8/C_{10}$ Oxypropyl D-Lactobionamide | Clear |

For a clear shampoo formulation to be successful it must have good shelf life and should not become turbid or produce sedimentation upon standing. From the above table it can be seen that the shampoo compositions comprising alkyl aldonamides that lack heteroatoms do not stay in solution and precipitate out within an hour to about 2 weeks whereas those that contain heteroatoms stay in solution for 5 months or greater and provide clear shampoo formulations. This finding also suggests that the non-heteroatom containing alkyl aldonamide compounds of the invention are useful as pearlescent agents (opacifiers) which provide a soft, silvery and pearly luster to hare-care compositions, and as suspending agents which provide a means of suspending certain ingredients effectively, thereby assisting in the delivery of the desirable performance attributes associated with these ingredients.

Example 88

Viscosity Modification of Sodium Lauryl Sulfate with Heteroatom Containing Alkyl Aldonamide Compounds In order to demonstrate the improved ability of heteroatom containing alkyl aldonamide compounds to enhance viscosity, several prototype shampoo compositions were prepared and their viscosity measured using a Brookfield Digital Viscometer at 22° C. The prototype shampoo composition is as follows:

Prototype Shampoo Compositions Comprising Sodium Lauryl Sulfate and Heteroatom Containing Alkyl Aldonamide Compounds

| Ingredients | Wt | Function |
|---|---|---|
| Sodium Lauryl Sulfate | 15.0% | Cleansing Agent |
| Heteroatom Containing Alkyl Aldonamide | 1.0–5.0% | Foam Stabilizer/ Thickener |
| Sodium Chloride | 2.0% | Viscosity Cobuilder |
| Distilled Water | 78.0–82.0% | |
| Total | 100.0% | |

The above formulations were prepared by admixing the above ingredients in listed order and heating the mixture to about 80° C. with rapid stirring. The mixture was then cooled to about 40° C., placed in a clear jar and stored at room temperature for 6 months.

It is well known that the viscosity of a liquid composition comprising of anionic surfactant can be modified by the addition of inorganic salts, such as sodium chloride. However, in the absence of an organic modifier, high levels of salt may be necessary to achieve the required viscosity which may lead to problems of storage at cold temperature or even salting out certain ingredients. In practice, however, the viscosity of a liquid composition is modified by the simultaneous addition of thickener and small amounts of inorganic salt (viscosity cobuilder). The combined effect is greater than either one alone. The viscosity of the above prototype shampoo composition comprising various amounts of heteroatom containing alkyl aldonamide compound is as follows:

The Viscosity of Prototype Shampoo Compositions Comprising Sodium Lauryl Sulfate and Heteroatom Containing Alkyl Aldonamide Compounds

| Wt Thickener (Example 88) | Viscosity (Centipoise) | Increase |
|---|---|---|
| 1.0% $C_8/C_{10}$ Oxypropyl D-Gluconamide | 200 | 13× |
| 2.0% $C_8/C_{10}$ Oxypropyl D-Gluconamide | 400 | 27× |
| 3.0% $C_8/C_{10}$ Oxypropyl D-Gluconamide | 1200 | 80× |
| 4.0% $C_8/C_{10}$ Oxypropyl D-Gluconamide | 2220 | 148× |
| 5.0% $C_8/C_{10}$ Oxypropyl D-Gluconamide | 12900 | 860× |
| 3.0% $C_{12}$ Oxypropyl D-Gluconwwde | 1800 | 120× |
| 5.0% $C_{12}$ OxyPropyl D-Gluconamide | 20600 | 1373× |
| 3.0% $C_{12}$ Oxypropyl D-Lactobionainide | 340 | 23× |
| 5.0% $C_{12}$ Oxypropyl D-Lactobionamide | 1455 | 97× |
| 0.0% No Thickener (Control) | 15 | 0× |

From the above table it can be seen that the addition of a heteroatom containing alkyl aldonamide compound to a shampoo formulation increased the viscosity of that composition from about 13 to about 1373 times from its normal viscosity. This finding suggests that heteroatom containing alkyl aldonamide compounds of the invention are useful as effective viscosity modifiers or thickeners.

In order to further demonstrate the improved ability of heteroatom containing alkyl aldonamide compounds to enhance viscosity, the viscosity of several prototype shampoo compositions in Example 86 were measured using a Brookfield Digital Viscometer at 22° C. The results are as follows:

Viscosity Enhancement of Sodium/Ammonium Lauryl Sulfate with Heteroatom Containing Alkyl Aldonamide Compounds

| 4.0% Thickener | Viscosity (Centipoise) |
|---|---|
| $C_8/C_{10}$ Oxypropyl D-Gluconamide | 2395 |
| Lauramide DEA | 2376 |
| Cocoamide MEA | 1720 |
| Neodol 91-6 | 212 |
| No Thickener (Control) | 22 |

From the above table it can be seen that the addition of $C_8/C_{10}$ oxypropyl D-gluconamide to a shampoo formulation increased the viscosity of that composition 109 times (2395/22=109×) from its normal viscosity. Also closer comparision reveals that $C_8/C_{10}$ oxypropyl D-gluconamide enhances the viscosity of a shampoo composition more effectively than lauramide diethanolamine (DEA), cocoamide monoethanolamine (MEA) or Neodol 91-6 ($C_9$–$C_{11}$ alcohol ethoxylate with 6 moles of ethylene oxide). This finding suggests that heteroatom containing alkyl aldonamide compounds of the invention are useful as effective viscosity modifiers or thickeners.

While not wishing to be bound to theory, it is believed that common thickeners and foam stabilizers such as lauramide DEA and cocoamide MEA operate by being solubilized in the palisade layer of the ionic micelle. Here they act as "buffers" between repelling ionic head groups producing a closer-packed coherent surface film of foam that is more resilient and slow draining. The efficiency of an additive to stabfiize foam and enhance viscosity increases with the number of hydrogen bonding groups per molecule as well as the number of carbons in the alkyl chain. Additive hydrogen bonding groups are attacted to the ionic head groups of the surfactant by ion-dipole interactions whereas the hydrocarbon portions are attracted by Van der Waals forces. Therefore, the greater the intermolecular cohesive forces, the more effectively the additive is held in the palisade layer. Since long chained heteroatom containing alkyl aldonamide compounds contain multiple hydrogen bonding groups, they should be held tightly in the palisade layer and should not be squeezed out or forced into the interior of the micelle. If the hetroatom containing alkyl aldonamide compound is of proper size, as those described in this disclosure, a composition will exhibit enhanced stable foam and increased viscosity as shown in Examples 85–88.

Examples 89

Mildness Potential of Heteroatom Containing Alkyl aldonamide Compounds (Zein Solublization Assay)

The zein solubilization assay was developed to determine the biological effects of surfactants on the skin. The protein is normally in soluble in water, but can be brought into solution by interaction with surfactants. The extent of zein dissolved is related to the irritation potential (M. J. Schwinger, Kolloid-Z. Z. Poly., 233, 848, 1969). The greater the zein solubilization, the greater the irritation potential of that surfactant on the skin.

In order to demonstrate the improved ability of heteroatom containing alkyl aldonamtde to provide mildness benefits to the skin (scalp), mixtures of $C_8/C_{10}$ oxypropyl D-gluconamide ($C_8/C_{10}$ OPG) and sodium lauryl sulfate (SLS) by weight were tested and compared to pure sodium lauryl sulfate. Thus, a 1% solution of surfactant (30 mls) was added to 1.5 g of zein and stirred at room temperature for 1 hour. Residual zein was collected and dried to constant weight. Differences between starting and residual weights were used to calculate % zein solubilized. The results are as follows:

Mildness Potential of Heteroatom Containing Alkyl aldonamide Compounds (Zein Solublization Assay)

| Active Ratio ($C_8/C_{10}$ OPG:SLS) | % Zein Solubilized |
|---|---|
| 0:100 | 86 |
| 25:75 | 58 |
| 50:50 | 43 |
| 75:25 | 22 |
| 100:0 | 6 |
| No Surfactant (Control) | 5 |

As indicated by the above table, the addition of $C_8/C_{10}$ oxypropyl D-gluconamide to sodium lauryl sulfate results in less zein solubilization. This result suggests that these formulations (25:75 to 100:0) are more mild than sodium lauryl sulfate alone, and so the heteratom containing alkyl aldonamide compounds not only enhance viscosity and stabilize foam, but are also mild to the hair and scalp.

Examples 90–96

Physical Chemistry of Heteroatom Containing Alkyl Aldonamide Compounds

There are several unique characteristic properties that distinguish surface-active materials (surfactants) from other non-surface active materials. These include critical micelle concentration, surface tension reduction, efficiency in surface tension reduction, effectiveness in surface tension reduction, effectiveness of adsorption, area per molecule and miceliar shape or structure. The following examples will show that the heteroatom containing alkyl aldonamide compounds of the invention are surface-active and are therefore considered to be a new class of sugar based surfactant.

Example 90

Critical Micelle Concentration

The critical micelle concentration (CMC) is defined as the concentration at which a surfactant forms micelles in aqueous solution. Micellization is the preferred interfacial phenomena, since certain surfactant benefits such as detergency (the solubilization of soils), foaming, wetting or emulsification depend on the formation of these aggregates in solution. Materials that do not form micelles do not provide any detergency, foaming, wetting or emulsification.

The CMC value of $C_8/C_{10}$ oxypropyl D-gluconamide was determined by plotting surface tension as a function of log(concentration) and extrapolating linear points to obtain an intersection point. The concentration at this point was taken as the CMC. The technique used was the Wilhelmy plate method and the instrument used was a Lauda Auto-Tensiometer. While wishing not to be bound to theory, it is believed that surfactants with low CMC values form micelles more readily at lower concentrations than those with high CMC values.

The critical micelle concentration (CMC) value of $C_8/C_{10}$ oxypropyl D-gluconamide (molecular weight=375.02 g/mole, 65.9% $C_8$, 34.1% $C_{10}$) was determined and is set forth below:
The Critical Micelle Concentration of $C_8/C_{10}$ Oxypropyl D-Gluconamide

| Entry | Surfactant | ANC* | CMC | Temperature (°C.) |
| --- | --- | --- | --- | --- |
| 1 | $C_8/C_{10}$ Oxypropyl D-Gluconamide | 11.7 | 0.095 mM (0.0356%) | 60 |
| 2 | Dodecyl D-Gluconamide (Comparative) | 12.0 | None (Insoluble) | 60 |

*ANC = Average Number of Carbon Atoms in the Alkyl Chain

A necessary and sufficient condition for CMC formation and surface tension reduction is the presence of both hydrophilic and hydrophobic functional groups. The hydrophilic portion provides strong interaction between the surfactant at the interface and with the surrounding water phase. The hydrophobic portion provides spontaneous adsorption of the surfactant at the interface and strong interaction with the adjacent air phase. If any of these functions are not performed, then CMC formation and surface tension reduction will not occur. For significant surface activity, a properly balanced hydrophilic and hydrophobic character is essential. From the above table it can be seen that $C_8/C_{10}$ oxypropyl D-gluconamide is properly balanced and forms micelles at a surprising low critical micelle concentration whereas dodecyl D-gluconamide is insoluble in water and can not form micelles. This finding suggests that the heteroatom containing alkyl aldonamides of the invention to be surface-active and so these compounds are expected to deliver favorable surfactant benefits. Also, since dodecyl D-gluconamide is insoluble in water, the additional physical properties in Examples 91–96 of this compound can not be determined.

Example 91

Surface Tension Reduction

An important characteristic feature that surfactants have is the tendency for them to absorb at the water/air interface in an oriented manner, thereby altering the interfacial free energy of that surface. The surface free energy per unit area or surface tension ($\gamma$), is a measure of this work and may be considered as the minimum amount of work required to bring sufficient surfactant molecules to the surface.

The surface tension ($\gamma$) value of $C_8/C_{10}$ oxypropyl D-gluconamide was determined and is set forth below:
Surface Tension of $C_8/C_{10}$ Oxypropyl D-Glueonamide at the Water/Air Interface

| Entry | Surfactant | $\gamma$ | Temperature (°C.) |
| --- | --- | --- | --- |
| 1 | $C_8/C_{10}$ Oxypropyl D-Gluconamide | 29.2 dyn/cm | 60 |
| 2 | Water | 60.2 dyn/cm | 60 |

From the above table it can be seen that $C_8/C_{10}$ oxypropyl D-gluconamide absorbs strongly at the water/air interface resulting in a significant reduction in water surface tension. This finding suggests that the heteroatom containing alkyl aldonamides of the invention to be surfaceactive and so these compounds are expected to deliver favorable surfactant benefits.

Examples 92–93

Performance of Heteroatom Containing Alkyl Aldonamide Compounds in Reducing Surface Tension For the purpose of comparing the performance of heteroatom containing alkyl aldonamide compounds in reducing surface tension to other surfactants, it is necessary to distinguish between the efficiency and effectiveness.

Efficiency of a surfactant in reducing surface tension is defined as the bulk phase surfactant concentration required to reduce the surface tension of water by some given amount.

Effectiveness of a surfactant in reducing surface tension is defined as the maximum reduction in surface tension that can be obtained regardless of the bulk phase surfactant concentration.

Example 92

Efficiency in Surface Tension Reduction

Since surface tension reduction depends on the replacement of water molecules at the interface by surfactant molecules, the efficiency of a surfactant in reducing interfacial tension should reflect the concentration of surfactant at the interface relative to that in bulk liquid phase. A suitable measure of efficiency with which a surfactant performs this function can be described as $pC_{20}$. This is defined as the negative logarithm of the bulk phase surfactant concentration necessary to reduce the surface tension of water by 20 dyn/cm and is given as:

$$pC_{20} = -\log [C_{(-\Delta\gamma=20)}] = -\log [C_{20}]$$

wherein:

$C_{(-\Delta\gamma=20)}=C_{20}$ is the bulk phase surfactant concentration necessary to reduce the surface tension of water by 20 dyn/cm.

In general, $pC_{20}$ values are usually close to the minimum concentration needed to saturate the interface with surfactant molecules. While not wishing to be bound by theory, it is believed that surfactants that have high $pC_{20}$ values tend to absorb more efficiently at the interface thereby reducing the surface tension more efficiently than those that have low $pC_{20}$ values.

The efficiency of various surfactants in reducing surface tension ($pC_{20}$) were determined and are set forth below:
The Efficiency of Various Nonionic Surfactants in Reducing the Surface Tension of Water

| Entry | Surfactant | ANC* | $pC_{20}$ | Temperature (°C) |
|---|---|---|---|---|
| 1 | $C_8/C_{10}$ Oxypropyl D-Gluconamide | 11.7 | 4.78 | 60 |
| 2 | Dodecytri(oxyethylene) Ether[1] $C_{12}H_{25}O(CH_2CH_2O)_3H$ (Comparative) | 12 | 5.34 | 25 |
| 3 | Dodecyltetra(oxyethylene) Ether[1] $C_{12}H_{25}O(CH_2CH_2O)_4H$ (Comparative) | 12 | 5.34 | 25 |
| 4 | Dodecylpenta(oxyethylene) Ether[1] $C_{12}H_{25}O(CH_2CH_2O)_5H$ (Comparative) | 12 | 5.37 | 25 |
| 5 | Dodecylhepta(oxyethylene) Ether[1] $C_{12}H_{25}O(CH_2CH_2O)_7H$ (Comparative) | 12 | 5.26 | 25 |
|   |   |   | 5.28 | 40 |
|   |   |   | 5.41 | 60[2] |
| 6 | Dodecylocta(oxyethylene) Ether[1] $C_{12}H_{25}O(CH_2CH_2O)_8H$ (Comparative) | 12 | 5.20 | 25 |
|   |   |   | 5.22 | 40 |
|   |   |   | 5.39 | 60[2] |

[1]Rosen, M. J., in Surfactants and Interfacial Phenomena 2 ed., Wiley-Interscience Publication, 1989, pg 78; and Rosen, M. J., Cohen A. W., Dahanayake M. and Hua X. Y., J. Phys. Chem. 86, 541, 1981.
[2]This value was estimated by plotting temperature as function of $pC_{20}$ and extrapolating a linear line at 60° C.
*ANC = Average Number of Carbon Atoms in the Alkyl Chain From the above table it can be seen that $C_8/C_{10}$ oxypropyl D-gluconamide has a high $pC_{20}$ value and is expected to efficiently reduce the surface tension of water. This finding suggests that the heteroatom containing alkyl aldonamides of the invention to be surface-active and so these compounds are expected to deliver favorable surfactant benefits.

Example 93

Effectiveness in Reducing Surface Tension

As mentioned before, surface tension reduction depends on the replacement of water molecules at the interface by surfactant molecules, therefore the effectiveness of a surfactant in reducing interfacial surface tension should reflect the saturated concentration of surfactant at the interface relative to that in bulk liquid phase. During this process the surface tension of water steadily decreases as bulk phase surfactant concentration increases. This will continue until the concentration reaches the critical micelle concentration (CMC), above which the surface tension remains nearly unchanged and the interface is saturated with surfactant. The surface tension at the CMC is therefore very close to the minimum interfacial tension or maximum surface pressure that the system can achieve. The surface pressure at this point, $\Pi_{cmc}$, is a suitable measure of the effectiveness of a surfactant in reducing surface tension and is given as:

$$\Pi_{cmc} = 20 + 2.3nRT(\Gamma_{max}) \log [CMC/C_{20}]$$

wherein:

n=1 which represents the number of ions whose surface concentration changes with the change in liquid phase surfactant concentration.

R=8.314×10$^7$ ergs/mol K (Gas Constant)

T=333.15K $\Gamma_{max}=-1/2.303RT(\partial\gamma/\partial\log [Conc])_T=3.85\times10^{-10}$ mole/cm$^2$ $CMC/C_{20}=$ is the ratio of the critical micelle concentration to the bulk phase surfactant concentration necessary to reduce the surface tension of water by 20 dyn/cm.

While not wishing to be bound by theory, it is believed that surfactants that have higher $\Pi_{cmc}$ values tend to absorb effectively at the interface thereby reducing the surface tension of water more effectively than those with lower $\Pi_{cmc}$ values.

The effectiveness of various surfactants in reducing surface tension ($\Pi_{cmc}$) were determined and are set forth below:
Effectiveness of Various Nonionic Surfactants in Reducing the Surface Tension of Water

| Entry | Surfactant | $CMC/C_{20}$ | $\Pi_{cmc}$ | Temperature (°C) |
|---|---|---|---|---|
| 1 | $C_8/C_{10}$ Oxypropyl D-Gluconamide | 5.7 | 38.5 dyn/cm | 60 |
| 2 | Dodecyltri(oxyethylene) Ether[1] $C_{12}H_{25}O(CH_2CH_2O)_3H$ (Comparative) | 11.4 | 44.1 dyn/cm | 25 |
|   |   |   | 43.1 dyn/cm | 40 |
|   |   |   | 41.4 dyn/cm | 60[2] |
| 3 | Dodecyltetra(oxyethylene) Ether[1] $C_{12}H_{25}O(CH_2CH_2O)_4H$ (Comparative) | 13.7 | 43.4 dyn/cm | 25 |
|   |   | 11.8 | 42.0 dyn/cm | 40 |
|   |   |   | 40.7 dyn/cm | 60[2] |
| 4 | Dodecylpenta(oxyethylene) Ether[1] $C_{12}H_{25}O(CH_2CH_2O)_5H$ (Comparative) | 15.0 | 41.5 dyn/cm | 25 |
|   |   |   | 41.2 dyn/cm | 40 |
|   |   |   | 40.7 dyn/cm | 60[2] |
| 5 | Dodecylhepta(oxyethylene) Ether[1] $C_{12}H_{25}O(CH_2CH_2O)_7H$ (Comparative) | 14.9 | 38.3 dyn/cm | 25 |
|   |   | 13.9 | 38.5 dyn/cm | 40 |
|   |   |   | 36.8 dyn/cm | 60[2] |
| 6 | Dodecylocta(oxyethylene) Ether[1] $C_{12}H_{25}O(CH_2CH_2O)_8H$ (Comparative) | 17.3 | 37.2 dyn/cm | 25 |
|   |   | 15.4 | 37.3 dyn/cm | 40 |
|   |   |   | 36.3 dyn/cm | 60[2] |

[1]Rosen, M. J., in Surfactants and Interfacial Phenomena 2 ed., Wiley-Interscience Publication, 1989, pgs 146 and 224; and Rosen, M. J., Cohen A. W., Dahanayake M. and Hua X. Y., J. Phys. Chem. 86, 541, 1981.
[2]This value was estimated by plotting temperature as function of surface pressure ($\Pi_{cmc}$) and extrapolating a linear line at 60° C.

From the above table it can be seen that $C_8/C_{10}$ oxypropyl D-gluconamide has a high $\Pi_{cmc}$ value and is expected to effectively reduce the surface tension of water. For $C_8/C_{10}$ oxypropyl D-gluconamide, the surface pressure ($\Pi_{cmc}$) was found to be similar to dodecytetra(oxyethylene) ether and dodecylpenta(oxyethylene) ether. This finding suggests that the heteroatom containing alkyl aldonamtde compounds of the invention to be surface-active and so these compounds are expected to deliver favorable surfactant benefits.

Example 94

Effectiveness of Adsorption at the Interface

The surface excess concentration at surface saturation ($\Gamma_{max}$) is defined as a measure of the effectiveness of surfactant adsorption at the water/air interface and represents the maximum value to which adsorption can be obtained. Effectiveness of adsorption is related to the interfacial area occupied by the surfactant molecule. The smaller the effective cross-sectional area of a surfactant at the interface, the greater its effectiveness of adsorption. The effectiveness of adsorption is an important factor in determining surfactant properties such as detergency, foaming, wetting or emulsification. While not wishing to be bound by theory, it is believed that surfactants that absorb effectively at the interface tend have tightly packed coherent interfacial films and often provide better surfactant benefits than those with loosely packed noncoherent films. The effectiveness of adsorption of $C_8/C_{10}$ oxypropyl D-gluconamide was determined using the Gibbs equation given as:

$$\Gamma_{max} = -1/2.303RT(\partial\gamma/\partial\log[Conc])_T$$

wherein:

$(\partial\gamma/\partial\log[Conc])_T = -24.574971$ ergs/cm² (which is equivalent to the slope of a plot of $\gamma$ versus log [Conc])

$R = 8.314 \times 10^7$ ergs/mol K (Gas Constant)

$T = 333.15K$

The surface excess concentration at surface saturation ($\Gamma_{max}$) of various suffactants were determined and are set forth below:

Effectiveness of Adsorption of Various Nonionic Surfactants at the Water/Air Interface per molecule values. From the surface excess concentration at surface saturation ($\Gamma_{max}$), the area per molecule ($a_m$) of $C_8/C_{10}$ oxypropyl D-gluconamide was determined and is given by:

$$a_m = 1 \times 10^{16}/N_{av}\Gamma_{max}$$

wherein:

$\Gamma_{max} = -1/2.303RT(\partial\gamma/\partial\log[Conc])_T$ $N_{av} = 6.0221 \times 10^{23}$ per gram mole (Avogadro's Number)

$T = 333.15K$

The area per molecule ($a_m$) of several surfactants were determined and are set forth below:

Area Per Molecule of Various Nonionic Surfactants at the Water/Air Interface

| Entry | Surfactant | $a_m$ | Temperature (°C.) |
|---|---|---|---|
| 1 | $C_8/C_{10}$ Oxypropyl D-Gluconamide | 43.1 Å² | 60 |
| 2 | Dodecyltri(oxyethylene) Ether[1] | 41.7 Å² | 25 |
|   | $C_{12}H_{25}O(CH_2CH_2O)_3H$ | 42.5 Å² | 40 |
|   | (Comparative) | 45.4 Å² | 60[2] |
| 3 | Dodecyltetra(oxyethylene) Ether[1] | 45.7 Å² | 25 |
|   | $C_{12}H_{25}O(CH_2CH_2O)_4H$ | 48.7 Å² | 40 |

| Entry | Surfactant | $\Gamma_{max}$ | Temperature (°C.) |
|---|---|---|---|
| 1 | $C_8/C_{10}$ Oxypropyl D-Gluconamide | $3.85 \times 10^{-10}$ mole/cm² | 60 |
| 2 | Dodecyltri(oxyethylene) Ether[1] | $3.98 \times 10^{-10}$ mole/cm² | 25 |
|   | $C_{12}H_{25}O(CH_2CH_2O)_3H$ | $3.90 \times 10^{-10}$ mole/cm² | 40 |
|   | (Comparative) | $3.83 \times 10^{-10}$ mole/cm² | 60[2] |
| 3 | Dodecyltetra(oxyethylene) Ether[1] | $3.63 \times 10^{-10}$ mole/cm² | 25 |
|   | $C_{12}H_{25}O(CH_2CH_2O)_4H$ | $3.41 \times 10^{-10}$ mole/cm² | 40 |
|   | (Comparative) | $3.01 \times 10^{-10}$ mole/cm² | 60[2] |
| 4 | Dodecylpenta(oxyethylene) Ether[1] | $3.31 \times 10^{-10}$ mole/cm² | 25 |
|   | $C_{12}H_{25}O(CH_2CH_2O)_5H$ | $3.28 \times 10^{-10}$ mole/cm² | 40 |
|   | (Comparative) | $3.16 \times 10^{-10}$ mole/cm² | 60[2] |
| 5 | Dodecylhepta(oxyethylene) Ether[1] | $2.90 \times 10^{-10}$ mole/cm² | 25 |
|   | $C_{12}H_{25}O(CH_2CH_2O)_7H$ | $2.77 \times 10^{-10}$ mole/cm² | 40 |
|   | (Comparative) | $2.71 \times 10^{-10}$ mole/cm² | 60[2] |
| 6 | Dodecylocta(oxyethylene) Ether[1] | $2.52 \times 10^{-10}$ mole/cm² | 25 |
|   | $C_{12}H_{25}O(CH_2CH_2O)_8H$ | $2.46 \times 10^{-10}$ mole/cm² | 40 |
|   | (Comparative) | $2.40 \times 10^{-10}$ mole/cm² | 60[2] |

[1] Rosen, M. J., in Surfactants and Interfacial Phenomena 2 ed., Wiley-Interscience Publication, 1989, pg 78; and Rosen, M. J., Cohen A. W., Dahanayake M. and Hua X. Y., J. Phys. Chem. 86, 541, 1981.
[2] This value was estimated by plotting temperature as function of surface excess concentration at surface saturation ($\Gamma_{max}$) and extrapolating a linear line at 60° C.

From the above table it can be seen that $C_8/C_{10}$ oxypropyl D-gluconamide has a small cross sectional area resulting in a tightly packed coherent interfacial film and strong effective interfacial absorption. The surface excess concentration at surface saturation ($\Gamma_{max}$) of this compound was found to be similar to dodecyltri(oxyethylene) ether (a common nonionic surfactant). This finding suggests that the heteroatom containing alkyl aldonamide compounds of the invention to be surface-active and so these compounds are expected to deliver favorable surfactant benefits.

Example 95

Area Per Molecule at the Interface

The area per molecule of a surfactant at the water/air interface provides information on the degree of packing and the orientation of the adsorbed surfactant molecule. While not wishing to be bound by theory, it is believed that surfactants that have small area per molecule values tend to pack more closely at the interface than those with large area -continued

| Entry | Surfactant | $a_m$ | Temperature (°C.) |
|---|---|---|---|
|   | (Comparative) | 53.3 Å² | 60[2] |
| 4 | Dodecylpenta(oxyethylene) Ether[1] | 50.1 Å² | 25 |
|   | $C_{12}H_{25}O(CH_2CH_2O)_5H$ | 50.6 Å² | 40 |
|   | (Comparative) | 52.3 Å² | 60[2] |
| 5 | Dodecylhepta(oxyethylene) Ether[1] | 57.3 Å² | 25 |
|   | $C_{12}H_{25}O(CH_2CH_2O)_7H$ | 59.9 Å² | 40 |
|   | (Comparative) | 61.0 Å² | 60[2] |
| 6 | Dodecylocta(oxyethylene) Ether[1] | 66.0 Å² | 25 |
|   | $C_{12}H_{25}O(CH_2CH_2O)_8H$ | 67.4 Å² | 40 |
|   | (Comparative) | 69.0 Å² | 60[2] |

[1] Rosen, M. J., in Surfactants and Interfacial Phenomena 2 ed., Wiley-Interscience Publication, 1989, pg 78; and Rosen, M. J., Cohen A. W., Dahanayake M. and Hua X. Y., J. Phys. Chem. 86, 541, 1981.
[2] This value was estimated by plotting temperature as function of area per molecule ($a_m$) and extrapolating a linear line at 60° C.

From the above table it can be seen that $C_8/C_{10}$ oxypropyl D-gluconamide has a favorably small area per molecule value and is expected to pack tightly at the interface. The area per molecule ($a_m$) of this compound was found to be similar to dodecyltri(oxyethylene) ether. This finding suggests that the heteroatom compounds of the invention to be surface-active and so these compounds are expected to deliver favorable surfactant benefits.

Example 96

Micellar Shape and Structure

The shape or type of micelle produced by a surfactant in aqueous solution is an important criteria for delivering certain surfactant benefits such as viscosity, detergency, foaming, wetting or emulsification. At present there appears to be four major types of micelles a surfactant can form in aqueous solution;

(1) spherical micelles (2) cylindrical rod-like micelles (3) lamellar disk-like micelles (4) vesicles or reversed micelles In aqueous media, surfactant molecules may be oriented in all these possible structures with their polar hydrophilic head groups pointed towards the aqueous phase and their non-polar hydrophobic alkyl chain groups pointed away from it. In general, surfactants with large bulky or loosely packed hydrophilic groups and long, thin hydrophobic groups tend to form predominately spherical micelles whereas those with small or tightly packed hydrophilic groups and bulky hydrophobic groups tend to form predominately cylindrical or lamellar micelles. Changes in temperature, concentration and functional groups in the surfactant may all cause a change in size or shape of a micelle.

A theory of micellar structure, based upon the geometry of various micelle shapes and the space occupied by the surfactant has been disclosed by J. N. Israelachvili, D. J. Mitchell and B. W. Ninham in the J. Chem. Soc. Faraday Trans. 2, 1525, 72, (1976) which is given as the packing parameter (p).

$$p = V_T / l_c(a_m)$$

wherein;

$V_T = V_{(CH3)} + (n_c-1)V_{(CH2)}$ and represents the volume occupied by the hydrophobic groups in the micellar core at a given temperature.

$l_c = 1.50 + 1.26\ n_c$ Å and represents the length of the hydrophobic group in the core.

$a_m$ = area per molecule or the cross-sectional area occupied by the hydrophilic group at the interface.

$V_{(CH3)} = 54.6 + 0.124\ (T - 298°\ K.)$Å$^3$ $V_{(CH2)} = 26.9 + 0.0146\ (T - 298°\ K.)$Å$^3$ $T = 333.15°$ K.

$n_c$ = total number of carbons in the alkyl chain.

Values obtained from the packing parameter (p) represent the following structures:

| Values of (p) | Structure of Micelle in Aqueous Media |
| --- | --- |
| 0.00 to 0.33 | Spherical |
| 0.33 to 0.50 | Cylindrical |
| 0.50 to 1.00 | Lamellar |
| >1.00 | Reversed |

The packing parameter (p) of $C_8/C_{10}$ oxypropyl D-Gluconamide was determined as follows:

The Packing Parameter of $C_8/C_{10}$ Oxypropyl D-Gluconamide

| Entry | Surfactant | $n_a^1$ | $V_T$(Å$^3$) | $l_c$(Å)$^1$ | $a_m$(Å$^2$) | p |
| --- | --- | --- | --- | --- | --- | --- |
| 1 | $C_8/C_{10}$ Oxypropyl D-Gluconamide | 12.7 | 379.7 | 17.5 | 43.1 | 0.503 |

[1]This value represents the number atoms in the alkyl chain and assumes that one oxygen atom is equivalent to one methylene group.

Form the above table it can be seen that the packing parameter (p) for $C_8/C_{10}$ oxypropyl D-gluconamide was found to be 0.503 which means that this compound is predicted to form cylindrical to lamellar micelles. This finding suggests that the heteroatom containing alkyl aldonamide compounds of the invention to be surface-active and so these compounds are expected to deliver favorable surfactant benefits.

Examples 97–135

Compositions Comprising Heteroatom Containing Alkyl Aldonamide Compounds

The following examples represent hair care compositions comprising heteroatom containing alkyl aldonamtde compounds according to the instant invention. Unless otherwise indicated, all percentages herein are by weight.

Examples 97–103

Prototype Shampoo Compositions Comprising Heteroatom Containing Alkyl Aldonamide Compounds

| Example Ingredients (By Weight) | 97 % | 98 % | 99 % | 100 % | 101 % | 102 % | 103 % |
| --- | --- | --- | --- | --- | --- | --- | --- |
| 1. Sodium Lauryl Sulfate (28%) | — | — | — | — | 35.0 | — | 8.0 |
| 2. Ammonium Lauryl Sulfate (28%) | — | — | 40.0 | — | — | — | — |
| 3. Triethanolamine Lauryl Sulfate (40%) | — | — | — | — | — | — | 22.0 |
| 4. Sodium Laureth-1 Sulfate (25%) | 30.0 | — | — | — | — | — | — |
| 5. Sodium Laureth-2 Sulfate (25%) | — | 30.0 | — | — | — | 15.0 | — |
| 6. Sodium Laureth-2 Sulfate (50%) | — | — | — | 19.0 | — | — | — |
| 7. Sodium Lauryl Sarcosinate (30%) | 10.0 | — | — | — | — | — | — |
| 8. Disodium PEG-3 Sulfosuccinate (45%) | — | — | — | — | — | 12.0 | — |
| 9. Lauryl Betaine (30%) | — | — | — | — | — | 10.0 | — |

-continued

| Example<br>Ingredients (By Weight) | 97 % | 98 % | 99 % | 100 % | 101 % | 102 % | 103 % |
|---|---|---|---|---|---|---|---|
| 10. Cocoamidopropyl Betaine (35%) | — | 11.0 | 5.0 | 8.0 | — | — | — |
| 11. Cocoamidopropylhydroxy Sultaine (35%) | — | — | — | — | — | — | 6.0 |
| 12. C8–C18 Alkylpolyglycoside (50%) | — | — | — | — | 8.0 | — | — |
| 13. PEG-12 Distearate | — | — | — | — | — | — | 2.0 |
| 14. Nonoxynol-9 | — | — | — | — | — | 0.5 | — |
| 15. PEG-120 Methyl Glucose Dioleate | — | — | — | — | — | — | 2.0 |
| 16. C8/C10 Oxypropyl D-Gluconamide | 1.0 | — | — | — | 1.0 | — | — |
| 17. C8/C10 Oxypropyl D-Lactobionamide (50%) | 5.0 | — | 4.0 | 6.0 | 6.0 | — | 4.0 |
| 18. C12 Oxypropyl D-Lactobionamide (50%) | — | 8.0 | — | — | — | 6.0 | — |
| 19. Cocoaminopropyl D-Gluconamide (50%) | 0.1 | — | — | — | — | — | — |
| 20. Oleylaminopropyl D-Lactobionamide (50%) | 0.1 | — | — | 0.5 | — | — | — |
| 21. Quaternium-15 | — | — | 0.5 | — | — | — | — |
| 22. Quaternium-22 | 1.0 | — | — | — | — | — | 0.2 |
| 23. Polyquaternium-10 | — | — | — | 0.2 | — | — | — |
| 24. Quaternium-20 | — | — | — | — | 2.0 | — | — |
| 25. Aloe Vera Gel | — | — | 0.5 | — | — | — | — |
| 26. Glycerin | — | 2.0 | — | — | — | 2.0 | — |
| 27. Acetamide | — | — | — | 2.0 | — | — | — |
| 28. Panthenol (Provitamin B) | — | — | 0.1 | 0.5 | — | — | — |
| 29. Keratin Amino Acids | — | — | — | 1.0 | — | — | — |
| 30. Hydrolyzed Animal Protein | — | 1.0 | 0.4 | — | — | — | — |
| 31. Honey | — | — | 0.2 | — | — | — | — |
| 32. Fennel Extract | — | — | — | 0.6 | — | — | — |
| 33. Hops Extract | — | — | — | 0.5 | — | — | — |
| 34. Balm Mint Extract | — | — | — | 0.4 | — | — | — |
| 35. Yarrow Extract | — | — | — | 0.3 | — | — | — |
| 36. Matricaria Extract | — | — | — | 0.2 | — | — | — |
| 37. PEG-10 Sorbitan Laurate | — | — | 0.2 | — | — | — | — |
| 38. Wheat Germ Oil | — | — | 0.1 | — | — | — | — |
| 39. Benzophenone-4 | 0.3 | — | — | — | — | — | — |
| 40. Benzyl Alcohol | — | 0.5 | — | — | — | — | — |
| 41. C12–C15 Alcohol Benzoate | — | — | — | 0.5 | — | — | — |
| 42. Propylene Glycol | 0.5 | — | — | — | — | — | — |
| 43. Methylchloroisothiazoline | — | — | — | — | — | 0.05 | — |
| 44. Methylisothiazoline | — | — | — | — | — | 0.05 | — |
| 45. DMDM Hydantoin | — | 0.4 | — | — | 0.4 | — | 0.3 |
| 46. Imidazolidinyl Urea | — | — | — | 0.2 | — | — | — |
| 47. Diazolidinyl Urea | 0.2 | — | — | — | — | — | — |
| 48. Methyl Paraben | 0.2 | — | 0.2 | 0.2 | — | — | — |
| 49. Propyl Paraben | 0.1 | — | 0.1 | 0.1 | — | — | — |
| 50. Disodium EDTA | 0.2 | — | — | — | — | — | 0.1 |
| 51. Tetrasodium EDTA | — | 0.1 | — | 0.1 | — | — | — |
| 52. Sodium Chloride (50%) Adjust Viscosity | q.s. | q.s | — | q.s. | q.s. | q.s. | q.s. |
| 53. Ammonium Chloride (35%) Adjust Viscosity | — | — | q.s. | — | — | — | — |
| 54. Citric Acid (35%) pH to 5–7 | q.s | — | q.s. | q.s. | q.s. | q.s. | q.s |
| 55. Lactic Acid (35%) pH to 5–7 | — | q.s. | — | — | — | — | — |
| 56. Dye (0.2%–1%) | q.s. | q.s. | q.s. | q.s. | q.s | — | q.s. |
| 57. Fragrance | q.s. | q.s. | q.s. | q.s. | q.s. | q.s | q.s. |
| 58. Water | 51.7 | 46.8 | 48.8 | 59.8 | 47.6 | 52.4 | 57.5 |

Quaternium-15 (1-{3-Chloroallyl}-3,5,7-Triaza-1-Azoniaadamantane Chlorode)
Quaternium-22 (Gluconamidopropyldimethyl 2-Hydroxyethylammonium Chloride)
Polyquaternium-10 (Polymer of Hydroxyethyl Cellulose Reacted with Epichlorohydrin/Triethylamine)
Quaternium-20 (Polyoxypropylene-25 Methyldiethylammonium Chloride)

Example 97

A Clear Shampoo Composition For Normal Hair with Sunscreen

Container A is charged with 58, 50, 4, 7, 17, 19, 20 and 16 which is heated to 70° C. with moderate stirring. When clear, add 22 and 39. Mix thoroughly. Cool the mixture to 40° C. and add 42, 47, 48 and 49. Mix thoroughly. Cool the mixture to room temperature and add 57, 56, 52 and 54. Mix thoroughly, heat if necessary and discharge when homogeneous.

Example 98

A Clear Shampoo Composition For Frequent Use with Moisturizer and Protein

Container A is charged with 30 and about 20% of 58. Mix thoroughly. Container B is charged with 58, 26, 51, 5, 10, 18 and 40 which is heated to 45° C. with moderate stirring. Slowly add A to B while stirring and then add 45, 57, 56, 52 and 55. Mix thoroughly, cool down the mixture and discharge when homogeneous.

Example 99

A Clear Shampoo Composition For Dry/Damaged Hair with Aloe, Protein, Honey, Wheat Germ Oil and Vitamins Container A is charged with 58 and 2. Mix thoroughly and add 28, 25, 30, 31, 48 and 49. Mix thoroughly until clear and uniform. Add 37 and 38. Mix thoroughly. Add 17, 10, 21, 57, 56, 53 and 54. Mix thoroughly, heat if necessary and discharge when homogeneous.

Example 100

A Clear Shampoo Composition For Dry/Damaged Hair with Moisturizer, Amino Acids, Protein, Vitamins and Extracts Container A is charged with 58 and 23. Disperse 23 with rapid stirring. Add 51 and heat to 50° C. Add 6. Mix thoroughly until clear and uniform. Add 10 and 20. Mix thoroughly until clear and uniform. Add 17. Mix thoroughly until clear and uniform. Add 27, 28, 29 and 41. Mix thoroughly. Add 48, 49 and 46. Mix thoroughly. Add 32, 33, 34, 35, 36, 57, 56, 52 and 54. Mix thoroughly, heat if necessary and discharge when homogeneous.

Example 101

A Clear Shampoo Composition For Oily Hair

Container A is charged with 58 and 24 which is heated to 60° C. Mix thoroughly until clear and uniform. Add 1, 12, 16 and 17. Mix thoroughly until clear and uniform. Add 57, 56, 52 and 54. Mix thoroughly, cool down the mixture and discharge when homogeneous.

Example 102

A Clear Baby Shampoo Composition with Moisturizer (No Dye)

Container A is charged with 58, 5, 8, 9, 14, 18 and 26 which is heated to 60° C. Mix thoroughly untfi clear and uniform. Add 43, 44, 57, 52 and 54. Mix thoroughly, cool down the mixture and discharge when homogeneous.

Example 103

A Clear Baby Shampoo Composition

Container A is charged with 58, 50, 1, 3, 11 and 13 which is heated to 60° C. Mix thoroughly until clear and uniform. Add 22, 15 and 17. Mix thoroughly until clear and uniform. Add 57, 56, 52 and 54. Mix thoroughly, cool down the mixture and discharge when homogeneous.

Examples 104–110

Prototype Conditioning Shampoo Compositions Comprising Heteroatom Containing Alkyl Aldonamide Compounds

| Example<br>Ingredients (By Weight) | 104 % | 105 % | 106 % | 107 % | 108 % | 109 % | 110 % |
|---|---|---|---|---|---|---|---|
| 1. Sodium C12–C15 Sulfate (25%) | — | — | — | — | 30.0 | — | — |
| 2. Ammonium Lauryl Sulfate (28%) | 30.0 | — | — | 33.0 | — | — | 14.0 |
| 3. Triethanolamine Lauryl Sulfate (40%) | — | 35.0 | — | — | — | — | — |
| 4. Sodium Laureth-1 Sulfate (25%) | — | 20.0 | — | — | — | — | — |
| 5. Sodium Laureth-2 Sulfate (26%) | — | — | — | — | — | — | 17.0 |
| 6. Sodium Laureth-2 Sulfate (50%) | — | — | — | — | 12.0 | 20.0 | — |
| 7. Sodium Laureth-3 Sulafte (50%) | — | — | 20.0 | — | — | — | — |
| 8. Ammonium Laureth-1 Sulfate (25%) | 30.0 | — | — | — | — | — | — |
| 9. Sodium Trideceth-7-Carboxylate (70%) | — | — | — | 10.0 | — | — | — |
| 10. Cocoamidopropyl Betaine (35%) | — | — | 5.0 | — | — | 6.5 | — |
| 11. Cocoampocarboxyglycinate (38%) | — | — | — | — | — | — | 13.0 |
| 12. PPG-5 Ceteth-10 Phosphate | — | — | 3.0 | — | — | — | — |
| 13. C8/C10 Oxypropyl D-Gluconamide | — | — | — | 1.0 | 2.0 | — | — |
| 14. C8/C10 Oxypropyl D-Lactobionamide (50%) | 4.0 | — | 10.0 | 4.0 | 5.0 | 10.0 | — |
| 15. C12 Oxypropyl D-Lactobionamide (50%) | — | 11.0 | — | — | — | — | — |
| 16. C12–C15 Oxypropyl D-Lactobionamide (50%) | — | — | — | — | — | — | 7.0 |
| 17. Sodium Pyrrolidone Carboxylic Acid | — | — | — | — | 0.5 | — | — |
| 18. Acetamide MEA | — | 1.0 | — | — | — | 1.0 | — |
| 19. Lactamide MEA | — | 1.0 | — | — | — | — | — |
| 20. Sodium Stearoyl Lactylate | — | — | — | — | 3.0 | — | — |
| 21. PEG-60 Corn Glycerides | — | — | 1.0 | — | — | — | — |
| 22. Ethylene Glycol Monstearate | 2.0 | — | — | — | — | — | — |
| 23. Ethylene Glycol Distearate | — | 2.5 | — | — | 3.5 | 1.0 | — |
| 24. Xanthan Gum | 0.2 | — | — | — | — | — | — |
| 25. Ammonium Xylene Sulfonate (40%) | 3.0 | — | — | — | — | — | — |
| 25b. Sodium Xylene Sulfonate (40%) | — | 3.0 | — | — | — | — | — |
| 26. Dimethicone | 1.0 | 0.6 | — | — | — | — | — |
| 27. Quaternium-14 | 1.0 | — | — | — | — | — | — |
| 28. Quaternium-22 | — | 2.0 | — | — | 0.5 | — | — |
| 29. Quaterium-19 | — | — | — | 1.0 | — | — | 1.2 |
| 29b. Polyquaterium-11 | — | — | — | — | — | 0.2 | — |
| 30. Cocodimonium Silk Amino Acids | — | — | 1.0 | — | — | — | — |
| 31. Keratin Amino Acids | — | — | — | — | — | 1.0 | — |
| 32. Hydrolyzed Collagen Protein | — | — | — | — | — | — | 1.0 |
| 33. Wheat Germ Oil | — | — | — | — | — | 0.1 | — |
| 34. Tocopherol Acetate (Vitamin E) | — | — | — | — | — | 0.1 | — |
| 35. Panthenol (Provitamin B5) | — | — | — | — | — | 0.5 | — |
| 36. Balsam | — | — | — | — | — | 0.1 | — |
| 37. Hydroxypropyl Cellulose | — | — | — | — | 0.1 | — | — |
| 38. Cetyl Alcohol | 0.2 | 0.5 | — | — | — | — | — |
| 39. Stearyl alcohol | 0.2 | 0.5 | — | — | — | — | — |
| 40. Propylene Glycol | 0.5 | 0.5 | 0.5 | — | — | — | — |
| 41. 2-Phenoxyethanol | 0.2 | — | — | — | — | — | — |
| 42. Methylchloroisothiazoline | — | — | — | — | 0.05 | — | — |
| 43. Methylisothiazoline | — | — | — | — | 0.05 | — | — |
| 44. DMDM Hydantoin | — | — | — | 0.5 | — | — | 0.3 |
| 45. Imidazolidinyl Urea | — | — | — | — | — | 0.2 | — |
| 46. Diazolidinyl Urea | 0.2 | 0.2 | 0.2 | 0.2 | — | — | — |
| 47. Methyl Paraben | 0.2 | 0.2 | 0.2 | — | 0.2 | 0.2 | 0.1 |
| 48. Propyl Paraben | 0.1 | 0.1 | 0.1 | — | — | 0.1 | 0.1 |
| 49. Tetrasodium EDTA | — | — | — | 0.1 | — | 0.1 | — |
| 50. Butylated Hydroxytoluene | — | — | 0.1 | — | — | — | — |

-continued

| Example<br>Ingredients (By Weight) | 104<br>% | 105<br>% | 106<br>% | 107<br>% | 108<br>% | 109<br>% | 110<br>% |
|---|---|---|---|---|---|---|---|
| 51. Sodium Chloride (50%) Adjust Viscosity | — | q.s. | q.s. | — | q.s. | q.s. | — |
| 52. Ammonium Chloride (35%) Adjust Viscosity | q.s. | — | — | q.s. | — | — | q.s. |
| 53. Sodium Hydroxide (10%) pH to 6–7 | — | — | q.s. | — | — | — | — |
| 54. Sodium Citrate (35%) | 0.3 | — | — | — | — | — | — |
| 55. Citric Acid (35%) pH to 5–7 | q.s. | q.s. | — | — | — | q.s. | q.s. |
| 56. Lactic Acid (35%) pH to 5–7 | — | — | q.s. | q.s. | q.s. | — | — |
| 57. Dye (0.2%–1%) | q.s. | q.s. | q.s. | q.s. | q.s. | q.s. | q.s. |
| 58. Fragrance | q.s. | q.s. | q.s. | q.s. | q.s. | q.s. | q.s. |
| 59. Water | 26.9 | 21.9 | 58.9 | 50.2 | 42.6 | 59.1 | 47.8 |

Quaternium-14 (Polyoxypropylene-9 Methyldiethylammonium Chloride)
Quaternium-22 (Gluconamidopropyldimethyl 2-Hydoxyethylammonium Chloride)
Quaternium-19 (Cationic Polymer of Hydroxyethyl Cellulose/Epichlorohydrin/Trimethylamine)
Polyquaternium-11 (Cationic Polymer of Vinylpyrrolidone/Dimethylaminoethylmethacrylate/Dimethylsulfate)

Example 104

A Peadescent Conditioning Shampoo Composition with Silicone Fluid

Container A is charged with 59 and 24. Heat to 40° C. and stir rapidly until 24 is hydrated. Add 25, 27, 40, 41, 46, 47, 48 and 54. Mix thoroughly. Container B is charged with 2, 8, 14, 22, 26, 38 and 39 which is heated to 65° C. with moderate stirring. Slowly add A to B while stirring and then add 58, 57, 52 and 55. Mix thoroughly, cool down the mixture to room temperature and discharge when homogeneous.

Example 105

A Pearlescent Conditioning Shampoo Composition with Moisturizer and Silicone Fluid Container A is charged with 59 and 26. Heat to 40° C. and stir rapidly until 26 is uniform. Add 3 and mix until uniform. Container B is charged with 4, 15, 25b, 23, 38, 39, 28, 18 and 19. Mix thoroughly and heat to 75° C. Slowly add B to A while stirring. Cool down the mixture to room temperature and add 40, 46, 47, 48, 58, 57, 51 and 55. Mix thoroughly, heat if necessary and discharge when homogeneous.

Example 106

A Clear Conditioning Shampoo Composition with Amino Acids

Container A is charged with 59, 10, 14, 12, 21 and 7 which is heat to 75° C. When uniform and clear cool to 40° C. and add 40, 46, 47, 48, 50, 58, 57, 51 and 53. Mix thoroughly, cool down the mixture to room temperature and discharge when homogeneous.

Example 107

A Clear Conditioning Shampoo Composition

Container A is charged with 59 and 29. Stir moderately until 29 is hydrated. Container B is charged with 2, 9, 49, 44, 13 and 14 which is heated to 60° C. with moderate stirring. Cool down the mixture to room temperature and slowly add A to B while stirring and then add 58, 57, 52 and 56. Mix thoroughly, heat if necessary and discharge when homogeneous.

Example 108

A Pearlescent Conditioning Shampoo Composition with Moisturizer

Container A is charged with 59, 1, 6, 13, 14, 42, 43, 20, 47, 23, 28, 37 and 17 which is heated to 70° C. and mixed until uniform. Cool to 40° C., add 58, 57, 51 and 56. Mix thoroughly, cool down the mixture to room temperature and discharge when homogeneous.

Example 109

A Pearlescent Conditioning Shampoo Composition with Moisturizer, Wheat Germ Oil, Vitamins and Balsam Container A is charged with 59 and 29b. Disperse 29b, then heat to 70° C. until 29b dissolves. Add 6 and 10. Mix until uniform and clear. Add 14, 22, 47, 48 and 49. Mix thoroughly. Cool to 50° C., add 45, 18, 31, 33, 34, 35 and 36. Cool down the mixture to room temperature. Add 58, 57, 51 and 55. Mix thoroughly, heat if necessary and discharge when homogeneous.

Example 110

A Clear Ultra Mild Conditioning Shampoo Composition with Protein

Container A is charged with 59, 2, 5, 11 and 16 which is heated to 60° C. and mixed until clear. Add 29 and 32. Mix until uniform and clear. Cool down the mixture to room temperature. Add 44, 47, 48, 58, 57, 52 and 55. Mix thoroughly, heat if necessary and discharge when homogeneous.

Examples 111–117

Prototype Conditioning Shampoo, Permanent Wave, Hair Straightening and Mousse Compositions Comprising Heteroatom Containing Alkyl Aldonamide Compounds

| Example<br>Ingredients (By Weight) | 111<br>% | 112<br>% | 113<br>% | 114<br>% | 115<br>% | 116<br>% | 117<br>% |
|---|---|---|---|---|---|---|---|
| 1. Ammonium Lauryl Sulfate (28%) | — | 35.0 | — | — | — | — | — |
| 2. Triethanolamine Lauryl Sulfate (40%) | 30.0 | — | 30.0 | — | — | — | — |
| 3. Sodium Laureth-2 Sulfate (26%) | 7.0 | — | — | — | — | — | — |

-continued

| Example<br>Ingredients (By Weight) | 111<br>% | 112<br>% | 113<br>% | 114<br>% | 115<br>% | 116<br>% | 117<br>% |
|---|---|---|---|---|---|---|---|
| 4. Disodium cocoamido MIPA Sulfosuccinate (40%) | — | 5.0 | — | — | — | — | — |
| 5. Sodium Isostearoyl Lactylate | — | — | 2.2 | — | — | — | — |
| 6. DEA-Oleth-10 Phosphate | — | — | — | — | 1.5 | 1.5 | — |
| 7. Cocoamidopropyl Betaine (30%) | 7.0 | — | — | 10.0 | — | — | — |
| 8. Cocoamidopropylhydroxy Sultaine | — | — | — | — | — | — | 1.5 |
| 9. Isostearoamphopropionate (35%) | — | 4.0 | — | — | — | — | — |
| 10. Stearamidopropyldimethylamine Lactate | — | — | — | 3.7 | — | — | — |
| 11. Lauramide DEA | 2.0 | — | — | — | — | — | — |
| 12. C8/C10 Oxypropyl D-Lactobionamide (50%) | 4.0 | 3.0 | 9.0 | — | — | — | — |
| 13. C12 Oxypropyl D-Lactobionamide (50%) | — | 3.0 | — | — | — | — | — |
| 14. Cocoaminopropyl D-Gluconamide (50%) | — | — | 0.5 | — | — | — | — |
| 15. Cocoaminopropyl D-Lactobionamide (50%) | — | — | — | 0.5 | 0.5 | 0.5 | 0.5 |
| 16. Lactamide MEA | — | — | — | 0.5 | — | — | — |
| 17. Stearalkonium Chloride | — | — | — | 1.0 | — | — | — |
| 18. Gaur Hydroxypropyltrimonium Chloride | — | — | — | 0.5 | — | — | — |
| 19. Cocodimonium Hydrolyzed Collagen | 1.5 | — | — | 1.0 | — | — | 2.0 |
| 20. Cocoyldimethylammonium Hydrolyzed Collagen | — | — | — | — | 1.0 | — | — |
| 21. Quaternium-6 | — | — | — | — | — | — | 1.5 |
| 22. Keratin Amino Acids | — | — | — | 0.5 | — | — | — |
| 23. Ethylene Glycol Monostearate | — | 1.0 | — | — | — | — | — |
| 24. Stearic Acid | — | — | — | — | 2.0 | — | — |
| 25. Cetyl Alcohol | — | — | — | — | 2.0 | 1.0 | — |
| 26. Cetearyl Alcohol | — | — | — | 3.0 | — | — | — |
| 27. Steareth-2 | — | — | — | — | 0.5 | 0.5 | — |
| 28. Steareth-10 | — | — | — | — | 2.5 | 2.5 | — |
| 29. Panthenol (Provitamin B5) | — | 1.0 | — | — | — | — | — |
| 30. Mineral Oil | — | — | — | — | 13.0 | 15.0 | — |
| 31. Emulsifying Wax | 3.0 | — | — | — | — | 7.5 | — |
| 32. Petrolatum | — | — | — | — | 11.5 | 4.0 | — |
| 33. Serum Albumin | — | — | 1.0 | — | — | — | — |
| 34. Benzophenone-4 | — | 0.3 | — | — | — | — | — |
| 35. Ammonium Thioglycolate (60%) | — | — | — | — | 9.0 | — | — |
| 36. Quaternium-15 | — | 0.2 | — | — | — | — | — |
| 37. SD Alcohol-40 | — | — | — | — | — | — | 15.0 |
| 38. Propylene Glycol | 0.5 | — | — | 2.5 | 2.5 | 2.5 | — |
| 39. Diazolidinyl Urea | 0.2 | — | — | 0.2 | 0.2 | 0.2 | — |
| 40. Methyl Paraben | 0.2 | — | — | 0.2 | 0.2 | 0.2 | — |
| 41. Propyl Paraben | 0.1 | — | — | 0.1 | 0.1 | 0.1 | — |
| 42. Trisodium HEDTA | — | — | — | — | 0.5 | — | — |
| 43. Sodium Chloride (50%) Adjust Viscosity | q.s. | — | q.s. | — | — | — | — |
| 44. Ammonium Chloride (35%) Adjust Viscosity | — | q.s. | — | — | — | — | — |
| 45. Ammonium Hydroxide (30%) pH to 8–9 | — | — | — | — | 2.8 | — | — |
| 46. Sodium Hydroxide (30%) pH to 8–9 | — | — | — | — | — | 2.8 | — |
| 47. Citric Acid (35%) pH to 5–7 | q.s. | q.s. | — | q.s. | — | — | — |
| 48. Lactic Acid (35%) pH to 5–7 | — | — | q.s. | — | — | — | — |
| 49. Dye (0.2%–1%) | q.s. | q.s. | q.s. | q.s. | — | — | — |
| 50. Fragrance | q.s. | q.s. | q.s. | q.s. | q.s. | q.s. | q.s. |
| 51. Water | 44.5 | 47.5 | 57.3 | 76.3 | 50.2 | 61.7 | 79.5 |
| 52. Propane/Isobutane Propellent | — | — | — | — | — | — | 15.0 |

Quaternium-6 (Polyoxypropylene-9 Methyldiethylammonium Chloride)

Example 111

A Pearlescent Conditioning Shampoo Composition For Permanent Waved, Tinted, Bleached or Relaxed Hair Container A is charged with 51, 2, 3, 7, 11, 12, 19, 31, 38, 39, 40 and 41 which is heated to 75° C. with moderate stirring until uniform. Cool down the mixture to room temperature and add 50, 49, 43 and 47. Mix thoroughly, heat if necessary and discharge when homogeneous.

Example 112

A Pearlescent Conditioning Shampoo Composition with Vitamins and Sunscreen For Permanent Waved, Tinted, Bleached or Relaxed Hair Container A is charged with 1, 4, 9, 12, 13, 23 and 34 which is heated to 65° C. with moderate stirring. Container B is charged with 51 and 29. Mix thoroughly until 29 dissolves. Slowly add B to A while stirring at 40° C. and then add 36, 50, 49, 44 and 47. Mix thoroughly, cool down to room temperature and discharge when homogeneous.

Example 113

A Clear Conditioning Shampoo Composition with Moisturizer and Protein For Permanent Waved, Tinted, Bleached or Relaxed Hair Container A is charged with 51, 2, 5, 12, and 14 which is heated to 75° C. with moderate stirring until uniform. Cool down the mixture 45° C. and add 33, 50, 49, 44 and 48. Mix thoroughly, cool down to room temperature and discharge when homogeneous.

Example 114

A Pearlescent Conditioner Composition with Moisturizer, Protein and Amino Acids For Permanent Waved, Tinted, Bleached or Relaxed Hair Container A is charged with 51 and 18. Mix thoroughly until 18 is hydrated. Add 38, 39, 40, 41, 19, 16 and 22. Heat the mixture to 80° C. with moderate stirring. Add 7, 10, 15, 17, 50 and 49. Mix thoroughly. Add 26 and mix thoroughly.

Cool down the mixture to room temperature and add 47. Mix thoroughly, heat if necessary and discharge when homogeneous.

Example 115

A Pearlescent Conditioning Permanent Wave Composition with Protein

Container A is charged with 25, 6, 27, 30, 32 and 24 which is heated to 80° C. with moderate stirring. Container B is charged with 51, 28, 20, 38, 15, 42, 50, 39, 40 and 41 which is heated to 80° C. with moderate stirring. Container C is charged with 35 and 45. Mix thoroughly. Slowly add B to A with good stirring. When uniform add C at 35° C. Mix thoroughly, cool down the mixture to room temperature and discharge when homogeneous.

Example 116

A Hair Relaxer/Straightener Composition

Container A is charged with 25, 6, 27, 30, 31 and 32 which is heated to 80° C. with moderate stirring. Container B is charged with 51, 28, 38, 15, 50, 39, 40 and 41 which is heated to 80° C. with moderate stirring. Slowly add B to A with good stirring. When uniform add 46 at 35° C. Mix thoroughly, cool down the mixture to room temperature and discharge when homogeneous.

Example 117

A Conditioning Hair Styling Mousse Composition

Container A is charged with 51, 37, 8, 15, 19, 21 and 50. Mix thoroughly until clear. Discharge into a lined aerosol container and pressurize with 52 at a 85%:15% concentrate:propellant ratio.

Examples 118–124

Prototype Antidandruff Shampoo Compositions Comprising Heteroatom Containing Alkyl Aldonamide Compounds

| Example<br>Ingredients (By Weight) | 118<br>% | 119<br>% | 120<br>% | 121<br>% | 122<br>% | 123<br>% | 124<br>% |
| --- | --- | --- | --- | --- | --- | --- | --- |
| 1. Sodium Laureth-2 Sulfate (26%) | — | 25.0 | — | 40.0 | — | — | — |
| 2. Ammonium Lauryl Sulfate (28%) | — | — | 25.0 | — | — | — | — |
| 3. Triethanolamine Lauryl Sulfate (40%) | 25.0 | — | — | 4.0 | 30.0 | 20.0 | 35.0 |
| 4. Sodium Lauryl Sarcosinate (30%) | 10.0 | — | — | — | — | 8.5 | — |
| 5. Disodium Oleamido PEG-2 Sulfosuccinate (30%) | — | — | 15.0 | — | — | — | — |
| 6. PPG-5 Ceteth-10 Phosphate | — | 0.6 | — | — | — | — | — |
| 7. PPG-20 Lanolin ether | — | — | — | — | — | — | 4.3 |
| 8. Coco Betaine (35%) | — | — | 6.0 | — | — | — | — |
| 9. Cocoamidopropyl Betaine (35%) | — | 20.0 | — | — | 15.5 | 4.3 | — |
| 10. C8/C10 Oxypropyl D-Gluconamide | — | — | 1.0 | — | — | — | — |
| 11. C8/C10 Oxypropyl D-Lactobionamide (50%) | 4.0 | 6.0 | — | 10.0 | — | 7.0 | — |
| 12. C12 Oxypropyl D-Lactobionamide (50%) | — | — | 6.0 | — | — | — | — |
| 13. C12–C15 Oxypropyl D-Lactobionamide (50%) | — | — | — | — | 10.0 | — | 4.0 |
| 14. Ethylene Glycol Distearate | — | — | — | — | 2.0 | — | 2.0 |
| 15. Cocodimonium Hydrolyzed Collagen Protein | — | 1.0 | — | — | — | — | — |
| 16. Hydrolyzed Collagen Protein | — | — | — | 1.5 | — | — | — |
| 17. Glycerine | — | 1.0 | — | — | — | — | — |
| 18. Zinc Pyrithione (48%) | 3.0 | — | 2.0 | 2.0 | 3.0 | — | 2.0 |
| 19. Bispyrithione/Magnesium Sulfate | — | 1.5 | — | — | — | — | — |
| 20. Selenium Sulfide | — | — | — | — | — | 1.0 | — |
| 21. Benzophenone-4 | — | 0.3 | — | — | — | — | — |
| 22. Titanium Dioxide | — | — | — | — | — | 1.0 | — |
| 23. Magnesium Aluminum Silicate | — | — | 1.0 | 1.2 | — | 1.2 | — |
| 24. Hydroxypropyl Cellulose | — | — | 0.5 | — | — | — | 0.7 |
| 25. Hydroxypropyl Methylcellulose | — | — | — | — | — | 1.1 | — |
| 26. Xanthan Gum | 0.5 | — | — | — | — | — | — |
| 28. Propylene Glycol | — | 0.5 | 0.5 | — | 0.5 | 1.0 | — |
| 29. DMDM Hydantoin | — | — | — | 0.3 | — | 0.3 | 0.3 |
| 30. Diazolidinyl Urea | — | 0.2 | 0.2 | — | 0.2 | — | — |
| 31. Methyl Paraben | 0.2 | 0.2 | 0.2 | — | 0.2 | — | — |
| 32. Propyl Paraben | — | 0.1 | 0.1 | — | 0.1 | — | — |
| 33. Tetrasodium EDTA | — | — | — | 0.1 | — | — | — |
| 34. Sodium Chloride (50%) Adjust Viscosity | q.s. | q.s. | — | q.s. | q.s. | q.s. | q.s. |
| 35. Ammonium Chloride (35%) Adjust Viscosity | — | — | q.s. | — | — | — | — |
| 36. Citric Acid (35%) pH to 5–7 | — | q.s. | q.s. | q.s. | — | q.s. | q.s. |
| 37. Lactic Acid (35%) pH to 5–7 | q.s. | — | — | — | q.s. | — | — |
| 38. Dye (0.2%–1%) | q.s. | q.s. | q.s. | q.s. | q.s. | q.s. | q.s. |
| 39. Fragrance | q.s. | q.s. | q.s. | q.s. | q.s. | q.s. | q.s. |
| 40. Water | 56.3 | 43.6 | 43.5 | 42.4 | 38.5 | 56.4 | 48.9 |

Example 118

A Clear Antidandruff Shampoo Composition

Container A is charged with 40 and 26. Stir rapidly until 26 is hydrated. Add 38 and mix thoroughly. Container B is charged with 3, 4 and 11 which is heated to 40° C. with moderate stirring. Cool down the mixture to room temperature and add 18 and 31. Mix thoroughly. Slowly add B to A while stirring and then add 39, 34 and 37. Mix thoroughly, heat if necessary and discharge when homogeneous.

Example 119

A Clear Antidandruff Conditioning Shampoo Composition with Protein, Moisturizer and Sunscreen Container A is charged with 19 and about 15% of 40. Container B is charged with 40, 17, 28, 30, 31, 32, 6, 15, 21, 38, and 39. Mix thoroughly. Add 1, 9 and 11. Mix until clear. Slowly add A to B and stir until clear. Add 34 and 36. Mix thoroughly, heat if necessary and discharge when homogeneous.

Example 120

A Pearlescent Antidandruff Shampoo Composition

Container A is charged with 40 and 23. Stir rapidly until 23 is hydrated and smooth. Container B is charged with 2, 5, 8, 10, 12 and 24 which is heated to 65° C. with moderate stirring. Cool down the mixture to room temperature and add 18, 28, 30, 31 and 32. Mix thoroughly. Slowly add B to A while stirring and then add 38, 39, 35 and 36. Mix thoroughly, heat if necessary and discharge when homogeneous.

Example 121

A Peadescent Antidandruff Conditoning Shampoo Composition with Protein

Container A is charged with 40, 33 and 23. Stir rapidly until 23 is hydrated and smooth. Container B is charged with 1, 3, and 11 which is heated to 60° C. with moderate stirring. Cool down the mixture to room temperature and add 16, 29, and 18. Mix thoroughly. Slowly add B to A while stirring and then add 38, 39, 34 and 36. Mix thoroughly, heat if necessary and discharge when homogeneous.

Example 122

A Peadescent Antidandruff Shampoo Composition

Container A is charge with 40, 3, 9, 13 and 14 which is heated to 70° C. with moderate stirring until uniform. Cool down the mixture to room temperature and add 18, 28, 30, 31 and 32. Mix thoroughly and add 38, 39, 34 and 37. Mix thoroughly, heat if necessary and discharge when homogeneous.

Example 123

A Pearlescent Antidandruff Shampoo Composition

Container A is charged with 40 and 23. Stir rapidly until 23 is hydrated. Add 22, 28 and 29 mix thoroughly. Container B is charged with 3, 4, 9 and 11 which is heated to 70° C. with moderate stirring. Grind 20 and 25 and add mixture at 50° C. Mix thoroughly. Slowly add B to A while stirring and then add 38, 39, 34 and 36. Mix thoroughly, cool down the mixture to room temperature and discharge when homogeneous.

Example 124

A Pearlescent Antidandruff Shampoo Composition

Container A is charged with 40 and 24. Stir rapidly until 24 is hydrated. Add 38 and mix thoroughly. Container B is charged with 3, 6, 13 and 14 which is heated to 80° C. with moderate stirring. Cool down the mixture to 50° C. and add 18 and 28. Mix thoroughly. Slowly add B to A while stirring and then add 38, 39, 34 and 36. Mix thoroughly, cool down the mixture to room temperature and discharge when homogeneous.

Examples 125–131

Prototype Conditioning and Rinse Compositions Comprising Heteroatom Containing Alkyl Aldonamide Compounds

| Example<br>Ingredients (By Weight) | 125<br>% | 126<br>% | 127<br>% | 128<br>% | 129<br>% | 130<br>% | 131<br>% |
|---|---|---|---|---|---|---|---|
| 1. PEG-8 Stearate | — | 10.0 | — | — | — | — | — |
| 2. PEG-100 Stearate | — | — | 2.5 | — | — | — | — |
| 3. Methyl Gluceth-20 | — | — | 1.0 | 2.0 | — | — | — |
| 4. Coconut Methyl Glucamide | — | — | — | — | — | 1.0 | — |
| 5. PEG-40 Hydrogenated Castor Oil | — | — | — | — | 1.0 | — | — |
| 6. PEG-75 Lanolin | — | — | — | 1.0 | — | — | — |
| 7. Octoxynol-9 | — | — | 0.4 | — | — | — | — |
| 8. Ceteth-2 | — | — | 1.0 | — | — | 0.5 | — |
| 9. Oleth-10 | — | — | — | 3.5 | — | — | — |
| 10. Laneth-16 | — | — | — | 1.0 | — | — | — |
| 11. White Petrolatum | — | — | 1.5 | — | — | — | — |
| 12. Mineral Oil | — | — | 1.0 | — | — | — | — |
| 13. Caster Oil | 2.5 | — | — | — | — | — | — |
| 14. Stearic Acid | 1.5 | — | — | — | — | — | — |
| 15. Cocoaminopropyl D-Gluconamide HCl | 3.0 | — | — | — | — | — | — |
| 16. Oleylaminopropyl D-Glucoanmide HCl | — | 1.0 | — | — | — | — | — |
| 17. Cocoaminopropyl D-Lactobionamide HCl | — | — | — | 2.0 | 1.0 | — | — |
| 18. Tallowaminopropyl D-Lactobionamide HCl | — | — | 3.0 | — | — | 0.5 | — |
| 19. C12–C15 Oxypropylaminopropyl Lactobionamide | — | — | — | — | — | — | 1.5 |
| 20. Panthenol (Provitamin B5) | — | 0.7 | — | 0.2 | 0.7 | — | — |
| 21. Aloe Vera Gel | — | 4.0 | — | — | — | — | — |
| 22. Allantoin | — | — | — | 0.2 | — | — | — |
| 23. Hydrolyzed Collagen Protein | 1.0 | 1.0 | — | — | — | — | — |
| 24. Magnesium Aluminum Silicate (5%) | 30.0 | — | — | — | — | — | — |
| 25. Xanthan Gum | — | — | 0.2 | — | — | — | — |
| 26. Acetamide MEA (75%) | — | 4.0 | — | — | — | — | — |
| 27. Glycerin | 3.5 | — | — | — | — | — | — |
| 28. Quaternium-15 | 0.3 | — | — | — | — | — | — |

-continued

| Example<br>Ingredients (By Weight) | 125<br>% | 126<br>% | 127<br>% | 128<br>% | 129<br>% | 130<br>% | 131<br>% |
|---|---|---|---|---|---|---|---|
| 29. Quaternium-22 | — | — | — | — | 1.0 | — | — |
| 30. Quaternium-33 | — | — | — | 1.5 | — | — | — |
| 31. Polyquaternium-11 | — | — | 1.0 | — | — | — | — |
| 32. Stearalkonium Chloride | — | 5.0 | 3.5 | — | — | 1.5 | — |
| 33. Steartrimonium Hydrolyzed Collagen Protein | — | — | 3.0 | — | — | — | — |
| 34. Benzophenone-8 | — | — | — | — | — | 0.2 | — |
| 35. Ethyl Dihydroxy PABA | — | — | — | 0.5 | — | — | — |
| 36. Hydroxyethyl Cellulose | — | — | — | — | 1.0 | — | — |
| 37. Cetyl Octanoate | — | — | — | — | — | — | 2.0 |
| 38. Cetyl Lactate | — | — | — | — | — | 2.0 | — |
| 39. Cetyl Alcohol | 3.5 | 3.0 | 2.0 | — | — | — | 3.0 |
| 40. Stearyl Alcohol | — | — | — | — | — | 2.5 | — |
| 41. Lanolin Alcohol | — | — | 1.0 | — | — | — | — |
| 42. Glyceryl Stearate | 4.5 | — | 1.0 | — | — | 1.0 | 1.0 |
| 43. Propylene Glycol | 0.5 | — | 0.5 | 0.5 | — | 0.5 | 3.0 |
| 44. Imidazolidinyl Urea | — | 0.2 | — | — | 0.2 | — | — |
| 45. Diazolidinyl Urea | 0.2 | — | 0.2 | 0.2 | — | 0.2 | — |
| 46. Methyl Paraben | 0.2 | 0.2 | 0.2 | 0.2 | 0.2 | 0.2 | 0.1 |
| 47. Propyl Paraben | 0.1 | 0.1 | 0.1 | 0.1 | 0.1 | 0.1 | — |
| 48. Butyl Paraben | — | — | — | — | — | — | 0.1 |
| 49. Citric Acid (10%) | — | — | 0.5 | — | — | — | 0.5 |
| 50. Fragrance | q.s. | q.s. | q.s. | q.s. | q.s. | q.s. | q.s. |
| 51. Water | 49.2 | 70.8 | 76.4 | 87.1 | 94.8 | 89.8 | 88.8 |

Quaternium-15 (1-{3-Chloroallyl}-3,5,7-Triaza-1-azoniaadamantane Chlorode)
Quaternium-22 (Gluconamidopropyldimethyl 2-Hydroxyethylammonium Chloride)
Quaternium-33 (Lanolinamidopropyldimethylethylammonium Chloride)
Polyquaternium-11 (Copolymer of Vinylpyrrolidone/Dimethylaminoethyl Methacrylate/Dimethylsulfate)

Example 125

A Pearlescent Conditioning Composition with Moisturizer and Protein

Container A is charged with 51, 24, 28, 17, 15 and 23 which is heated to 65° C. with moderate stirring. Container B is charged with 42, 39, 14 and 13 which is heated to 65° C. with moderate stirring. Slowly add A to B while stirring and then add 43, 50, 45, 46 and 47. Mix thoroughly, cool down the mixture to room temperature and discharge when homogeneous.

Example 126

A Pearlescent Conditioning Composition with Moisturizer, Aloe, Vitamins and Protein Container A is charged with 51, 47, 46, 32, 1, 39, 26, 23, 20, 44, 16 and 21 which is heated to 70° C. with moderate stirring. Cool down the mixture to 40° C. and add 50. Mix thoroughly, cool down the mixture to room temperature and discharge when homogeneous.

Example 127

A Pearlescent Conditioning Composition with Protein

Container A is charged with 51 and 25 which is heated to 80° C. and stirred rapidly. After 25 is hydrated, add 2 and 42. Mix thoroughly until clear and uniform. Container B is charged 39, 41, 49, 11, 12, 8, 3, 31 and 7 which is heated to 80° C. Slowly add B to A while stirring and then add 32, and 33. Mix thoroughly and add 50, 43, 46, 47 and 48. Mix thoroughly, cool down the mixture to room temperature and discharge when homogeneous.

Example 128

A Clear Conditioning Composition with Vitamins and Sunscreen

Container A is charged with 51, 43, 45, 46, 47, 3, 6, 17, 20, 22 and 30 with moderate stirring. Container B is charged with 9, 10 and 35 which is heated to 65° C. with moderate stirring. When B is clear and uniform, add B to A and then add 50 with moderate stirring. Mix thoroughly, heat if necessary and discharge when homogeneous.

Example 129

A Clear Rinse Composition with Vitamins

Container A is charged with 51, 44, 46, 47 and 36. Stir rapidly and disperse 36. Container B is charged with 5, 17, 29, 50 and 20. Mix thoroughly, heat if necessary and discharge when homogeneous.

Example 130

A Pearlescent Composition with Sunscreen

Container A is charged with 51, 4, 18, 43, 45, 46 and 47 which is heated to 70° C. with moderate stirring. Container B is charged with 38, 40, 42, 32, 8 and 34 which is heated to 70° C. with moderate stirring. Slowly add B to A while stirring and then add 50. Mix thoroughly, cool down the mixture to room temperature and discharge when homogeneous.

Example 131

A Pearlescent Rinse Composition

Container A is charged with 51, 19, 43, 46, 48 and 49 which is heated to 70° C. with moderate stirring. Container B is charged with 37, 39, and 42 which is heated to 70° C. with moderate stirring. Slowly add B to A while stirring and then add 50. Mix thoroughly, cool down the mixture to room temperature and discharge when homogeneous.

Examples 132–135

Prototype Hair Care Compositions Comprising Heteroatom Containing Alkyl Aldonamide Compounds as the Main Active

| Example<br>Ingredients (By Weight) | 132 % | 133 % | 134 % | 135 % | % | % | % |
|---|---|---|---|---|---|---|---|
| 1. C8/C10 Oxypropyl D-Gluconamide | — | 5.0 | 5.0 | — | — | — | — |
| 2. N-Gluconyl Dodecyldi(oxyethyl) Glycinate | 5.0 | — | — | — | — | — | — |
| 3. C8/C10 Oxypropyl D-Lactobionamide (50%) | 40.0 | 15.0 | 15.0 | 20.0 | — | — | — |
| 4. C12–C15 Oxypropyl D-Lactobionamide (50%) | — | — | 10.0 | — | — | — | — |
| 5. C8–C10 Alkylpolyglycoside (50%) | — | 10.0 | — | — | — | — | — |
| 6. Ammonium Laureth-3 Sulfate (28%) | — | — | — | 16.0 | — | — | — |
| 7. Glycerin | 3.0 | 3.0 | 3.0 | — | — | — | — |
| 8. Quaternium-22 | — | 2.0 | 2.0 | — | — | — | — |
| 9. Hydrolyzed Animal Protein | — | — | 0.5 | — | — | — | — |
| 10. Panthenol (Provitamin B) | — | — | 0.1 | — | — | — | — |
| 11. Benzophenone-4 | 0.3 | 0.3 | 0.3 | — | — | — | — |
| 12. Sodium Pyrrolidone Carboxylic Acid | 0.5 | — | — | — | — | — | — |
| 13. Hydroxypropyl Cellulose | 1.0 | 1.0 | 1.0 | — | — | — | — |
| 14. Zinc Pyrithione (48%) | — | — | — | 2.0 | — | — | — |
| 15. Ethylene Glycol Distearate | — | — | 2.0 | 3.0 | — | — | — |
| 16. Dimethicone | — | — | — | 1.0 | — | — | — |
| 17. Ammonium Xylene Sulfonate (40%) | — | — | — | 1.3 | — | — | — |
| 18. Tricethylmethylammonium Chloride | — | — | — | 0.3 | — | — | — |
| 19. Balsam | — | — | 0.1 | — | — | — | — |
| 20. Stearyl Alcohol | — | — | — | 0.4 | — | — | — |
| 21. Cetyl alcohol | — | — | — | 0.1 | — | — | — |
| 22. Butylated Hydroxytoluene | 0.1 | 0.1 | 0.1 | — | — | — | — |
| 23. Tetrasodium EDTA | 0.1 | 0.1 | 0.1 | 0.1 | — | — | — |
| 24. Propylene Glycol | 0.5 | 0.5 | 0.5 | 0.5 | — | — | — |
| 25. DMDM Hydantoin | — | — | 0.1 | — | — | — | — |
| 26. Diazolidinyl Urea | 0.2 | 0.2 | 0.2 | 0.2 | — | — | — |
| 27. Methyl Paraben | 0.2 | 0.2 | 0.2 | 0.2 | — | — | — |
| 28. Propyl Paraben | 0.1 | 0.1 | — | 0.1 | — | — | — |
| 29. Butyl Paraben | — | — | 0.1 | — | — | — | — |
| 30. Ammonium Chloride (35%) Adjust Viscosity | — | — | — | q.s. | — | — | — |
| 31. Citric Acid (35%) pH to 5–7 | q.s. | q.s. | q.s. | — | — | — | — |
| 32. Lactic Acid (35%) pH to 5–7 | — | — | — | q.s. | — | — | |
| 33. Dye (0.2%–1%) | — | q.s. | q.s. | q.s. | — | — | — |
| 34. Fragrance | q.s. | q.s. | q.s. | q.s. | — | — | — |
| 35. Water | 49.0 | 62.5 | 59.7 | 54.8 | — | — | — |

Quaternium-22 (Gluconamidopropyldimethyl 2-Hydroxyethylammonium Chloride)

Example 132

A Clear Shampoo Composition with Moisturizer and Sunscreen (No Dye)

Container A is charged with 35 and 13. Mix thoroughly until 13 is hydrated. Add 2, 3, and 7. Mix thoroughly. Add 11, 12, 22, 23, 24, 26, 27 and 28. Mix thoroughly. Add 34 and 31. Mix thoroughly, heat if necessary and discharge when homogeneous.

Example 133

A Clear Conditioning Shampoo Composition with Moisturizer and Sunscreen

Container A is charged with 35 and 13. Mix thoroughly until 13 is hydrated. Add 3, 5, 7, and 1. Mix thoroughly and heat to 70° C. Add 8, 11, 22, 23, 24, 26, 27 and 28. Mix thoroughly. Add 34, 33 and 31. Mix thoroughly, cool down the mixture to room temperature and discharge when homogeneous.

Example 134

A Pearlescent Conditioning Shampoo Composition with Moisturizer, Balsam, Protein, Vitamins and Sunscreen Container A is charged with 13 and 50% of 35. Mix thoroughly until 13 is hydrated. Add 8, 7, 24, 25, 26, 27 and 29. Mix thoroughly. Container B is charged 35, 3, 4 and 1 which is heated to 65° C. with moderate stirring. When clear, add 15, 9, 10, 11, 19, 21 and 22. Mix thoroughly. Slowly add A to B while stirring and then add 34, 33 and 31. Mix thoroughly, cool down the mixture to room temperature and discharge when homogeneous.

Example 135

A Pearlescent Antidandruff Conditioning Shampoo Composition with Silicone Fluid

Container A is charged with 16 and 50% of 35. Heat to 40° C. and stir rapidly until 16 is uniform. Add 6 and mix until uniform. Container B is charged with 35, 3, 17, 15, 20, 21 and 18. Mix thoroughly and heat to 75° C. Slowly add B to A while stirring. Cool down the mixture to room temperature and add 14, 23, 24, 26, 27, 28, 34, 33, 30 and 32. Mix thoroughly, heat if necessary and discharge when homogeneous.

This invention has been described with respect to certain preferred embodiments and various modifications and variations in the light thereof will be suggested to persons skilled in the art and are to be included within the spirit and purview of this application and the scope of the appended claims.

What is claimed is:

1. A hair care composition comprising:

(a) about 15% by wt. sodium lauryl sulfate;

(b) about 3% to about 5% by wt. of a heteroatom containing alkyl aldonamide compound having the following structure:

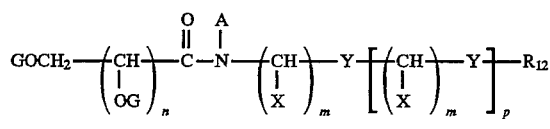

wherein:
n=1–6;
m=1–5;
X=H, a $C_1$–$C_4$ alkyl group or mixtures thereof;
Y=NA, $^+NH_2$, $^+NHA$, O, S, SO, $SO_2$,

or mixtures thereof;
p=0–25;
G=H, a mono-, di-, oligo-, polysaccharide group, a $(CH_2CH_2O)_q$—H;
$(CH_2CHCH_3O)_r$—H group or mixtures thereof;
q=1–50;
r=1–50;
A=H, a hydroxy $C_1$–$C_{18}$ alkyl group, a $C_1$–$C_{18}$ straight or branched chain, saturated or unsaturated hydrocarbon which may be unsubstituted or substituted with an aromatic, cycloaliphatic, mixed aromatic aliphatic radical or a

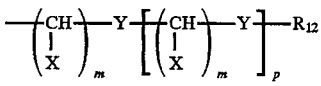

group or mixtures thereof; wherein X, m, Y and p are defined as above; and $R_{12}$ is a straight or branched chain, saturated or unsaturated hydrocarbon which may be unsubstituted or substituted with an aromatic, cycloaliphatic, or mixed aromatic aliphatic radical comprising from about 1 to about 28 carbon atoms;

(c) about 2% by wt. of a viscosity building ionizable salt selected from the group consisting of sodium chloride, potassium chloride, calcium chloride, magnesium chloride, potassium bromide, ammonium chloride, sodium sulfate, potassium sulfate, magnesium sulfate, sodium isethionate, sodium thiosulfate and mixtures thereof;

(d) 0.5 to 10% hair conditioning agent; and (e) water.

* * * * *